US012214199B2

(12) United States Patent
Halpern et al.

(10) Patent No.: US 12,214,199 B2
(45) Date of Patent: *Feb. 4, 2025

(54) TREATMENT FOR LOSS OF CONTROL DISORDERS

(71) Applicant: The Board of Trustees of the Leland Stanford Junior University, Palo Alto, CA (US)

(72) Inventors: Casey Halpern, Menlo Park, CA (US); Robert C. Malenka, Palo Alto, CA (US); Hemmings Wu, Palo Alto, CA (US)

(73) Assignee: THE BOARD OF TRUSTEES OF THE LELAND STANFORD JUNIOR UNIVERSITY, Palo Alto, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/188,120

(22) Filed: Mar. 22, 2023

(65) Prior Publication Data
US 2024/0042206 A1 Feb. 8, 2024

Related U.S. Application Data

(63) Continuation of application No. 16/337,315, filed as application No. PCT/US2017/053820 on Sep. 27, 2017, now Pat. No. 11,642,528.
(Continued)

(51) Int. Cl.
*A61N 1/36* (2006.01)
*A61B 5/00* (2006.01)
*A61N 1/05* (2006.01)

(52) U.S. Cl.
CPC ........ *A61N 1/36085* (2013.01); *A61B 5/4064* (2013.01); *A61N 1/05* (2013.01);
(Continued)

(58) Field of Classification Search
CPC .. A61N 1/360085; A61N 1/05; A61N 1/0529; A61N 1/36089; A61N 1/36139; A61B 5/4064
See application file for complete search history.

(56) References Cited

U.S. PATENT DOCUMENTS 6,176,242 B1 * 1/2001 Rise .................. A61M 5/14276
607/2
6,871,098 B2 * 3/2005 Nuttin ................ A61N 1/36082
607/45
(Continued)

FOREIGN PATENT DOCUMENTS

WO 2015164477 A1 10/2015
WO 2018064225 A1 4/2018

OTHER PUBLICATIONS

International Preliminary Report on Patentability received for PCT Application No. PCT/US/2017/053820, Mailed on Apr. 11, 2019, 15 Pages.
(Continued)

*Primary Examiner* — Eric D. Bertram
(74) *Attorney, Agent, or Firm* — Mintz, Levin, Cohn, Ferris, Glovsky and Popeo, P.C.

(57) ABSTRACT

The present invention provides, inter alia, methods, apparatus, and systems useful for ameliorating impulse control disorders known to be extremely disabling and common to many neurological and psychiatric conditions using closed-loop (responsive) neuro stimulation.

9 Claims, 59 Drawing Sheets

Related U.S. Application Data

(60) Provisional application No. 62/400,483, filed on Sep. 27, 2016.

(52) U.S. Cl.
CPC ....... *A61N 1/0529* (2013.01); *A61N 1/36089* (2013.01); *A61N 1/36139* (2013.01)

(56) References Cited

U.S. PATENT DOCUMENTS

| | | | | |
|---|---|---|---|---|
| 8,315,703 | B2* | 11/2012 | Lozano | A61N 1/36082 607/45 |
| 11,040,205 | B2* | 6/2021 | Kaemmerer | G16H 20/30 |
| 11,642,528 | B2* | 5/2023 | Halpern | A61N 1/05 607/45 |
| 2007/0027500 | A1* | 2/2007 | Maschino | A61N 1/36082 607/45 |
| 2011/0137371 | A1* | 6/2011 | Giftakis | A61B 5/293 607/45 |
| 2011/0144715 | A1* | 6/2011 | Molnar | A61N 1/36185 607/45 |
| 2012/0116475 | A1* | 5/2012 | Nelson | A61N 1/36082 607/45 |
| 2013/0053722 | A1* | 2/2013 | Carlson | A61B 5/316 607/45 |
| 2013/0184781 | A1 | 7/2013 | Eskandar et al. | |
| 2013/0197605 | A1* | 8/2013 | Carlson | A61N 1/36082 607/48 |
| 2013/0281890 | A1* | 10/2013 | Mishelevich | A61N 1/36085 601/2 |
| 2013/0317569 | A1* | 11/2013 | Deisseroth | A61K 48/0058 800/13 |
| 2014/0358024 | A1* | 12/2014 | Nelson | A61N 1/36139 607/45 |
| 2016/0250476 | A1* | 9/2016 | Kaemmerer | A61N 1/3614 607/45 |
| 2016/0367812 | A1* | 12/2016 | De Ridder | A61N 1/36185 |
| 2019/0247661 | A1* | 8/2019 | Eskandar | A61N 1/0534 |
| 2020/0030608 | A1 | 1/2020 | Halpern | |
| 2020/0376273 | A1 | 12/2020 | Halpern et al. | |

OTHER PUBLICATIONS

International Search Report and Written Opinion received for PCT Application No. PCT/US/2017/053820, Mailed on Nov. 29, 2017, 8 Pages.
Ali et al. (May-Jun. 2016, e-Publication Mar. 15, 2016) "Attitudes Toward Treating Addiction with Deep Brain Stimulation", Brain Stimulation, 9(3):466-468.
Ardestani et al. (Apr. 2015) "Insulin Cessation and Diabetes Remission After Bariatric Surgery in Adults with Insulin-Treated Type 2 Diabetes", Diabetes Care, 38(4):659-664.
Avila et al. (Feb. 2010, e-Published (Dec. 4, 2009)) "Beta Frequency Synchronization in Basal Ganglia Output during Rest and Walk in a Hemiparkinsonian Rat", Experimental Neurology, 221(2):307-319 (31 Pages).
Baxter et al. (Aug. 2003) "Basal Ganglia Systems in Ritualistic Social Displays: Reptiles and Humans; Function and Illness", Physiology & behavior, 79(3):451-460.
Beaver et al. (May 10, 2006) "Individual Differences In Reward Drive Predict Neural Responses to Images of Food", The Journal of Neuroscience, 26(19):5160-5166.
Bello et al. (Apr. 2, 2014) "Binge-like Eating Attenuates Nisoxetine Feeding Suppression, Stress Activation, and Brain Norepinephrine Activity", PLoS One, 9(4):1-11 Pages.
Bergey et al. (Feb. 24, 2015) "Long-Term Treatment with Responsive Brain Stimulation in Adults with Refractory Partial Seizures", Neurology, 84(8):810-817.
Bewernick et al. (Jan. 15, 2010) "Nucleus Accumbens Deep Brain Stimulation Decreases Ratings of Depression and Anxiety in Treatment-Resistant Depression", Biological Psychiatry, 67(2):110-116.
Blumenfeld et al. (Jan. 2017) e-Published (Nov. 8, 2016), "Sixty-Hertz Stimulation Improves Bradykinesia and Amplifies Subthalamic Low-Frequency Oscillations", Movement Disorders, 32(1):80-88.
Bohon et al. (Apr. 2009) "Female Emotional Eaters Show Abnormalities in Consummatory and Anticipatory Food Reward: A Functional Magnetic Resonance Imaging Study", International Journal of Eating Disorders, 42(3):210-221 (18 Pages).
Bohon Cara (Aug. 2014) "Greater Emotional Eating Scores Associated with Reduced Frontolimbic Activation to Palatable Taste in Adolescents", Obesity (Silver Spring), 22(8):1814-1820 (16 Pages).
Bray et al. (Apr. 6, 2002) "Medicinal Strategies In The Treatment of Obesity", Nature, 404:672-677.
Broft et al. (Jul. 2012) "Striatal Dopamine in Bulimia Nervosa: A Pet Imaging Study", International Journal of Eating Disorders, 45(5):648-656 (15 Pages).
Bronte-Stewart et al. (Oct. 2010) "Clinical Motor Outcome of Bilateral Subthalamic Nucleus Deep-Brain Stimulation for Parkinson's Disease Using Image-Guided Frameless Stereotaxy", Neurosurgery, 67(4):1088-1093.
Buckholtz et al. (Apr. 2010) "Mesolimbic Dopamine Reward System Hypersensitivity in Individuals with Psychopathic Traits", Nature Neuroscience, 13(4):419-421 (7 pages).
Carelli et al. (Dec. 1994) "A Comparison of Nucleus Accumbens Neuronal Firing Patterns During Cocaine Self-Administration and Water Reinforcement in Rats", The Journal of Neuroscience, 14(12):7735-7746.
Christoffel et al. (Jul. 2014) "Excitatory Transmission at Thalamo-Striatal Synapses Mediates Susceptibility to Social Stress", Nature Neuroscience, 18(7):962-964 (16 pages).
Christopher et al. (Feb. 2012, e-Published (Nov. 17, 2011)), "Enrolling in Deep Brain Stimulation Research for Depression: Influences on Potential Subjects' Decision Making", Depress Anxiety, 29(2):139-146.
Colles et al. (Mar. 2008) "Loss of Control is Central to Psychological Disturbance Associated with Binge Eating Disorder", Obesity (Silver Spring), 16(3):608-614.
Crockett et al. (Jul. 24, 2013) "Restricting Temptations: Neural Mechanisms of Precommitment", Neuron, 79(2):391-401.
Dalley et al. (Feb. 24, 2011) "Impulsivity, Compulsivity, and Top-Down Cognitive Control", Neuron, 69(4):680-694.
Demos et al. (Apr. 18, 2012) "Individual Differences in Nucleus Accumbens Activity to Food and Sexual Images Predict Weight Gain and Sexual Behavior", The Journal of Neuroscience, 32(16):5549-5552.
Denys et al. (Oct. 2010) "Deep Brain Stimulation of the Nucleus Accumbens for Treatment-Refractory Obsessive-Compulsive Disorder", Archives of General Psychiatry, 67(10):1061-1068.
Desai et al. (Jan.-Feb. 2016) "Asynchronous Distributed Multielectrode Microstimulation Reduces Seizures in the Dorsal Tetanus Toxin Model of Temporal Lobe Epilepsy", Brain Stimulation, 9(1):86-100 (35 Pages).
Dong et al. (Sep. 2012) "A New Method for Measuring Meal Intake in Humans via Automated Wrist Motion Tracking", Applied Psychophysiology and Biofeedback, 37(3):205-215 (25 Pages).
Dougherty et al. (Aug. 15, 2015) "A Randomized Sham-Controlled Trial of Deep Brain Stimulation of the Ventral Capsule/Ventral Striatum for Chronic Treatment-Resistant Depression", Biological Psychiatry, 78(4):240-248.
Einevoll et al. (Oct. 18, 2013) "Modelling and Analysis of Local Field Potentials for Studying the Function of Cortical Circuits", Nature Reviews Neuroscience, 14(11):770-785.
Emanuel et al. (May 2000) "What Makes Clinical Research Ethical?", JAMA, 283(20):2701-2711.
Engel et al. (Feb. 25, 2003) "Practice Parameter: Temporal Lobe and Localized Neocortical Resections for Epilepsy", Neurology, 60(4):538-547.
Engström et al. (Mar. 27, 2015) "Perception of Control Over Eating After Bariatric Surgery for Super-Obesity—a 2-Year Follow-Up Study", Obesity Surgery, 25:1086-1093.
Finkelstein et al. (2009) "Annual Medical Spending Attributable to Obesity: Payer-and Service-Specific Estimates", Health Affairs, 28(suppl 1):822-831.

(56) References Cited

OTHER PUBLICATIONS

Fisher et al. (May 2010) "Electrical Stimulation of the Anterior Nucleus of Thalamus for Treatment of Refractory Epilepsy", Randomized Controlled Trial, 51(5):899-908.
Fisher et al. (Aug. 2012) "The Ethics of Research on Deep Brain Stimulation for Depression: Decisional Capacity and Therapeutic Misconception", Annals of the New York Academy of Sciences, 1265:69-79 (16 Pages).
Fontaine et al. (Aug. 2001) "Obesity and Health-related Quality of Life", Obesity Reviews, 2(3):173-182.
Fontaine et al. (Jan. 8, 2003) "Years of Life Lost Due to Obesity", JAMA, 289(2):187-193.
Fray et al. (Jul.-Aug. 1996) "CANTAB Battery: Proposed Utility in Neurotoxicology", Neurotoxicology and Teratology, 18(4):499-504.
Ghazizadeh et al. (Jan. 11, 2012) "Prefrontal Cortex Mediates Extinction of Responding by Two Distinct Neural Mechanisms in Accumbens Shell", The Journal of Neuroscience, 32(2):726-737.
Giel et al. (2013) "Eating Disorder Pathology in Adolescents Participating in a Lifestyle Intervention for Obesity: Associations with Weight Change, General Psychopathology and Health-related Quality of Life", Obesity Facts, 6(4):307-316.
Goldschmidt et al. (Jun. 2012) "Momentary Affect Surrounding Loss of Control and Overeating in Obese Adults with and Without Binge Eating Disorder", Obesity (Silver Spring), 20(6):1206-1211 (13 Pages).
Goodman et al. (Mar. 15, 2010) "Deep Brain Stimulation for Intractable Obsessive Compulsive Disorder: Pilot Study Using A Blinded, Staggered-Onset Design", Biological Psychiatry, 67(6):535-542 (17 Pages).
Goodman et al. (Jan. 2005) "Preemptive Low-frequency Stimulation Decreases the Incidence of Amygdala-kindled Seizures", Epilepsia, 46(1):1-7.
Gorin et al. (Dec. 2008) "Binge Eating and Weight Loss Outcomes in Overweight and Obese Individuals with Type 2 Diabetes: Results from the Look Ahead Trial", Archives of General Psychiatry, 65(12):1447-1455 (19 Pages).
Grilo et al. (Oct. 2011) "Cognitive-Behavioral Therapy, Behavioral Weight Loss, and Sequential Treatment for Obese Patients with Binge-eating Disorder: A Randomized Controlled Trial", Journal of Consulting and Clinical Psychology, 79(5):675-685 (19 Pages).
Grilo et al. (Jul. 2001) "Different Methods for Assessing the Features of Eating Disorders in Patients with Binge Eating Disorder: A Replication", Obesity Research, 9(7):418-422.
Groen et al. (Nov. 27, 2015) "Empowerment of Cancer Survivors Through Information Technology: An Integrative Review", Journal of Medical Internet Research, 17(11):e270.
Guh et al. (Mar. 25, 2009) "The Incidence of Co-morbidities Related to Obesity and Overweight: A Systematic Review and Meta-Analysis", BMC Public Health, 9(88):20 Pages.
Gunaydin et al. (Jun. 19, 2014) "Natural Neural Projection Dynamics Underlying Social Behavior", Cell, 157(7):1535-1551.
Haber Suzanne N. (2011) "Neuroanatomy of Reward: A View from the Ventral Striatum", Neurobiology of Sensation and Reward. Boca Raton (FL): CRC Press/Taylor & Francis; 2011. Chapter 11, 28 Pages.
Halperin et al. (Jul. 2014) "Roux-en-Y Gastric Bypass Surgery or Lifestyle with Intensive Medical Management in Patients with Type 2 Diabetes: Feasibility and 1-year Results of a Randomized Clinical Trial", JAMA Surgery, 149(7):716-726 (23 Pages).
Halpern et al. (Aug. 2014) "A Step-Wise Approach to Deep Brain Stimulation in Mice", Acta Neurochirurgica, 156(8):1515-1521.
Halpern et al. (Apr. 24, 2013) "Amelioration of Binge Eating by Nucleus Accumbens Shell Deep Brain Stimulation in Mice Involves D2 Receptor Modulation", The Journal of Neuroscience, 33(17):7122-7129.
Halpern et al. (Aug. 24, 2012) "Deep Brain Stimulation for the Treatment of Binge Eating: Mechanisms and Preclinical Models", Animal Models of Eating Disorders, 74:193-200.
Halpern et al. (2007) "Deep Brain Stimulation in Neurologic Disorders", Parkinsonism & Related Disorders, 13:1-16.
Halpern et al. (Oct. 2008) "Deep Brain Stimulation in the Treatment of Obesity", Journal of Neurosurgery, 109(4):625-634.
Halpern et al. (Dec. 2011) "Expanding Applications of Deep Brain Stimulation: A Potential Therapeutic Role in Obesity and Addiction Management", Acta Neurochirurgica, 153(12):2293-2306.
Hamani et al. (Aug. 2010) "Effects of Different Stimulation Parameters on the Antidepressant-like Response of Medial Prefrontal Cortex Deep Brain Stimulation in Rats", Journal of Psychiatric Research, 44(11):683-687.
Haq et al. (Jan. 2011) "Smile and Laughter Induction and Intraoperative Predictors of Response to Deep Brain Stimulation for Obsessive-Compulsive Disorder", NeuroImage, 54(1): S247-S255.
Heck et al. (Mar. 2014) "Two-Year Seizure Reduction in Adults with Medically Intractable Partial Onset Epilepsy Treated with Responsive Neurostimulation: Final Results of the RNS System Pivotal Trial", Epilepsia, 55(3):432-441.
Hsu et al. (May 1997) "Eating Disturbances and Outcome of Gastric Bypass Surgery: A Pilot Study", International Journal of Eating Disorders, 21(4):385-390.
Hudson et al. (Feb. 1, 2007) "The Prevalence and Correlates of Eating Disorders in the National Comorbidity Survey Replication", Biological Psychiatry, 61(3):348-358.
Jarcho et al. (Mar. 2015) "Neural Activation During Anticipated Peer Evaluation and Laboratory Meal Intake in Overweight Girls with and Without Loss of Control Eating", NeuroImage, 108:343-353.
Johnson et al. (May 2010, e-Published (Mar. 28, 2010)), "Dopamine D2 Receptors in Addiction-like Reward Dysfunction and Compulsive Eating in Obese Rats", Nature Neuroscience, 13(5):635-641 (25 Pages).
Kerrigan et al. (Apr. 2004) "Electrical Stimulation of the Anterior Nucleus of the Thalamus for the Treatment of Intractable Epilepsy", Epilepsia, 45(4):346-354.
Kessler et al. (Jun. 2005) "Lifetime Prevalence and Age-of-onset Distributions of DM-IV Disorders in the National Comorbidity Survey Replication", Archives of General Psychiatry, 62(6):593-602.
Kiernan et al. (Apr. 2012) "Social Support for Healthy Behaviors: Scale Psychometrics and Prediction of Weight Loss Among Women in a Behavioral Program", Obesity (Silver Spring), 20(4):756-764 (18 Pages).
King-Stephens et al. (Jun. 2015) "Lateralization of Mesial Temporal Lobe Epilepsy with Chronic Ambulatory Electrocorticography", Epilepsia, 56(6):959-967.
Knutson et al. (Jul. 2000) "FMRI Visualization of Brain Activity During A Monetary Incentive Delay Task", Neuroimage, 12(1):20-27.
Knutson et al. (Aug. 1, 2014, e-Published (May 13, 2014)), "Inferring affect from fMRI data", Trends in Cognitive Sciences, 18(8):422-428.
Knutson et al. (Mar. 26, 2008) "Nucleus Accumbens Activation Mediates the Influence of Reward Cues on Financial Risk Taking", Neuroreport, 19(5):509-513.
Kombian et al. (Mar. 17, 1994) "Simultaneous LTP of Non-NMDA- and Ltd of NMDA-Receptor-Mediated Responses in the Nucleus Accumbens", Nature, 368(6468):242-246.
Krause et al. (Mar. 31, 2010) "A Pause in Nucleus Accumbens Neuron Firing is Required to Initiate and Maintain Feeding", Journal of Neuroscience, 30(13):4746-4756.
Kroemer et al. (Mar. 2016, e-Published (Mar. 24, 2015)) "Weighing the Evidence: Variance in Brain Responses to Milkshake Receipt is Predictive of Eating Behavior", Neuroimage, 128:273-283.
Kubu et al. (2013) "Neuropsychological Outcome After Deep Brain Stimulation in the Ventral Capsule/Ventral Striatum for Highly Refractory Obsessive-compulsive Disorder or Major Depression", Stereotactic and Functional Neurosurgery, 91(6):374-378.
Lammel et al. (Oct. 14, 2012) "Input-Specific Control of Reward and Aversion in the Ventral Tegmental Area", Nature, 491(7423):212-217.
Lee et al. (Sep. 2011) "A Comparison of the Effect of Epidural Patient-Controlled Analgesia with Intravenous Patient-controlled Analgesia on Pain Control After Posterior Lumbar Instrumented Fusion", Journal of Korean Neurosurgical Society, 50(3):205-208.

(56) References Cited

OTHER PUBLICATIONS

Leong et al. (Jan. 6, 2016) "White-Matter Tract Connecting Anterior Insula to Nucleus Accumbens Correlates with Reduced Preference for Positively Skewed Gambles", Neuron, 89(1):63-69 (16 Pages).

Little et al. (Sep. 2016) "Adaptive Deep Brain Stimulation in Advanced Parkinson Disease", Annals of Neurology, 74(3):449-457.

Liu et al., (Oct. 2015) "Long-term Results on Weight Loss and Diabetes Remission after Laparoscopic Sleeve Gastrectomy for a Morbidly Obese Chinese Population", Obesity Surgery, 25(10):1901-1908.

Loring et al. (Nov. 2015) "Differential Neuropsychological Outcomes Following Targeted Responsive Neurostimulation for Partial-Onset Epilepsy", Epilepsia, 56(11):1836-1844.

Lu et al. (Nov. 13, 2007) "Synchronized Delta Oscillations Correlate with the Resting-state Functional MRI Signal", Proceedings of the National Academy of Sciences of the United States of America, 104(46):18265-18269.

Lucas-Neto et al. (Jul. 2015) "Advanced MR Imaging of the Human Nucleus Accumbens—Additional Guiding Tool for Deep Brain Stimulation", Neuromodulation, 18(5):341-348.

Magri et al. (Jan. 25, 2012) "The Amplitude and Timing of the BOLD Signal Reflects the Relationship between Local Field Potential Power at Different Frequencies", The Journal of Neuroscience, 32(4):1395-1407.

Maling et al. (Sep. 6, 2012) "Increased Thalamic Gamma Band Activity Correlates with Symptom Relief following Deep Brain Stimulation in Humans with Tourette's Syndrome", PLoS One, 7(9):8 Pages.

Mantione et al. (Jan. 2010) "Smoking Cessation and Weight Loss After Chronic Deep Brain Stimulation of the Nucleus Accumbens: Therapeutic and Research Implications: Case Report", Neurosurgery, 66(1):4 Pages.

Martin et al. (Jun. 28, 2004) "Reward Sensitivity in Impulsivity", Neuroreport, 15(9):1519-1522.

McCreery et al. (Oct. 1990) "Charge Density and Charge Per Phase as Cofactors in Neural Injury Induced by Electrical Stimulation", IEEE Transactions on Biomedical Engineering, 37(10):996-1001.

McElroy et al. (Mar. 2015) "Efficacy and Safety of Lisdexamfetamine for Treatment of Adults with Moderate to Severe Binge-eating Disorder: A Randomized Clinical Trial", JAMA Psychiatry, 72(3):235-246.

Meador et al. (Apr. 2015) "Quality of Life and Mood in Patients with Medically Intractable Epilepsy Treated with Targeted Responsive Neurostimulation", Epilepsy & Behavior, 45:242-247.

Miller et al. (Feb. 28, 2007) "Spectral Changes in Cortical Surface Potentials During Motor Movement", The Journal of Neuroscience, 27(9):2424-2432.

Moize et al. (Mar. 2013) "Long-Term Dietary Intake and Nutritional Deficiencies Following Sleeve Gastrectomy or Roux-En-Y Gastric Bypass in a Mediterranean Population", Journal of the Academy of Nutrition and Dietetics, 113(3):400-410.

Morrell et al. (Sep. 27, 2011) "Responsive Cortical Stimulation for the Treatment of Medically Intractable Partial Epilepsy", Neurology, 77(13):1295-1304.

O'Connor et al. (Nov. 4, 2015) "Accumbal D1R Neurons Projecting to Lateral Hypothalamus Authorize Feeding", Neuron, 88(3):553-564.

Ogden et al. (Feb. 26, 2014) "Prevalence of Childhood and Adult Obesity in the United States, 2011-2012", JAMA, 311(8):806-814 (18 Pages).

Ogden et al. (Jan. 2012) "Prevalence of Obesity in the United States", NCHS Data Brief, 82:1-8.

Okun et al. (Jan. 2013) "A Trial of Scheduled Deep Brain Stimulation for Tourette Syndrome: Moving Away from Continuous Deep Brain Stimulation Paradigms", JAMA Neurology, 70(1):85-94.

Ooms et al. (Feb. 2014) "Deep Brain Stimulation for Obsessive-Compulsive Disorders: Long-term Analysis of Quality of Life", Journal of Neurology, Neurosurgery, and Psychiatry, 85(2):153-158.

Pankevich et al. (Dec. 1, 2010) "Caloric Restriction Experience Reprograms Stress and Orexigenic Pathways and Promotes Binge Eating", The Journal of Neuroscience, 30(48):16399-16407.

Pisapia et al. (Aug. 2010) "Deep Brain Stimulation Compared with Bariatric Surgery for the Treatment of Morbid Obesity: A Decision Analysis Study", Neurosurgical Focus, 29(2):1-10.

Puzziferri et al. (Sep. 3, 2012) "Long-Term Follow-up After Bariatric Surgery: A Systematic Review", JAMA, 312(9):934-942 (1-19 Pages).

Quiroga et al. (Aug. 2004) "Unsupervised Spike Detection and Sorting with Wavelets and Superparamagnetic Clustering", Neural Computation, 16(8):1661-1687.

Richard et al. (Jun. 15, 2016) "Ventral Pallidum Neurons Encode Incentive Value and Promote Cue-Elicited Instrumental Actions", Neuron, 90(6):1165-1173 (17 Pages).

Whitmer et al. (Jun. 4, 2012) "High Frequency Deep Brain Stimulation Attenuates Subthalamic and Cortical Rhythms in Parkinson's Disease", Frontiers in Human Neuroscience, 6(155):1-18.

Robinson et al. (Jul.-Aug. 2014) "What Variables are Associated with Successful Weight Loss Outcomes for Bariatric Surgery After One Year?", Surgery for Obesity and Related Diseases, 10(4):697-704 (13 Pages).

Roitman et al. (Feb. 11, 2004) "Dopamine Operates as a Subsecond Modulator of Food Seeking", The Journal of Neuroscience, 24(6):1265-1271.

Rosin et al. (Oct. 20, 2011) "Closed-Loop Deep Brain Stimulation is Superior in Ameliorating Parkinsonism", Neuron, 72(2):370-384.

Sacchet et al. (Feb. 1, 2013, e-Published (Oct. 27, 2012)) "Spatial Smoothing Systematically Biases the Localization of Reward-Related Brain Activity", Neuroimage, 66:270-277 (18 Pages).

Safer et al. (Mar. 2010) "Outcome from a Randomized Controlled Trial of Group Therapy for Binge Eating Disorder: Comparing Dialectical Behavior Therapy Adapted for Binge Eating to an Active Comparison Group Therapy", Behavior Therapy, 41(1):106-120 (21 Pages).

Salanova et al. (Mar. 10, 2015) "Long-Term Efficacy and Safety of Thalamic Stimulation for Drug-resistant Partial Epilepsy", Neurology, 84(10):1017-25.

Schlaepfer et al. (Jan. 2008) "Deep Brain Stimulation to Reward Circuitry Alleviates Anhedonia in Refractory Major Depression", Neuropsychopharmacology, 33(2):368-377.

Schultz et al. (Dec. 1992) "Neuronal Activity in Monkey Ventral Striatum Related to the Expectation of Reward", The Journal of Neuroscience, 12(12):4595-4610.

Siebenhofer et al. (Mar. 2, 2016) "Long- term Effects of Weight-Reducing Drugs in People with Hypertension", Cochrane Database of Systematic Reviews, 2:3 Pages.

Siegel et al. (Jun. 13, 2012) "Sex Differences in Deep Brain Stimulation Amelioration of Binge Eating", Biological Psychiatry, 71: 306S-306S.

Sillay et al. (Mar. 15, 2013) "Long-Term Measurement of Impedance in Chronically Implanted Depth and Subdural Electrodes During Responsive Neurostimulation in Humans", Brain Stimulation, 6(5):718-726.

Smith et al. (Mar. 2016) "Modulation of Impulsivity and Reward Sensitivity in Intertemporal Choice by Striatal and Midbrain Dopamine Synthesis in Healthy Adults", Journal of Neurophysiology, 115(3):1146-1156.

Stenner et al. (Jul. 2015) "Cortical Drive of Low-frequency Oscillations in the Human Nucleus Accumbens During Action Selection", Journal of Neurophysiology, 114(1):29-39.

Stice et al. (Oct. 17, 2008) "Relation Between Obesity and Blunted Striatal Response to Food is Moderated by TaqiA A1 Allele", Science, 322(5900):449-452 (8 Pages).

Strand et al. (Apr. 20, 2007) "Conservation of Regional Gene Expression in Mouse and Human Brain", Plos Genetics, 3(4):0572-0583.

Stunkard et al. (Nov. 1996) "d-fenfluramine Treatment of Binge Eating Disorder", The American Journal of Psychiatry, 153(11):1455-1459.

Tabuchi et al. (Oct. 5, 2007) "A Neuroligin-3 Mutation Implicated in Autism Increases Inhibitory Synaptic Transmission in Mice", Science, 318(5847):71-76 (15 Pages).

(56) References Cited

OTHER PUBLICATIONS

Taha et al. (Jan. 4, 2006) "Inhibitions of Nucleus Accumbens Neurons Encode a Gating Signal for Reward-Directed Behavior", Journal of Neuroscience, 26(1):217-222.

Tanriverdi et al. (Jun. 2009) "Morbidity in Epilepsy Surgery: An Experience Based on 2449 Epilepsy Surgery Procedures from a Single Institution", Journal of Neurosurgery, 110(6):1111-1123.

Teegarden et al. (May 1, 2007) "Decreases in Dietary Preference Produce Increased Emotionality and Risk for Dietary Relapse", Biological Psychiatry, 61(9):1021-1029.

Teegarden et al. (Mar. 2008) "Effects of Stress on Dietary Preference and Intake are Dependent on Access and Stress Sensitivity", Physiology & Behavior, 93(4-5):713-723.

Widge et al. (Apr. 11, 2014, e-Published (Mar. 10, 2014)), "Pre-Frontal Control of Closed-Loop Limbic Neurostimulation by Rodents using a Brain-Computer Interface", Journal of Neural Engineering, 11(2):17 Pages.

Wingeier et al. (Jan. 2006) "Intra-Operative STN DBS Attenuates the Prominent Beta Rhythm in the STN in Parkinson's Disease", Experimental Neurology, 197(1):244-251.

Vidal et al. (Feb. 2014) "Lack of Adherence to Follow-up Visits after Bariatric Surgery: Reasons and Outcome", Obesity Surgery, 24(2):179-183.

Voges et al. (Sep.-Oct. 2013) "Deep Brain Stimulation Surgery for Alcohol Addiction", World Neurosurgery, 80(3-4):S28.e21-31.

Volkow et al. (May 2005) "How Can Drug Addiction Help us Understand Obesity?", Nature Neuroscience, 8(5):555-560.

Wadden et al. (Sep. 17, 2012) "Efficacy of Lifestyle Modification for Long-Term Weight Control", Obesity Research, 12(S12):151S-162S.

Wagenaar et al. (Sep. 30, 2004) "Effective Parameters for Stimulation of Dissociated Cultures Using Multi-Electrode Arrays", Journal of Neuroscience Methods, 138(1-2):27-37.

Wonderlich et al. (Apr. 2015) "Examining Convergence of Retrospective and Ecological Momentary Assessment Measures of Negative Affect and Eating Disorder Behaviors", International Journal of Eating Disorders, 48(3):305-311 (14 Pages).

Weaver et al., (Jan. 7, 2009) "Bilateral Deep Brain Stimulation vs Best Medical Therapy for Patients with Advanced Parkinson Disease", JAMA, 301(1):25 Pages.

Weintraub et al. (May 2010) "Impulse Control Disorders in Parkinson Disease: A Cross-sectional Study of 3090 Patients", Archives of Neurology, 67(5):589-595.

Welch P. (Jun. 1967) "The Use of Fast Fourier Transform for the Estimation of Power Spectra: A Method Based on Time Averaging Over Short, Modified Periodograms", IEEE Transactions on Audio and Electroacoustics, 15(2):70-73.

Weygandt et al. (Dec. 2013) "The Role of Neural Impulse Control Mechanisms for Dietary Success in Obesity", Neurology, 12(83):669-678.

White et al. (Feb. 2010, e-Published (Oct. 20, 2009)), "Loss of Control over Eating Predicts Outcomes in Bariatric Surgery: A Prospective 24-Month Follow-up Study", The Journal of Clinical Psychiatry, 71(2):175-184 (21 Pages).

\* cited by examiner

TREATMENT FOR LOSS OF CONTROL DISORDERS

CROSS-REFERENCES TO RELATED APPLICATIONS

This application is a continuation of U.S. patent application Ser. No. 16/337,315, filed on Mar. 27, 2019, now U.S. Pat. No. 11,642,528 issued on May 9, 2023, which is a National Stage Application filed under 35 U.S.C. § 371 of International Patent Application No. PCT/US17/53820, filed on Sep. 27, 2017, which claims priority to U.S. Provisional Application No. 62/400,483, filed Sep. 27, 2016, which contents are hereby incorporated by reference in their entirety and for all purposes.

STATEMENT AS TO RIGHTS TO INVENTIONS MADE UNDER FEDERALLY SPONSORED RESEARCH AND DEVELOPMENT

This invention was made with government support under Grant Nos. K12NS080223 and UL1 TR001085 awarded by the National Institutes of Health. The government has certain rights in the invention.

BACKGROUND OF THE INVENTION

People with an impulse control disorder cannot resist the urge to do something harmful to themselves or others. Loss of control disorders include substance abuse, sex addiction or compulsive sexuality, kleptomania, pyromania, trichotillomania, panic disorder, Intermittent Explosive Disorder, compulsive behaviors including gambling, binge eating, night eating, loss of control eating, emotional or stress eating, compulsive eating, purge behaviors, suicidal ideation/attempt and other compulsive behaviors.

The biological basis of loss of control disorders is poorly understood. Loss of control disorders are difficult to treat and carry significant medical and psychiatric risks. Pharmacologic interventions have been of limited success and sometimes cause a worsening of binge eating symptoms. A number of psychotropic medications, including but not limited to antidepressants, antipsychotics, antimanic agents, and mood modulating medications are known to cause binge eating, dysregulation of appetite, and weight gain. Binge eating behaviors and weight gain may be a direct effect of such medication(s). Psychotropic medications may also exacerbate an underlying binge eating disorder in some patients.

Predictive signals in the nucleus accumbens (NAc) that are known to begin immediately prior to initiation of an appetitive behavior and continue until completion of that behavior have been detected using single unit recordings. These known predictive signals have yet to be used to optimize a real-time detection system that can release therapeutic stimulation. Accordingly, there is a need in the field for patient specific treatment for impulse control disorders.

BRIEF SUMMARY OF THE INVENTION

The invention is based, at least in part, on the surprising discovery that predictive signalling in the nucleus accumbens can be used in a closed-loop feedback system for the prevention and treatment of impulse control disorders. As such, the systems and methods of the present invention may be particularly valuable for patient specific treatment of impulse control disorders and in particular in the treatment of patient populations that have been resistant to known treatment modalities.

In an aspect, the invention provides a method of detecting low frequency modulations in the nucleus accumbens of a subject, wherein the subject is diagnosed with, or suspected of having, a loss of control or impulse control disorder, the method including: inserting at least one electrode into the nucleus accumbens of the subject and recording brain wave activity in the nucleus accumbens of the subject.

In an aspect, the invention provides an apparatus including: at least (i) one electrode adapted to at least measure brain wave activity in a nucleus accumbens of a subject, wherein the subject is diagnosed with, or suspected of having, a loss of control or impulse control disorder, and to apply an electrical current to the nucleus accumbens of the subject; (ii) a controller configured to at least: detect, based at least in part on the measured brain wave activity, at least one low frequency modulation in the nucleus accumbens of the subject, and administer, in response to the detection of the at least one low frequency modulation, electrical stimulation to the nucleus accumbens of the subject, wherein the administering of electrical stimulation includes applying, by the at least one electrode, the electrical current to the nucleus accumbens of the subject.

In an aspect, the invention provides a system for the treatment of loss of control disorders in a subject in need thereof, the system including: (i) the apparatus as described herein including embodiments thereof, (ii) an optimizer including: at least one processor; and (iii) at least one memory including program code which when executed by the at least one memory provides operations including: receiving treatment data for a first administration of electrical stimulation and a second administration of electrical stimulation, wherein the first administration of electrical stimulation includes an application of electrical current in accordance to a first set of parameters, and wherein the second administration of electrical stimulation includes another application of electrical current in accordance to a second set of parameters; obtaining patient data indicative of a result of the first electrical stimulation and the second electrical stimulation; and adjusting, based at least on the treatment data and the patient data, a third set of parameters for applying electrical current during a subsequent administration of electrical stimulation.

BRIEF DESCRIPTION OF THE DRAWINGS

(FIG. 1A) Mice exhibited increased intake until stabilizing. (FIG. 1B) Stimulation significantly blocked intake on 2 alternate days. (FIG. 1C) Nucleic accumbens (NAc) deep brain stimulation (DBS) suppressed daily food intake when delivered chronically, but there was loss of significance after Day 2. (FIG. 1D) NAc stimulation did not induce a place preference in these mice, suggesting the effects were not reinforcing. (FIG. 1E) Mice provided with a 1-h exposure to the high fat (HF) exhibit episodic binge behavior. (FIG. 1F) Manually triggering stimulation at binge onsets under synchronized video surveillance blocks HF intake with >90% less stimulation-on time. In these figures, "HF" refers to high-fat, DBS refers to "deep brain stimulation" and "*" indicates p<0.05.

(FIG. 2A) 3D schematic of neurostimulator and NAc depths. (FIG. 2B) Depth contacts superimposed and to-scale on the NAc derived from the Schaltenbrand and Wahren Atlas as referenced in 44. (FIG. 2C) Close-up with dimensions. In FIGS. 2A-2C, "Cd" refers to "caudate", "Put" refers to "putamen", "NAc" refers to "nucleus accumbens", and "ALIC" refers to "anterior limb of the internal capsule".

(FIG. 3A) Continuous time-frequency spectrogram indicating increased power in low frequency oscillations prior to binge onset (dashed white line) using an off-the-shelf system. (FIG. 3B) The corresponding power spectrogram (top) and Local Field Potentials (LFPs) (bottom) recorded by integrated responsive neurostimulation (RNS®) revealing similar changes in a different mouse during binge period (boxed area). This change in LFPs (in the delta band specifically) was detected by a predefined biomarker detector, indicated by marker "A2", and subsequently has been used for responsive neurostimulation (see FIGS. 4A-4B). (FIGS. 3C-3F) These spectrograms and LFPs represent data recorded immediately before and during chow intake onset (dotted white line and box) and social interaction onset (dotted white line and box), none of which revealed such a robust delta power fluctuation and no RNS® detections occurred.

(FIG. 4A) Scheduled stimulation (10 s on 20 s off) blocked intake but was only significant when stimulation was delivered in response to a detection of delta power change (closed-loop, RNS®). (FIG. 4B) Using the same biomarker for responsive stimulation, social interaction with a juvenile mouse was not altered. In these figures, "RNS-Sch" refers to "scheduled stimulation", "RNS" refers to "responsive stimulation", and "*" indicates p<0.05.

(FIG. 5A) Volume of interest (ventral striatum) in representative OCD subject. (FIG. 5B) Gain (a gain of $5.00) versus nongain (a gain of $0.00) anticipation contrast with significant NAc BOLD signal (p<0.005). (FIG. 5C and FIG. 5D) Continuous time-frequency spectrograms show increased power (proportional to gain magnitude) in low frequency oscillations during same anticipation phase in same patient using depth leads identical to RNS® leads. (FIG. 5E) To test the RNS® System's ability to detect such LFP changes, the LFPs were played back through a benchtop system. The neurostimulator was programmed to detect power increases in low frequency activity and detected the increase in low frequency power on channel 3-4 (dashed outline boxes). Further adjustments of the RNS® System detection parameters resulted in earlier detections (solid outline boxes). In these figures, "NAc" refers to "nucleus accumbens".

(FIG. 9A) Schematic of the experimental design: Electrode implantation, followed by recovery period (7 days), limited HF access (day 0-18), and intervention period (day 11-18). (FIGS. 9B-9D) Histology examination revealing the implant locations, and design of the 8-contact multielectrode array, which had 6 designated recording contacts (boxes with gray star) and 2 designated stimulating contacts (boxes without gray star). (FIGS. 9E-9G) Binge-like behavior developed and stabilized by day 10 of limited HF exposure (1 h/day), indicated by significant increase in daily HF intake with >25% of daily caloric intake in 1 hour. In these figures, "*" indicates P<0.05.

(FIGS. 10A-10C) Raw LFP samples are shown during the onset (dotted grey line) of house chow as a control and high-fat (HF) consumption on days 0 and 10 (before and after the development of binge-like behavior, respectively). (FIGS. 10D-10F) Mean power spectrogram of NAc LFPs immediately before and after the onset of chow and HF consumption on days 0 and 10. (FIG. 10G) Power spectral density analysis of NAc LFPs immediately before (2-second window) chow and HF intake on days 0 and 10, averaged across individual mice, revealing higher power in low-frequency oscillations immediately prior to the onset of HF intake on day 10. (FIG. 10H) Mean delta power significantly increased immediately prior to the onset of HF intake on day 10 compared to HF intake on day 0 and chow intake. (FIG. 10I) Delta power percent-change-over-baseline during the onset of HF consumption on day 10 (normalized to the 1-hr period of HF exposure). (FIG. 10J) Delta power peak distribution before the onset HF consumption on day 10. (FIG. 10K) Mean power spectrogram of NAc LFP during the onset of juvenile interaction. (FIG. 10L) System block diagram of the responsive neurostimulation setup, which consisted of a 1× follower cable for unit amplification, a headstage for analog/digital conversion, a digital filter, a computer for synchronizing neural electrophysiological and behavioral data, a prototype biomarker detector (Neurostimulator, Model RNS®-300, NeuroPace, Mountain View, CA, USA), a constant-current stimulator, and a charge-coupled device camera for synchronized behavioral recording. In these figures, "**" indicates P<0.01. See also FIG. 14.

(FIG. 11A) Representative nucleus accumbens (NAc) local field potential delta oscillations (solid outline boxed region) at the onset of HF intake detected by the integrated responsive neurostimulation (RNS®) system. (FIG. 11B) Schematic of the intervention period. Each intervention session (deep brain stimulation (DBS), manually-triggered stimulation (Man), responsive neurostimulation (RNS®), randomly-applied stimulation (Rnd)) was followed by one washout session (Off). (FIGS. 11C-11F) The effects of different stimulation protocols on HF consumption. DBS, Man, and RNS® significantly reduced HF intake. (FIG. 11G) Reduction in HF intake induced by DBS, manually-triggered stimulation, RNS®, and randomly-applied stimulation, compared to off stimulation. The reduction in HF intake induced by the manually-triggered stimulation and RNS® was significantly higher than randomly-applied stimulation. (FIG. 11H) The number of stimulations bouts (1 bout=10 s) delivered during Man and RNS® were significantly lower than DBS. (FIG. 11I) DBS of the NAc significantly reduced juvenile interaction time, while RNS® showed no effect on this behavior. (FIG. 11J) Neither DBS nor RNS® of the NAc during HF exposure altered locomotor activity. (FIG. 11K) Real-time place preference test suggested that NAc stimulation was neither rewarding nor aversive. (FIG. 11L-11M) Sensitivity and specificity of delta biomarker on RNS® day in all 6 mice. In total there were 179 HF pellet approaches, of which 124 were detected by the RNS® system (sensitivity=0.693). There were also 1241 correct rejections (stimulation off when no HF approach occurred) and 685 stimulations triggered when no HF approaches were observed (false stimulation; specificity=0.644). In these figures, "*" indicates P<0.05, "" indicates P<0.01, and "*" indicates P<0.001. See also FIGS. 15A-15B.

(FIG. 12A) Identification, principal component (PC) analysis, and average waveforms of NAc neurons recorded on day 10 during high-fat intake. (FIG. 12B) Raster plot of NAc firing represented for each trial under different conditions. (FIG. 12C) NAc spike rate on day 10 during high-fat intake was significantly higher than chow and day 0 high-fat intake. (FIG. 12D) Representative example of NAc local field potentials (bottom) and unit activities (top), showing phase synchrony with low-frequency oscillations. (FIG. 12E) Delta spike-field coherence revealed that the coherence on day 10 during high-fat intake was significantly higher than chow and day 0 high-fat intake. (FIG. 12F) NAc spike rate significantly correlated with delta power on day 10 during high-fat intake. In these figures, "NAc" refers to "nucleus accumbens", "#" indicates P<0.1, "*" indicates P<0.05, "" indicates P<0.01, and "**" indicates P<0.0001.

FIGS. 13A-13L Schematic of Functional Neuroimaging and Local Field Potentials (LFPs) Recording during the Monetary Incentive Delay (MID) task in Human Subject. (FIG. 13A) Schematic of the MID task, which consists of cue onset, anticipation phase, target onset, and outcome phase. (FIG. 13B) Functional magnetic resonance imaging (fMRI) showing area activated by gain versus nongain anticipation in the nucleus accumbens (NAc) (white circle; Z>2.54, cluster=4 3 mm cubic voxels). (FIG. 13C) Blood-oxygen level dependent (BOLD) signal changes during MID task extracted from activated voxels in the left NAc averaged by condition, indicating NAc activation during high reward anticipation compared to baseline (high reward: baseline, T(17)=3.23, P<0.01, uncorrected; low reward: baseline, high punishment:baseline, low punishment:baseline, n.s.). (FIG. 13D) Electrode contact locations in the NAc for LFP recording using preoperative 7 T MRI merged with postoperative computed tomography scan. Coronal view (trajectory view not shown) demonstrates most posterior aspect of electrode trajectory. (FIGS. 13E-13F) Raw LFPs during baseline and anticipation of high reward. (FIGS. 13G-13H) Power density analysis revealing significant increase in delta power during anticipation of high reward compared to baseline. (FIG. 13I) Normalized NAc LFP power spectrogram (averaged across individual trials), indicating increased delta band (1-4 Hz) power during anticipation of high reward (insets: frequency range from 0-50 Hz). In these figures, "**" indicates P<0.01. See also FIGS. 16A-16B.

(FIG. 15A) Repeated RNS® confirmed its efficacy to significantly reduce HF intake. In this figure, "**" indicates p<0.01. (FIG. 15B) The effects of NAc stimulation on chow consumption, which did not have any measurable effect over 24 h.

(FIG. 16A) Recordings of head movement during MID task in functional magnetic resonance imaging study (less than 1.5 mm over 15 minutes). (FIG. 16B) Representative local field potential powerspectrogram (top), and head movement (middle, measured in acceleration (V)), and limb movement accelerometer traces (bottom, measured in angular velocity (deg/s)) during intraoperative MID task. Very little movement was detected except in right limb when the test subject pressed a button (black arrow).

(FIG. 18A) Microelectrode recording site in the ventral nucleus accumbens. (FIG. 18B) Average spike. (FIG. 18C) First 3 eigenvectors of PCA decomposition. (FIG. 18D) First 10 eigenvalues. Inset—Projection weights of 1st 2 eigenvalues, without obvious clustering of more than one spike, suggesting that spikes correspond to a single neuron. (FIG. 18E) Spike-field coupling palette—mean spike rate (indicated by shade of gray) as a function of frequency and phase of Morlet-wavelet derived instantaneous Fourier phase. Note the selective phase-locking of spikes to the peak (phase 0) of the 2-3 Hz signal. (FIG. 18F) For each task block, a vector indicated the spike-field coupling (with preferred phase revealed by the angle in the complex plane) is calculated and indicated with a dot (Dark gray dots indicate fixation blocks, Light gray dots indicate inter-trial interval (ITI) blocks). This represents the single-trial spike-field coupling, and also the preferred phase of coupling. If there were no significant coupling (e.g. non-zero and reproducible preferred phase of coupling), dot clouds would be symmetrically distributed about the origin. (FIG. 18G) For fixation blocks at each valence, each complex-valued vector in (FIG. 18F) is projected into the average phase of coupling. This produces distributions of coupling, with means and error bars (SEM) to indicate significance vs each other and vs zero. When compared with ITI (light gray), it appears that there is a suppression of spike-field coupling with increasing absolute reward valence (whether positive +1/+5 or negative −1/−5).

DETAILED DESCRIPTION OF THE INVENTION

Figure 1A:
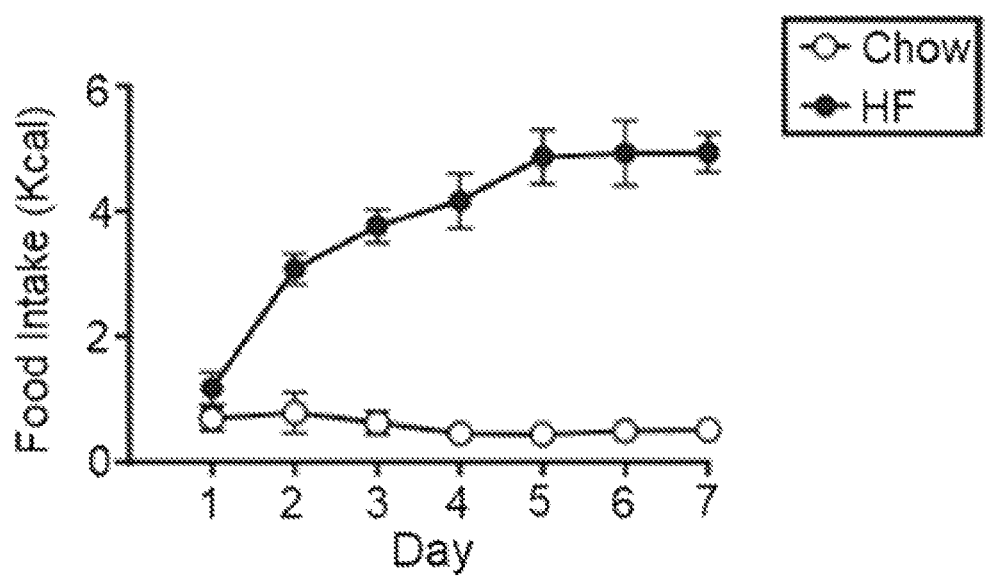
FIGS. 1A-1F.
Figure 1B:
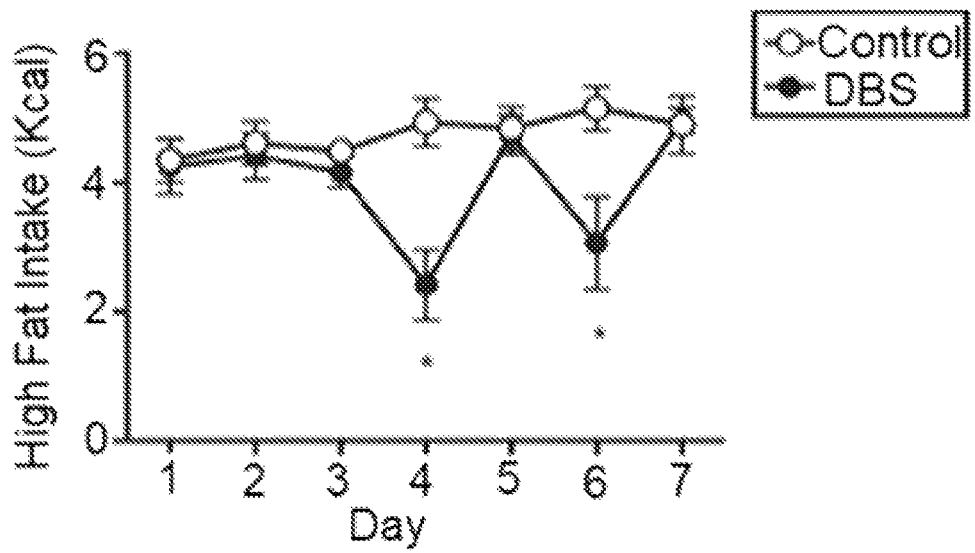

Binge eating can be attenuated in mice with deep brain stimulation (DBS) of the nucleus accumbens as described by Halpern et al, 2013. Translating these findings to humans requires a stimulator to automatically stimulate when subjects begin to binge. Applicants have successfully developed a closed-loop system, detecting an electrophysiologic signal that predicts appetitive behaviors needs and identified a range of electrical stimulations in a closed-loop DBS setting. The target patients for these translation studies are known to be non-compliant to any treatment approach, thus a trigger, independent of patient control, is required for DBS to be initiated reliably. The pause neurons are a subset of accumbens neurons found to exhibit long-lasting inhibitions in firing rate before initiation of goal-directed behaviors, and thus is the prime candidate for optimizing closed-loop DBS. Notably, inhibitions in accumbens activity have also been identified in humans anticipating monetary rewards, emphasizing the importance of this pause in initiating and maintaining motivated behaviors across species.

The present invention provides, inter alia, methods, apparatus, and systems useful for ameliorating impulse control disorders known to be extremely disabling and common to many neurological and psychiatric conditions using closed-loop (responsive) neurostimulation. The present invention uses, inter alia, electrical stimulations used for deep brain stimulation (DBS) in a closed-loop (responsive) setting.

Definitions

The terms "disorder" or "disease" as provided herein are used interchangeably and refer to any deviation from the normal health of a mammal and include a state when disease/disorder symptoms are present, as well as conditions in which a deviation (e.g., chemical imbalance, infection, gene mutation, genetic defect, etc.) has occurred, but symptoms are not yet manifested or are not yet fully manifested. According to the present invention, the methods disclosed herein are suitable for use in a patient that is a member of the Vertebrate class, Mammalia, including, without limitation, primates, livestock and domestic pets (e.g., a companion animal). Typically, a patient will be a human patient.

"Patient" or "subject in need thereof" refers to a living organism suffering from or prone to a disease, disorder, or condition that can be treated by administration of electrical stimulation as provided herein, including embodiments thereof. Non-limiting examples include humans, other mammals, bovines, rats, mice, dogs, monkeys, goat, sheep, cows, deer, and other non-mammalian animals. In embodiments, a patient is human.

The term "loss of control disorder" or "impulse control disorder" as used herein refers to a disordered pattern of behavior characterized by diminished impulse control or compulsions. Loss of control (LOC) disorders include substance abuse, sex addiction or compulsive sexuality, kleptomania, pyromania, trichotillomania, panic disorder, Intermittent Explosive Disorder, compulsive behaviors including gambling, binge eating, night eating, loss of control eating, emotional or stress eating, compulsive eating, purge behaviors, suicidal ideation/attempt and other compulsive behaviors.

Substance abuse refers to compulsive, pathological use of drugs and/or alcohol, including an inability to reduce or prevent consumption. Substance abuse may additionally include impairment in social or occupational functioning as result of substance abuse.

Sex addiction refers to compulsive engagement in sexual activities (e.g., sexual intercourse) despite negative consequences (e.g., negative effects on health, work performance, relationships, or other parts of life).

Compulsive sexuality, also referred to as compulsive sexual behavior, refers to an obsession with sexual thoughts, urges, or behaviors that cause distress and negatively impact or disrupt health, work performance, relationships, or other parts of one's life.

Kleptomania is an impulse control disorder wherein an individual experiences a recurrent urge, and an inability to resist the urge, to steal items which are not needed or have little value. Kleptomania can cause severe emotional pain to the subject and negatively impact relationships.

Pyromania is an impulse control disorder wherein an individual experiences an irresistible impulse to start fires or set fire to objects.

Trichotillomania is an impulse control disorder characterized by a long term urge to pull out one's own hair. Trichotillomania may result in noticeable hair loss. Trichotillomania may also fall within the spectrum of obsessive compulsive disorders.

Panic disorder refers to a type of anxiety disorder wherein an individual experiences recurrent and often unexpected panic attacks. Panic attacks may include heart palpitations or accelerated heart rate, sweating, trembling, sensation of shortness of breath, chest pain or discomfort, nausea or abdominal distress, dizziness, feelings of unreality, fear of losing control, fear of dying, numbness or tingling sensations, and/or chills or hot flushes. An individual suffering from panic disorder may fear the onset of a panic attack, resulting in a change in the person's behavior in an effort to avoid triggering a panic attack.

Intermittent Explosive Disorder (IED) refers to a type of behavioral disorder characterized by explosive outburst of anger and/or violence that are disproportionate to a situation.

Compulsive behaviors contemplated herein include, but are not limited to, gambling characterized by an uncontrollable urge to continue gambling despite negative consequences; eating disorders, such as binge eating which is characterized by recurrent episodes of eating large quantities of food quickly and to the point of discomfort, which may be followed by feelings of depression, disgust, or guilt; night eating which is characterized by a delayed circadian pattern of food intake often accompanied by a sense of shame and/or inability to control one's eating pattern; loss of control eating which is characterized by a sense of loss of control over eating similar to that experienced in binge eating, but not necessarily accompanied by consumption of a large quantity of food; emotional or stress eating which is eating in an effort to alleviate negative emotions; compulsive eating which refers to a compulsion to overeat resulting in consumption of abnormally large quantities of food while simultaneously feeling unable to stop consumption; purge behaviors, for example self-induced vomiting, misuse of laxatives, excessive exercise; suicidal thoughts, also known as suicidal ideation, wherein an individual may consider or formulate plans to kill oneself; and suicidal attempts wherein an individual will engage in a non-fatal, self-directed injurious behavior with the intent of killing oneself.

LOC over eating is common to all binge eaters, and is known to predict poor weight loss following gastric bypass surgery.[15,31] While this behavior is undoubtedly multifactorial, one of the most obvious environmental factors is the societal overabundance of high-energy, highly refined foods.[97] The reinforcing properties of such food are thought to be mediated by the NAc, a striatal brain region known to be central to regulating the selection of goal-directed actions.[56,88]

Commonly described symptoms of binge eating disorder include frequent dieting and weight loss, hoarding of food, hiding empty food containers, eating late at night, attribution of one's successes and failures to weight, avoiding social situations where food may be present, and feeling depressed or anxious. Binge eating also may cause rapid and unhealthy weight gain (or loss), weight fluctuations, and chronic erratic eating behavior. Binge eating disorder and symptoms associated with binge eating disorder may result in obesity though obesity is not necessarily a result of binge eating disorder. Further, patients with binge eating disorder are often not obese and may even have a below normal weight.

The term "nucleus accumbens" as used herein refers to a region in the basal forebrain rostral to the preoptic area of the hypothalamus. The nucleus accumbens is known to play a role in brain reward circuitry.

The term "brain wave activity" as provided herein refers to a repetitive and/or rhythmic neural activity produced by the central nervous system. Brain wave activity can be detected, for example, through the use of an electrode positioned within brain tissue such that the electrode senses voltage fluctuations driven by neural activity. The structure of voltage fluctuations in brain tissue gives rise to oscillatory activity that can be parsed into different frequencies and/or different frequency bands, wherein each frequency band includes a range of frequencies (e.g., delta band including from about 1 Hz to about 4 Hz). "Low frequency" as provided herein refers to brain wave activity including frequencies within a frequency band spanning between 0 Hz to about 38 Hz.

Non-limiting examples of methods for characterizing brain wave activity include power spectral analyses and cross-frequency coupling measures. Power spectral analysis quantifies the power in each frequency or frequency band per unit time. This analysis allows the power in a particular frequency or frequency band (e.g., low frequency) at a given time (e.g., during or immediately prior to manifestation of a disorder symptom) to be compared against the power in the same frequency or frequency band (e.g., low frequency) at a different period in time (e.g., in the absence of a disorder symptom manifestation), thereby allowing detection of power modulations. Alternatively, changes in power in each frequency band may be visually displayed over time by plotting a spectrogram, thereby allowing detection of changes (e.g., modulations) in power in frequencies or frequency bands of interest (e.g., low frequency) to be analyzed over time (e.g., across time periods including or immediately preceding a symptom manifestation, as well as symptom free time periods.).

Cross-frequency coupling measures may be used to describe statistical relationships between frequencies. For example, the phase of low frequency brain wave activity and power of higher frequency (i.e., frequencies faster than those included in low frequency) brain wave activity may have a statistical dependence. Cross-frequency coupling can be assessed at different time points to determine if the statistical dependence of frequencies or frequency bands is modulated by certain conditions (e.g., symptom manifestation).

Brain wave activity may also be related to the activity of individual neurons. A non-limiting example of characterizing the relationship of individual neural activity with brain wave activity is known as spike-field coherence or spike-field coupling. Spike-field coherence quantifies the propensity of action potentials (i.e., spikes) from a given neuron or group of neurons to align with a particular phase of a given frequency of brain wave activity (e.g., low frequency). Spike-field coherence can be assessed at different time points (e.g., periods preceding or concurrent with symptom manifestation and periods temporally distinct from symptom manifestations) such that modulations in spike-field coherence can be determined in response to certain conditions (e.g., symptom manifestation).

The term "modulate" is used in accordance with its plain ordinary meaning and refers to the act of changing or varying one or more properties. "Modulation" refers to the process of changing or varying one or more properties (e.g., power, cross-frequency coupling, spike-field-coherence). A modulation may be determined by comparing a test sample to a control sample or value.

A "control" sample or value refers to a sample that serves as a reference or baseline, usually a known reference, for comparison to a test sample. For example, a test sample (e.g., low frequency brain wave activity) can be taken from a patient suffering from a LOC disorder during a time period immediately preceding or concurrent with a disorder symptom manifestation (e.g., binge eating) and compared to a sample from the same patient during a period temporally distinct from a symptom manifestation. A control value can be obtained from the same individual, e.g., from an earlier-obtained sample, prior to disease, or prior to treatment. One of skill will recognize that controls can be designed for assessment of any number of parameters.

"Low frequency modulation" as provided herein refers to a change in low frequency brain wave activity (e.g., a change in frequencies between 0 to about 38 Hz) compared to a control. A control may be a baseline low frequency brain wave activity. In embodiments, the baseline low frequency brain wave activity is defined as a time period which is different (longer or shorter (e.g., greater or smaller than 2 seconds)) from the time of manifestation of a disorder symptom. In embodiments, the baseline low frequency brain wave activity is defined as a brain wave frequency different from the frequency characteristic for the manifestation of a disorder symptom. Detection of a low frequency modulation may include methods for characterizing low frequency brain wave activity as described above. Thus, in embodiments, a low frequency modulation is a change in low frequency power relative to a baseline low frequency power. In embodiments, a low frequency modulation is an increase in low frequency power compared to baseline low frequency power. In embodiments, a low frequency modulation is an about 10% to about 45% increase in low frequency power compared to baseline low frequency power. In embodiments, a low frequency modulation is a 10% to 45% increase in low frequency power compared to baseline low frequency power. In embodiments, a low frequency modulation is an about 10% increase in low frequency power compared to baseline low frequency power. In embodiments, a low frequency modulation is a 10% increase in low frequency power compared to baseline low frequency power. In embodiments, a low frequency modulation is an about 15% increase in low frequency power compared to baseline low frequency power. In embodiments, a low frequency modulation is a 15% increase in low frequency power compared to baseline low frequency power. In embodiments, a low frequency modulation is an about 20% increase in low frequency power compared to baseline low frequency power. In embodiments, a low frequency modulation is a 20% increase in low frequency power compared to baseline low frequency power. In embodiments, a low frequency modulation is an about 25% increase in low frequency power compared to baseline low frequency power. In embodiments, a low frequency modulation is a 25% increase in low frequency power compared to baseline low frequency power. In embodiments, a low frequency modulation is an about 30% increase in low frequency power compared to baseline low frequency power. In embodiments, a low frequency modulation is a 30% increase in low frequency power compared to baseline low frequency power. In embodiments, a low frequency modulation is an about 35% increase in low frequency power compared to baseline low frequency power. In embodiments, a low frequency modulation is a 35% increase in low frequency power compared to baseline low frequency power. In embodiments, a low frequency modulation is an about 40% increase in low frequency power compared to baseline low frequency power. In embodiments, a low frequency modulation is a 40% increase in low frequency power compared to baseline low frequency power. In embodiments, a low frequency modulation is an about 45% increase in low frequency power compared to baseline low frequency power. In embodiments, a low frequency modulation is a 45% increase in low frequency power compared to baseline low frequency power.

In embodiments, a low frequency modulation includes a modulation in cross-frequency coupling between low frequency brain wave activity and higher frequency brain wave activity.

In embodiments, a low frequency modulation is a modulation in low frequency spike-field coherence. In embodiments, a low frequency modulation is an increase in low frequency spike-field coherence.

In embodiments, a low frequency modulation precedes the onset of a disorder symptom manifestation. In embodiments, a low frequency modulation precedes the onset of a disorder symptom manifestation by about 2 seconds. In embodiments, a low frequency modulation precedes the onset of a disorder symptom manifestation by 2 seconds. In embodiments, a low frequency modulation precedes the onset of a disorder symptom manifestation by about 1.5 seconds. In embodiments, a low frequency modulation precedes the onset of a disorder symptom manifestation by 1.5 seconds. In embodiments, a low frequency modulation precedes the onset of a disorder symptom manifestation by about 1 second. In embodiments, a low frequency modulation precedes the onset of a disorder symptom manifestation by 1 second. In embodiments, a low frequency modulation precedes the onset of a disorder symptom manifestation by about 0.5 seconds. In embodiments, a low frequency modulation precedes the onset of a disorder symptom manifestation by 0.5 seconds. In embodiments, a low frequency modulation precedes the onset of a disorder symptom manifestation by about 0.1 seconds. In embodiments, a low frequency modulation precedes the onset of a disorder symptom manifestation by 0.1 seconds. Thus, the low frequency modulation is predictive of a disease symptom manifestation (e.g., binge eating). In embodiments, the low frequency modulation is a biomarker.

A "biomarker" as provided herein refers to any assayable characteristics or compositions that are used to identify, predict, or monitor a condition (e.g., symptom of an LOC disorder) or a therapy for said condition in a subject or sample. A biomarker is, for example, a brain wave activity pattern (e.g., low frequency modulation) whose presence is used to identify a condition (e.g. a LOC disorder) or status of a condition (e.g. onset of a disorder symptom manifestation) in a subject or sample. Biomarkers identified herein are measured to determine the onset of disease symptoms and to serve as a trigger for delivering (e.g., administering) a therapeutic stimulation (i.e., electrical stimulation).

The term "electrical stimulation" as used herein refers to an electromagnetic energy administered to the brain in a precise location using an electrode, wherein said electromagnetic energy is capable of modulating an electrical impulse in the brain (e.g., reducing low frequency power in brain region). The electromagnetic energy may be administered at specific parameters which include, for example, frequency, time (burst duration), duty cycle and repetition or any combination thereof. The term "burst duration" as used herein refers to the length of time during which the electrical impulses at a given frequency are administered. Likewise, a "burst" as referred to herein corresponds to the electrical impulse administered at a given frequency. A "duty cycle" as used herein refers to the number and sequence of burst durations (e.g., time-on) followed by the time wherein no burst is administered (e.g., time-off).

The terms "dose" and "dosage" are used interchangeably herein and are defined by the specific parameters of administering an electrical stimulation. Therefore, a dose as provided herein refers to an electrical stimulus administered at a given frequency, burst duration, duty cycle, repetition or any combination thereof. The dose will vary depending on a number of factors, including the range of normal doses for a given therapy; frequency of administration; size and tolerance of the individual; severity of the condition; and risk of side effects. One of skill will recognize that the dose can be modified depending on the above factors or based on therapeutic progress. In the present invention, the dose may undergo multiple iterations in order to optimize a therapeutic effect.

As used herein, the terms "treat" and "prevent" are not intended to be absolute terms. Treatment can refer to any delay in onset, reduction in the frequency or severity of symptoms, amelioration of symptoms, and/or improvement in patient comfort (e.g., quality of life), etc. The effect of treatment can be compared to the same patient prior to, or after cessation of, treatment.

"Treating" or "treatment" as used herein (and as well-understood in the art) also broadly includes any approach for obtaining beneficial or desired results in a subject's condition, including clinical results. Beneficial or desired clinical results can include, but are not limited to, alleviation or amelioration of one or more symptoms or conditions, diminishment of the extent of a disease, stabilizing (i.e., not worsening) the state of disease, prevention of a disease's transmission or spread, delay or slowing of disease progression, amelioration or palliation of the disease state, diminishment of the reoccurrence of disease, and remission, whether partial or total and whether detectable or undetectable. In other words, "treatment" as used herein includes any cure, amelioration, or prevention of a disorder. Treatment may prevent the disorder from occurring; relieve the disorder's symptoms, fully or partially remove the disorder's underlying cause, shorten a disorder's symptom duration, or do a combination of these things.

"Treating" and "treatment" as used herein include prophylactic treatment. Treatment methods include administering to a subject a therapeutically effective amount of an active agent (i.e., electrical stimulation). The administering step may consist of a single administration or may include a series of administrations. The length of the treatment period depends on a variety of factors, such as the severity of the condition, the age of the patient, the concentration of active agent (e.g., electrical stimulation), the activity of the compositions used in the treatment, or a combination thereof. It will also be appreciated that the effective dosage of an agent used for the treatment or prophylaxis may increase or decrease over the course of a particular treatment or prophylaxis regime. Changes in dosage may result and become apparent by standard diagnostic assays known in the art. In some instances, chronic administration may be required. For example, electrical stimulations are administered to the subject in an amount and for a duration sufficient to treat the patient.

The term "prevent" refers to a decrease in the occurrence of LOC-associated disorder symptoms in a patient. As indicated above, the prevention may be complete (no detectable symptoms) or partial, such that fewer symptoms are observed than would likely occur absent treatment.

The term "therapeutically effective amount," as used herein, refers to the amount or dose of a therapeutic agent (i.e., electrical stimulation) sufficient to ameliorate the disorder, as described above. For example, for the given dose, a therapeutically effective amount will show an increase of at least 5%, 10%, 15%, 20%, 25%, 40%, 50%, 60%, 75%, 80%, 90%, or at least 100%. Therapeutic efficacy can also be expressed as "-fold" increase or decrease. For example, a therapeutically effective amount can have at least a 1.2-fold, 1.5-fold, 2-fold, 5-fold, or more effect over a control.

The term "administering" as provided herein, refers to the delivery of an electrical stimulation via one or more electrodes positioned within a specific brain structure (e.g., NAc). In the present invention, administration is commenced following detection of a biomarker (e.g., low frequency modulation). In embodiments, administration is accomplished by the apparatus and system provided herein, including embodiments thereof. The same device used to administer electrical stimulation can be used to record brain wave activity to detect a disorder biomarker. In embodiments, administration is triggered automatically by detection of a biomarker (e.g., low frequency modulation). This method of biomarker detection followed by automatic electrical stimulation administration may be referred to herein as "closed-loop" neurostimulation or responsive neurostimulation (RNS®). This form of stimulation differs from deep brain stimulation (DBS) in that deep brain stimulation is not a closed-loop system, but rather sends chronic and continuous electrical impulses through the implanted electrodes to specific brain targets. Thus, DBS may be referred to herein as an "open-loop" type of therapeutic treatment, because it involves continuous electrical stimulation that is not preceded by detection of or triggered by specific biomarkers. Where a dose provided herein is compared to a dose administered in DBS, the dose is generally compared to a dose in an open-loop type system.

Method

Provided herein are, inter alia, methods for detecting biomarkers in the nucleus accumbens (NAc) indicative of the onset of a loss of control (LOC) or impulse control disorder symptom and delivering an electrical stimulation to ameliorate or prevent the symptom from occurring. Thus, in an aspect is provided a method of detecting low frequency modulations in the nucleus accumbens of a subject, wherein the subject is diagnosed with, or suspected of having, a loss of control or impulse control disorder, the method including: inserting at least one electrode into the nucleus accumbens of the subject; and recording brain wave activity in the nucleus accumbens of the subject. Low frequency modulations may include, without limitation, any of the modulations as described above.

In embodiments, at least 2 electrodes are inserted into the nucleus accumbens. In embodiments, at least 3 electrodes are inserted into the nucleus accumbens. In embodiments, at least 4 electrodes are inserted into the nucleus accumbens. In embodiments, at least 5 electrodes are inserted into the nucleus accumbens. In embodiments, at least 6 electrodes are inserted into the nucleus accumbens. In embodiments, at least 7 electrodes are inserted into the nucleus accumbens. In embodiments, at least 8 electrodes are inserted into the nucleus accumbens.

In embodiments, electrodes may be inserted unilaterally into a nucleus accumbens of the subject. In embodiments, electrodes may be inserted bilaterally into the nucleus accumbens of the subject.

In embodiments, the at least one electrode is a deep brain electrode. A deep brain electrode as used herein refers to an electrode capable of targeting a deep brain structure (e.g., NAc).

In embodiments, the loss of control disorder includes a disorder that is associated with a lack of impulse control, and wherein the loss of control disorder includes one or more of substance abuse, sex addiction or compulsive sexuality, kleptomania, pyromania, trichotillomania, panic disorder, Intermittent Explosive Disorder, compulsive behaviors including gambling, binge eating, night eating, loss of control eating, emotional or stress eating, compulsive eating, purge behaviors, or suicidal ideation/attempt. In embodiments, the loss of control disorder includes substance abuse. In embodiments, the loss of control disorder includes sex addiction. In embodiments, the loss of control disorder includes compulsive sexuality. In embodiments, the loss of control disorder includes kleptomania. In embodiments, the loss of control disorder includes pyromania. In embodiments, the loss of control disorder includes trichotillomania. In embodiments, the loss of control disorder includes panic disorder. In embodiments, the loss of control disorder includes Intermittent Explosive Disorder. In embodiments, the loss of control disorder includes compulsive behaviors. In embodiments, the compulsive behavior is gambling. In embodiments, the compulsive behavior is binge eating. In embodiments, the compulsive behavior is night eating. In embodiments, the compulsive behavior is loss of control eating. In embodiments, the compulsive behavior is emotional eating. In embodiments, the compulsive behavior is stress eating. In embodiments, the compulsive behavior is compulsive eating. In embodiments, the compulsive behavior is a purge behavior. In embodiments, the compulsive behavior is suicidal ideation. In embodiments, the compulsive behavior is suicidal attempt.

In the present invention, detection of a biomarker (e.g., low frequency modulation) results in administration of an electrical stimulus to ameliorate or prevent manifestation of a LOC symptom. Therefore, in embodiments, the method further includes administering, in response to detecting the biomarker (e.g., a low frequency modulation), an electrical stimulation to the nucleus accumbens of the subject.

Both the recording of brain wave activity and delivery of the electrical stimulation occur via the one or more electrodes positioned within the nucleus accumbens. In embodiments, an electrode records brain wave activity and delivers an electrical stimulation. In embodiments, a subset of electrodes record brain wave activity and a different subset of electrodes deliver electrical stimulation. In embodiments, a subset of electrodes record brain wave activity and deliver electrical stimulation and a different subset of electrodes record brain wave activity. In embodiments, a subset of electrodes record brain wave activity and deliver electrical stimulation and a different subset of electrodes deliver electrical stimulation. It will be obvious to one skilled in the art that numerous electrode configurations may be used to record brain wave activity and deliver electrical stimulations.

The electrical stimulation (e.g., dosage) administered can vary in frequency, burst duration, duty cycle, repetition, etc. In embodiments, a dose of the electrical stimulation is less than a dose corresponding to deep brain stimulation. This may occur, for example if the electrical stimulation is not administered continuously or in an open-loop configuration.

In embodiments, electric stimulation is applied at 5 hertz, 10 hertz, 12 hertz, 160 hertz, 212 hertz, or 333 hertz. In embodiments, electric stimulation is applied at 5 hertz. In embodiments, electric stimulation is applied at 10 hertz. In embodiments, electric stimulation is applied at 12 hertz. In embodiments, electric stimulation is applied at 160 hertz. In embodiments, electric stimulation is applied at 212 hertz. In embodiments, electric stimulation is applied at 333 hertz. In embodiments, electric stimulation is applied at 130 hertz.

In embodiments, bursts of electrical stimulation are applied with a burst duration of the electrical stimulation being 100 milliseconds, 1 minute, 15 minutes, or 1 hour. In embodiments, bursts of electrical stimulation are applied with a burst duration of the electrical stimulation being 100 milliseconds. In embodiments, bursts of electrical stimulation are applied with a burst duration of the electrical stimulation being 1 minute. In embodiments, bursts of electrical stimulation are applied with a burst duration of the electrical stimulation being 15 minutes. In embodiments, bursts of electrical stimulation are applied with a burst duration of the electrical stimulation being 1 hour.

In embodiments, a duty cycle of the electrical stimulation is continuous, bursting, or on for a length of time and off for a different length of time. In embodiments, a duty cycle of the electrical stimulation is continuous. In embodiments, a duty cycle of the electrical stimulation is bursting. In embodiments, a duty cycle of the electrical stimulation is on for a length of time and off for a different length of time.

In embodiments, the low frequency modulation includes a modulation having a frequency between about 0 hertz-38 hertz. In embodiments, the low frequency modulation includes a modulation having a frequency between 0 hertz-38 hertz. In embodiments, the low frequency modulation includes a modulation having a frequency between about 0 hertz-30 hertz. In embodiments, the low frequency modulation includes a modulation having a frequency between 0 hertz-30 hertz. In embodiments, the low frequency modulation includes a modulation having a frequency between about 0 hertz-25 hertz. In embodiments, the low frequency modulation includes a modulation having a frequency between 0 hertz-25 hertz. In embodiments, the low frequency modulation includes a modulation having a frequency between about 0 hertz-20 hertz. In embodiments, the low frequency modulation includes a modulation having a frequency between 0 hertz-20 hertz. In embodiments, the low frequency modulation includes a modulation having a frequency between about 0 hertz-15 hertz. In embodiments, the low frequency modulation includes a modulation having a frequency between 0 hertz-15 hertz. In embodiments, the low frequency modulation includes a modulation having a frequency between about 0 hertz-12 hertz. In embodiments, the low frequency modulation includes a modulation having a frequency between 0 hertz-12 hertz. In embodiments, the low frequency modulation includes a modulation having a frequency between about 0 hertz-10 hertz. In embodiments, the low frequency modulation includes a modulation having a frequency between 0 hertz-10 hertz. In embodiments, the low frequency modulation includes a modulation having a frequency between about 0 hertz-8 hertz. In embodiments, the low frequency modulation includes a modulation having a frequency between 0 hertz-8 hertz. In embodiments, the low frequency modulation includes a modulation having a frequency between about 0 hertz-4 hertz. In embodiments, the low frequency modulation includes a modulation having a frequency between 0 hertz-4 hertz. In embodiments, the low frequency modulation includes a modulation having a frequency between about 0 hertz-3 hertz. In embodiments, the low frequency modulation includes a modulation having a frequency between 0 hertz-3 hertz. In embodiments, the low frequency modulation includes a modulation having a frequency between about 1 hertz-4 hertz. In embodiments, the low frequency modulation includes a modulation having a frequency between 1 hertz-4 hertz.

Apparatus

The methods provided herein, including embodiments thereof, may be practiced using an apparatus suitable for responsive neurostimulation (i.e., therapeutic stimulation triggered in response to a biomarker). Thus, in an aspect is provided an apparatus including: at least one electrode adapted to at least measure brain wave activity in a nucleus accumbens of a subject, wherein the subject is diagnosed with, or suspected of having, a loss of control or impulse control disorder, and to apply an electrical current to the nucleus accumbens of the subject; a controller configured to at least: detect, based at least in part on the measured brain wave activity, at least one low frequency modulation in the nucleus accumbens of the subject, and administer, in response to the detection of the at least one low frequency modulation, electrical stimulation to the nucleus accumbens of the subject, wherein the administering of electrical stimulation includes applying, by the at least one electrode, the electrical current to the nucleus accumbens of the subject.

In embodiments, at least one low frequency modulation is detected. In embodiments, at least 2 low frequency modulations are detected. In embodiments, at least 3 low frequency modulations are detected. In embodiments, at least 4 low frequency modulations are detected. In embodiments, at least 5 low frequency modulations are detected.

In embodiments, the loss of control disorder includes a disorder that is associated with a lack of impulse control, and wherein the loss of control disorder includes one or more of substance abuse, compulsive gambling, binge eating, or suicidal ideation. In embodiments, the loss of control disorder includes substance abuse. In embodiments, the loss of control disorder includes compulsive gambling. In embodiments, the loss of control disorder includes binge eating. In embodiments, the loss of control disorder includes suicidal ideation.

In embodiments, the loss of control disorder includes a disorder that is associated with a lack of impulse control, and wherein the loss of control disorder includes one or more of substance abuse, sex addiction or compulsive sexuality, kleptomania, pyromania, trichotillomania, panic disorder, Intermittent Explosive Disorder, compulsive behaviors including gambling, binge eating, night eating, loss of control eating, emotional or stress eating, compulsive eating, purge behaviors, or suicidal ideation/attempt. In embodiments, the loss of control disorder includes substance abuse. In embodiments, the loss of control disorder includes sex addiction. In embodiments, the loss of control disorder includes compulsive sexuality. In embodiments, the loss of control disorder includes kleptomania. In embodiments, the loss of control disorder includes pyromania. In embodiments, the loss of control disorder includes trichotillomania. In embodiments, the loss of control disorder includes panic disorder. In embodiments, the loss of control disorder includes Intermittent Explosive Disorder. In embodiments, the loss of control disorder includes compulsive behaviors. In embodiments, the compulsive behavior is gambling. In embodiments, the compulsive behavior is binge eating. In embodiments, the compulsive behavior is night eating. In embodiments, the compulsive behavior is loss of control eating. In embodiments, the compulsive behavior is emotional eating. In embodiments, the compulsive behavior is stress eating. In embodiments, the compulsive behavior is compulsive eating. In embodiments, the compulsive behavior is a purge behavior. In embodiments, the compulsive behavior is suicidal ideation. In embodiments, the compulsive behavior is suicidal attempt.

In embodiments, a dose of the electrical stimulation is less than a dose corresponding to deep brain stimulation.

In embodiments electric stimulation is applied at 5 hertz, 10 hertz, 12 hertz, 160 hertz, 212 hertz, or 333 hertz. In embodiments electric stimulation is applied at 5 hertz. In embodiments electric stimulation is applied at 10 hertz. In embodiments electric stimulation is applied at 12 hertz. In embodiments electric stimulation is applied at 160 hertz. In embodiments electric stimulation is applied at 212 hertz. In embodiments electric stimulation is applied at 333 hertz. In embodiments electric stimulation is applied at 130 hertz.

In embodiments, bursts of electrical stimulation are applied with a burst duration of the electrical stimulation being 100 milliseconds, 1 minute, 15 minutes, or 1 hour. In embodiments, bursts of electrical stimulation are applied with a burst duration of the electrical stimulation being 100 milliseconds. In embodiments, bursts of electrical stimulation are applied with a burst duration of the electrical stimulation being 1 minute. In embodiments, bursts of electrical stimulation are applied with a burst duration of the electrical stimulation being 15 minutes. In embodiments, bursts of electrical stimulation are applied with a burst duration of the electrical stimulation being 1 hour.

In embodiments, a duty cycle of the electrical stimulation is continuous, bursting, or on for a length of time and off for a different length of time. In embodiments, a duty cycle of the electrical stimulation is continuous. In embodiments, a duty cycle of the electrical stimulation is bursting. In embodiments, a duty cycle of the electrical stimulation is on for a length of time and off for a different length of time.

In embodiments, the at least one low frequency modulation includes a modulation having a frequency between about 0 hertz-38 hertz. In embodiments, the at least one low frequency includes a modulation having a frequency between 0 hertz-38 hertz. In embodiments, the at least one low frequency includes a modulation having a frequency between about 0 hertz-30 hertz. In embodiments, the at least one low frequency includes a modulation having a frequency between 0 hertz-30 hertz. In embodiments, the at least one low frequency includes a modulation having a frequency between about 0 hertz-25 hertz. In embodiments, the at least one low frequency includes a modulation having a frequency between 0 hertz-25 hertz. In embodiments, the at least one low frequency includes a modulation having a frequency between about 0 hertz-20 hertz. In embodiments, the at least one low frequency includes a modulation having a frequency between 0 hertz-20 hertz. In embodiments, the at least one low frequency includes a modulation having a frequency between about 0 hertz-15 hertz. In embodiments, the at least one low frequency includes a modulation having a frequency between 0 hertz-15 hertz. In embodiments, the at least one low frequency includes a modulation having a frequency between about 0 hertz-12 hertz. In embodiments, the at least one low frequency includes a modulation having a frequency between 0 hertz-12 hertz. In embodiments, the at least one low frequency includes a modulation having a frequency between about 0 hertz-10 hertz. In embodiments, the at least one low frequency includes a modulation having a frequency between 0 hertz-10 hertz. In embodiments, the at least one low frequency includes a modulation having a frequency between about 0 hertz-8 hertz. In embodiments, the at least one low frequency includes a modulation having a frequency between 0 hertz-8 hertz. In embodiments, the at least one low frequency includes a modulation having a frequency between about 0 hertz-4 hertz. In embodiments, the at least one low frequency includes a modulation having a frequency between 0 hertz-4 hertz. In embodiments, the at least one low frequency includes a modulation having a frequency between about 0 hertz-3 hertz. In embodiments, the at least one low frequency includes a modulation having a frequency between 0 hertz-3 hertz. In embodiments, the at least one low frequency includes a modulation having a frequency between about 1 hertz-4 hertz. In embodiments, the at least one low frequency includes a modulation having a frequency between 1 hertz-4 hertz.

System

Further, provided herein is, inter alia, a system for treating loss of control disorders. The system is specifically designed to deliver electrical stimulation to treat and/or prevent loss of control disorder symptoms and use treatment data (e.g., electrical stimulation) and patient data to iteratively refine the electrical stimulation parameters to optimize therapeutic efficacy. Therefore, in an aspect is provided a system for the treatment of loss of control disorders of a subject, the system including: the apparatus as described herein including embodiments thereof; an optimizer including: at least one processor; and at least one memory including program code which when executed by the at least one memory provides operations including: receiving treatment data for a first administration of electrical stimulation and a second administration of electrical stimulation, wherein the first administration of electrical stimulation includes an application of electrical current in accordance to a first set of parameters, and wherein the second administration of electrical stimulation includes another application of electrical current in accordance to a second set of parameters; obtaining patient data indicative of a result of the first electrical stimulation and the second electrical stimulation; and adjusting, based at least on the treatment data and the patient data, a third set of parameters for applying electrical current during a subsequent administration of electrical stimulation.

In embodiments, the first, second, and third set of parameters include a frequency, a duty cycle, and a burst duration for the application of electrical current. In embodiments, the first set of parameters includes a frequency, a duty cycle, and a burst duration for the application of electrical current. In embodiments, the second set of parameters includes a frequency, a duty cycle, and a burst duration for the application of electrical current. In embodiments, the third set of parameters includes a frequency, a duty cycle, and a burst duration for the application of electrical current.

In embodiments, the patient data includes behavioral data associated with the subject. Behavioral data as referred to herein includes without limitation, patient data derived from performance on cognitive tasks, ambulatory assessments, Ecological Momentary Assessment (EMA), and bite counter results. In embodiments, behavioral data is self-reported by the patient.

In embodiments, the at least one of the frequency, duty cycle, and burst duration is adjusted to maximize a reduction or improvement in one or more symptoms associated with the loss of control disorder. In embodiments, the frequency is adjusted to maximize a reduction or improvement in one or more symptoms associated with the loss of control disorder. In embodiments, the duty cycle is adjusted to maximize a reduction or improvement in one or more symptoms associated with the loss of control disorder. In embodiments, the burst duration is adjusted to maximize a reduction or improvement in one or more symptoms associated with the loss of control disorder.

In addition to the electrical stimulation parameters described above (i.e., frequency, duty cycle, and burst duration), is the strength of current stimulation. In embodiments, current stimulation amplitude is adjusted to maximize a reduction or improvement in one or more symptoms associated with the loss of control disorder.

LOC Disorder Treatment System.

Figure 5A:
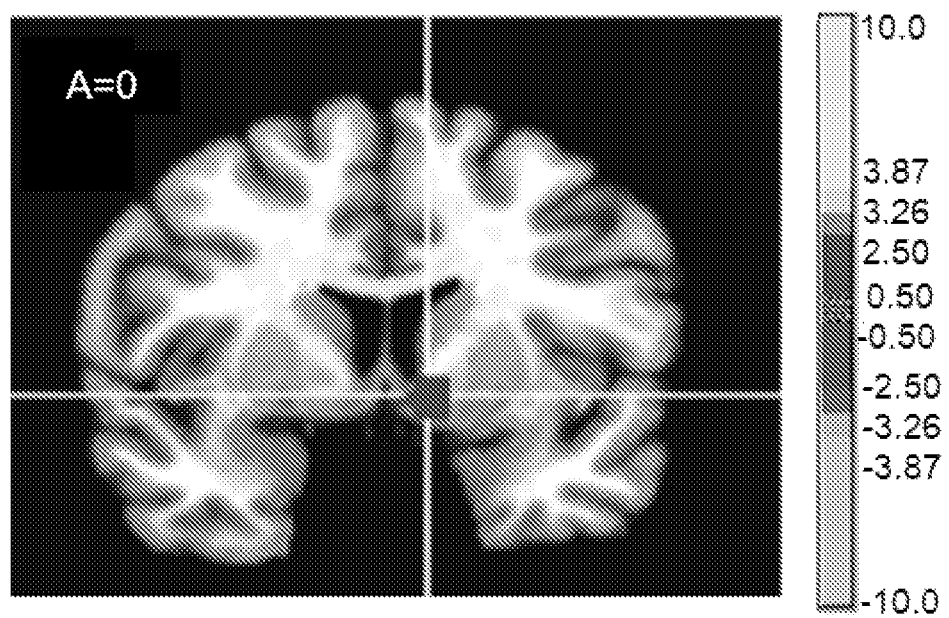
FIGS. 5A-5E.
Figure 5B:
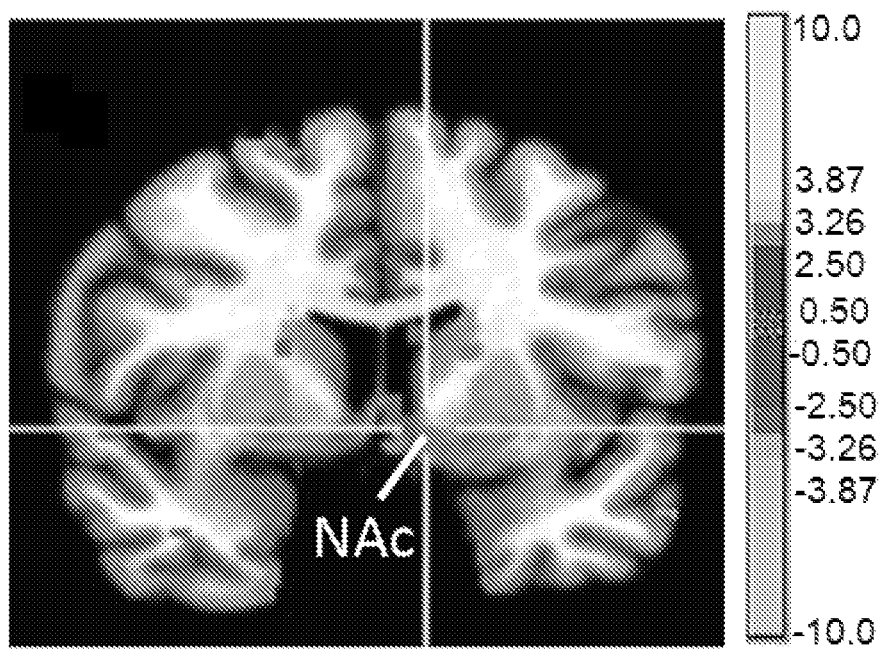
Figure 5C:
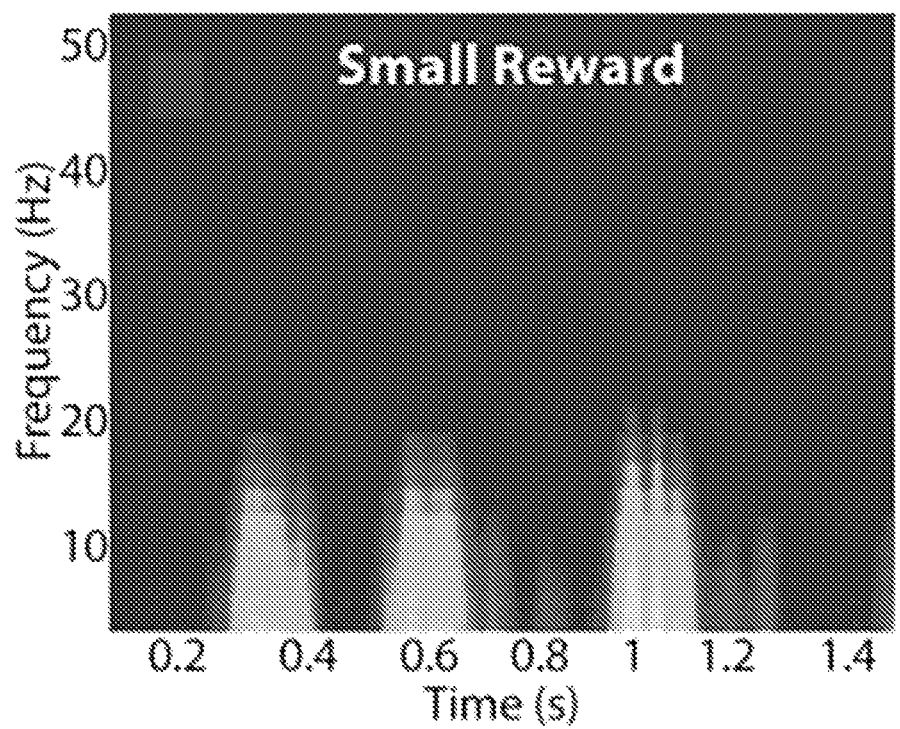
Figure 5D:
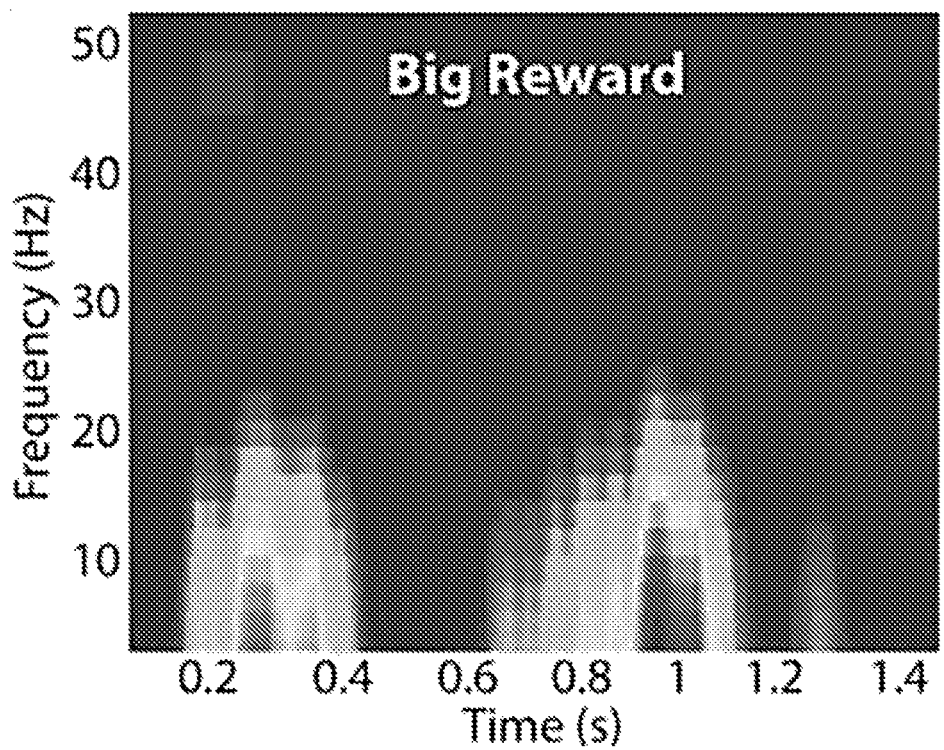
Figure 5E:
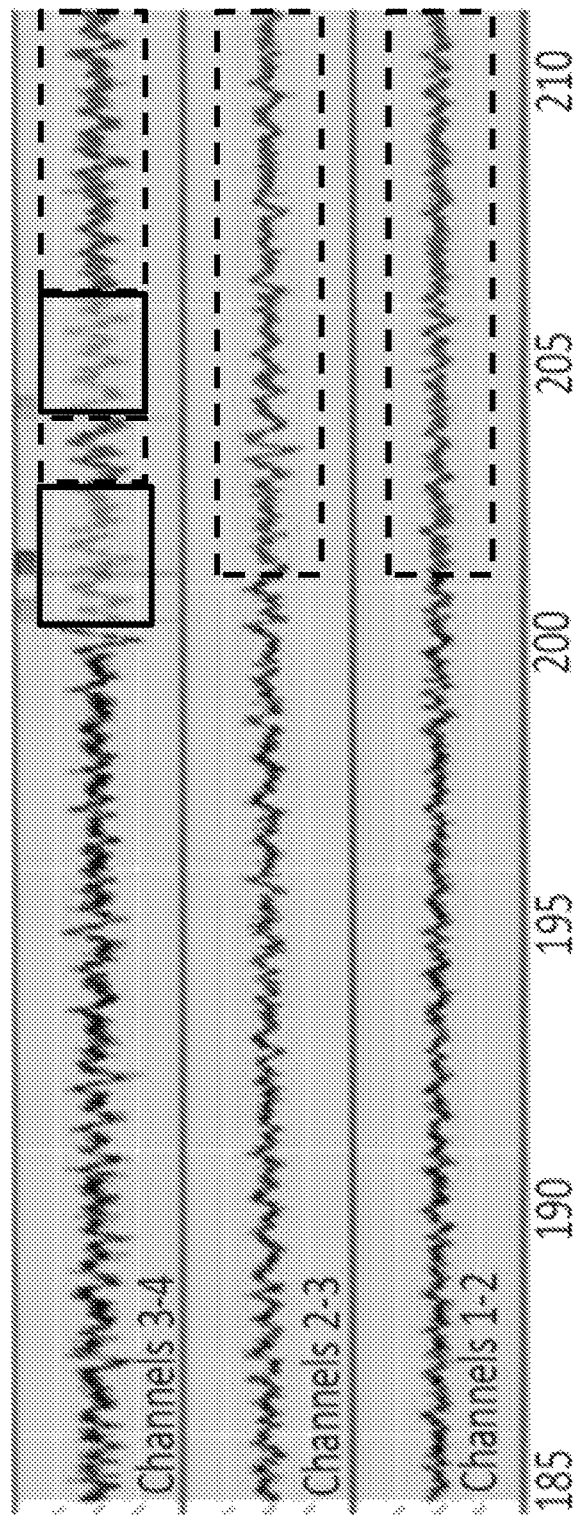
Figure 6:
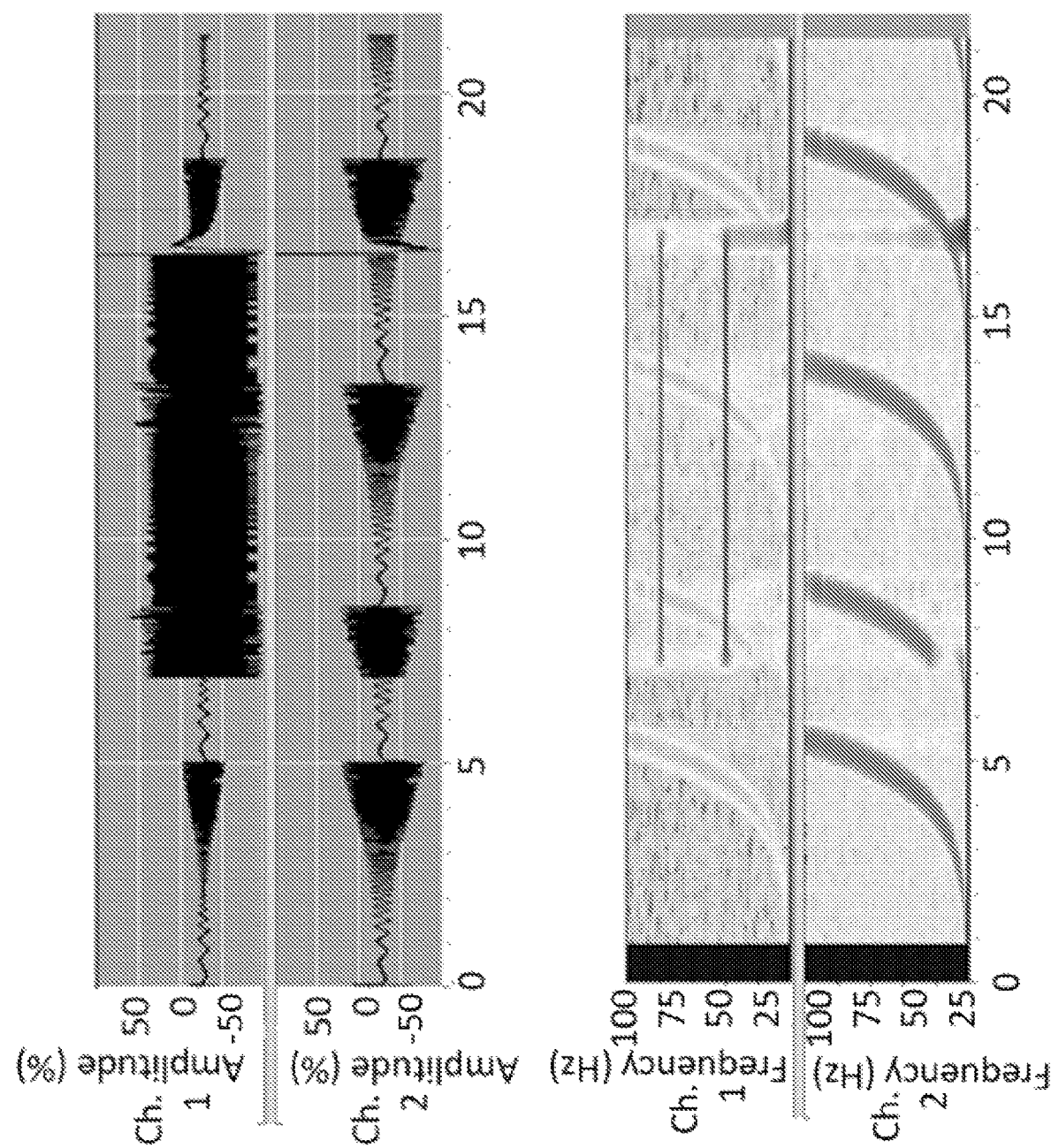
FIG. 6. Concurrent Sense and Stimulation with the RNS® System. The time series (top two traces) and spectrogram (bottom two plots) are displayed for two channels. A frequency sweep with increasing amplitude is looped to the RNS® System and sensed by both channels. A 10-sec 50 Hz burst of stimulation is delivered to Channel 1 (top trace) starting at 7 secs. The frequency sweep continues to be sensed on Channel 1 despite stimulation.
Figure 7:
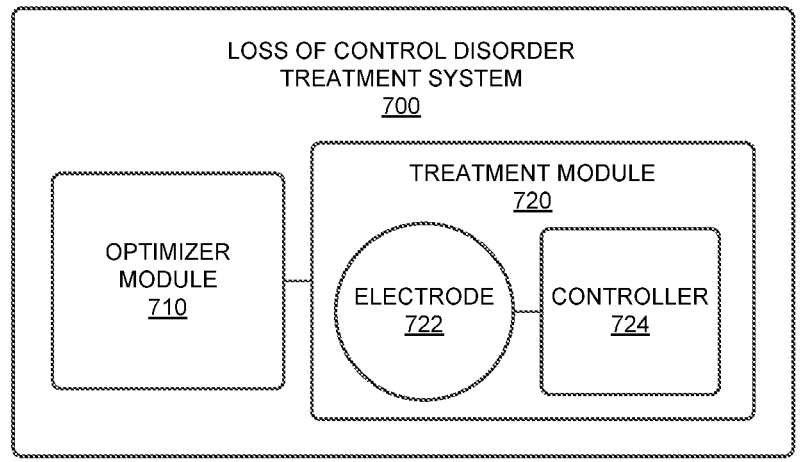
FIG. 7 depicts a block diagram illustrating a system for treating loss of control disorders, in accordance with some example embodiments.

FIG. 7 depicts a block diagram illustrating an LOC disorder treatment system 700, in accordance with some example embodiments. Referring to FIGS. 1-7, the LOC disorder treatment system 700 can be configured to detect predictive signaling in a nucleus accumbens of a subject and to administer treatment for LOC disorders based on the predictive signaling. As shown in FIG. 7, the LOC disorder treatment system 700 can include an optimizer module 710 and a treatment module 720.

In some embodiments, the treatment module 720 may be configured to measure brain wave activity in the nucleus accumbens of a subject. Referring again to FIG. 7, the treatment module 720 may include an electrode 722 and a controller 724. The electrode 722 may be adapted for insertion into the nucleus accumbens of the subject. Moreover, the electrode 722 may be configured to measure brain wave activity in the nucleus accumbens of the subject as well as to apply electrical current to the nucleus accumbens of the subject. As shown in FIG. 7, the treatment module 720 may include a controller 724 that is coupled to the electrode 722 and configured to control the operations of the electrode 722. For example, the controller 724 may be configured to determine, based on the brain wave activity (e.g., measured by the electrode 722), when to administer electrical stimulation to the nucleus accumbens of the subject.

In some embodiments, the measured brain wave activity can include at least one low frequency modulation, which may be a modulation having a frequency of between approximately 0 hertz to 38 hertz, 0 hertz to 12 hertz, and/or 0 hertz to 8 hertz. The presence of the at least one low frequency modulation may be predicative of the symptoms associated with one or more LOC disorders including, for example, substance abuse, sex addiction or compulsive sexuality, kleptomania, pyromania, trichotillomania, panic disorder, Intermittent Explosive Disorder, and compulsive behavior (e.g., gambling, binge eating, night eating, loss of control eating, emotional or stress eating, compulsive eating, purge behaviors, suicidal ideation/attempt, and/or the like).

The controller 724 may administer the electrical stimulation by at least applying, via the electrode 722, an electrical current to the nucleus accumbens of the subject. According to some embodiments, the controller 724 may be configured to administer a dose of electrical stimulation that is less than a dose associated with deep brain stimulation. Thus, the controller 724 may control the dose of the electrical stimulation by at least controlling the parameters associated with the electrical stimulation including, for example, the frequency, burst duration, and/or duty cycle of the electrical current applied to the nucleus accumbens of the subject. For instance, the frequency of the electrical current may be 5 hertz, 10 hertz, 12 hertz, 160 hertz, 212 hertz, and/or 333 hertz. Meanwhile, the burst duration of the electrical current may be 100 milliseconds, 1 minute, 15 minutes, and/or 1 hour. The duty cycle of the electrical current may be continuous bursting, and/or on for a length of time and off for a different length of time.

In some example embodiments, the optimizer module 710 may be configured to adjust the parameters associated with the administration of electrical stimulation including, for example, the frequency, duty cycle, and burst duration of the electrical current that is applied to the nucleus accumbens of the subject. For example, the treatment module 720 (e.g. the controller 724) may administer electrical stimulation to the nucleus accumbens of a subject by at least applying (e.g., via the electrode 722) an electric current having different parameters such as frequency, duty cycle, burst duration, and/or the like. According to some embodiments, the optimizer module 710 may obtain patient data, such as behavioral data and/or the like, that may be indicative of a result of the electrical stimulation that is administered with the different parameters. For instance, the result of the electrical stimulation may indicate that administering electrical stimulation having a first set of parameters is more effective at reducing and/or improving LOC symptoms than administering electrical stimulation having a second set of parameters. As such, the optimizer module 710 may determine, based on the result of the simulation, a third set of parameters for a subsequent administration of electrical stimulation (e.g., by the treatment module 720) to the nucleus accumbens of the subject. The third set of parameters may be optimized by at least adjusting the parameters (e.g., frequency, duty cycle, burst duration) that was used in previous administrations of electrical stimulation. Particularly, the third set of parameters may be optimize to maximize a reduction and/or improvement in the symptoms associated with the LOC disorder.

LOC Disorder Treatment Method.

Figure 8:
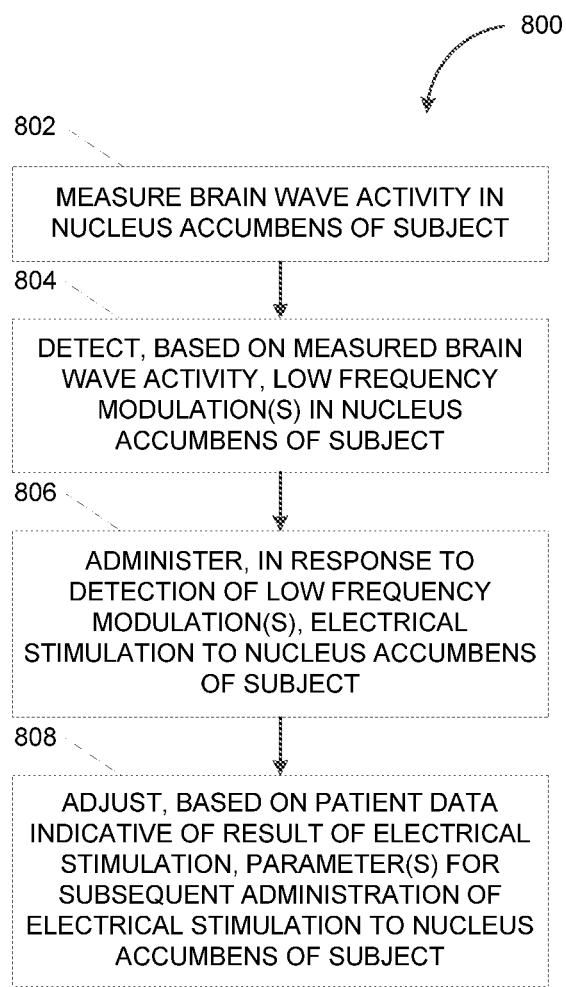
FIG. 8 depicts a flowchart illustrating a process for treating loss of control disorders, in accordance with some example embodiments.

FIG. 8 depicts a flowchart illustrating a process 800 for treating loss of control disorders, in accordance with some example embodiments. Referring to FIGS. 1-8, the process 800 may be performed by the LOC disorder treatment system 700.

The LOC disorder treatment system 700 may measure brain wave activity in a nucleus accumbens of a subject (802). For example, the electrode 722 may be inserted into the nucleus accumbens of the subject in order to measure the brain wave activity in the nucleus accumbens.

The LOC disorder treatment system 700 may detect, based at least on the measured brain wave activity, at least one low frequency modulation in the nucleus accumbens of the subject (804). For instance, the LOC disorder treatment system 700 (e.g., the controller 724) may detect, within the measured brain wave activity, the presence of at least one low frequency modulation. The presence of the at least one low frequency modulation may be predicative of the symptoms associated with one or more LOC disorders including, for example, substance abuse, sex addiction or compulsive sexuality, kleptomania, pyromania, trichotillomania, panic disorder, Intermittent Explosive Disorder, and compulsive behavior (e.g., gambling, binge eating, night eating, loss of control eating, emotional or stress eating, compulsive eating, purge behaviors, suicidal ideation/attempt, and/or the like).

The LOC disorder treatment system 700 can administer, in response to the detection of the at least one low frequency modulation, electrical stimulation to the nucleus accumbens of the subject (806). For example, the LOC disorder treatment system 700 (e.g., the controller 724) may administer electrical stimulation by at least applying, via the electrode 722, an electrical current to the nucleus accumbens of the subject. In some embodiments, the controller 724 may be configured to administer a dose of electrical stimulation that is less than a dose associated with deep brain stimulation. Thus, the controller 724 may control the dose of the electrical stimulation by at least controlling the parameters associated with the electrical stimulation (e.g., the frequency, burst duration, and/or duty cycle of the electrical current applied to the nucleus accumbens of the subject).

The LOC disorder treatment system 700 can adjust, based at least on patient data indicative of a result of the electrical stimulation, one or more parameters for a subsequent administration of electrical stimulation to the nucleus accumbens of the subject (808). For example, the LOC disorder treatment system 700 may receive patient data (e.g., behavioral data) indicating a result of past administrations of electrical stimulation. That is, the LOC disorder treatment system 700 may receive patient data that indicates the effectiveness of applying, to the nucleus accumbens of the subject, electrical current having different parameters (e.g., frequency, duty cycle, burst duration). Thus, the LOC disorder treatment system 700 (e.g., the optimizer module 720) may adjust, based on the patient, the parameters (e.g., frequency, duty cycle, burst duration) that are used in previous administrations of electrical stimulation. In doing so, the LOC disorder treatment system 700 may generate a set of parameters that is optimized to maximize a reduction and/or improvement in the symptoms associated with the LOC disorder.

Implementations of the present disclosure can include, but are not limited to, methods consistent with the descriptions provided above as well as articles that comprise a tangibly embodied machine-readable medium operable to cause one or more machines (e.g., computers, etc.) to result in operations implementing one or more of the described features. Similarly, computer systems are also described that can include one or more processors and one or more memories coupled to the one or more processors. A memory, which can include a computer-readable storage medium, can include, encode, store, or the like one or more programs that cause one or more processors to perform one or more of the operations described herein. Computer implemented methods consistent with one or more implementations of the current subject matter can be implemented by one or more data processors residing in a single computing system or multiple computing systems. Such multiple computing systems can be connected and can exchange data and/or commands or other instructions or the like via one or more connections, including but not limited to a connection over a network (e.g. the Internet, a wireless wide area network, a local area network, a wide area network, a wired network, or the like), via a direct connection between one or more of the multiple computing systems, etc.

One or more aspects or features of the subject matter described herein can be realized in digital electronic circuitry, integrated circuitry, specially designed application specific integrated circuits (ASICs), field programmable gate arrays (FPGAs) computer hardware, firmware, software, and/or combinations thereof. These various aspects or features can include implementation in one or more computer programs that are executable and/or interpretable on a programmable system including at least one programmable processor, which can be special or general purpose, coupled to receive data and instructions from, and to transmit data and instructions to, a storage system, at least one input device, and at least one output device. The programmable system or computing system can include clients and servers. A client and server are generally remote from each other and typically interact through a communication network. The relationship of client and server arises by virtue of computer programs running on the respective computers and having a client-server relationship to each other.

These computer programs, which can also be referred to as programs, software, software applications, applications, components, or code, include machine instructions for a programmable processor, and can be implemented in a high-level procedural language, an object-oriented programming language, a functional programming language, a logical programming language, and/or in assembly/machine language. As used herein, the term "machine-readable medium" refers to any computer program product, apparatus and/or device, such as for example magnetic discs, optical disks, memory, and Programmable Logic Devices (PLDs), used to provide machine instructions and/or data to a programmable processor, including a machine-readable medium that receives machine instructions as a machine-readable signal. The term "machine-readable signal" refers to any signal used to provide machine instructions and/or data to a programmable processor. The machine-readable medium can store such machine instructions non-transitorily, such as for example as would a non-transient solid-state memory or a magnetic hard drive or any equivalent storage medium. The machine-readable medium can alternatively or additionally store such machine instructions in a transient manner, such as for example as would a processor cache or other random access memory associated with one or more physical processor cores.

To provide for interaction with a user, one or more aspects or features of the subject matter described herein can be implemented on a computer having a display device, such as for example a cathode ray tube (CRT) or a liquid crystal display (LCD) or a light emitting diode (LED) monitor for displaying information to the user and a keyboard and a pointing device, such as for example a mouse or a trackball, by which the user may provide input to the computer. Other kinds of devices can be used to provide for interaction with a user as well. For example, feedback provided to the user can be any form of sensory feedback, such as for example visual feedback, auditory feedback, or tactile feedback; and input from the user can be received in any form, including, but not limited to, acoustic, speech, or tactile input. Other possible input devices include, but are not limited to, touch screens or other touch-sensitive devices such as single or multi-point resistive or capacitive trackpads, voice recognition hardware and software, optical scanners, optical pointers, digital MRI image capture devices and associated interpretation software, and the like.

In the descriptions above and in the claims, phrases such as "at least one of" or "one or more of" may occur followed by a conjunctive list of elements or features. The term "and/or" may also occur in a list of two or more elements or features. Unless otherwise implicitly or explicitly contradicted by the context in which it used, such a phrase is intended to mean any of the listed elements or features individually or any of the recited elements or features in combination with any of the other recited elements or features. For example, the phrases "at least one of A and B;" "one or more of A and B;" and "A and/or B" are each intended to mean "A alone, B alone, or A and B together." A similar interpretation is also intended for lists including three or more items. For example, the phrases "at least one of A, B, and C;" "one or more of A, B, and C;" and "A, B, and/or C" are each intended to mean "A alone, B alone, C alone, A and B together, A and C together, B and C together, or A and B and C together." Use of the term "based on," above and in the claims is intended to mean, "based at least in part on," such that an unrecited feature or element is also permissible.

The subject matter described herein can be embodied in systems, apparatus, methods, and/or articles depending on the desired configuration. The implementations set forth in the foregoing description do not represent all implementations consistent with the subject matter described herein. Instead, they are merely some examples consistent with aspects related to the described subject matter. Although a few variations have been described in detail above, other modifications or additions are possible. In particular, further features and/or variations can be provided in addition to those set forth herein. For example, the implementations described above can be directed to various combinations and subcombinations of the disclosed features and/or combinations and subcombinations of several further features disclosed above. In addition, the logic flows depicted in the accompanying figures and/or described herein do not necessarily require the particular order shown, or sequential order, to achieve desirable results. Other implementations can be within the scope of the following claim.

EXAMPLES

Example 1: NAc Stimulation in a Mouse Model of Binge-Like Eating Behavior

Figure 1C:
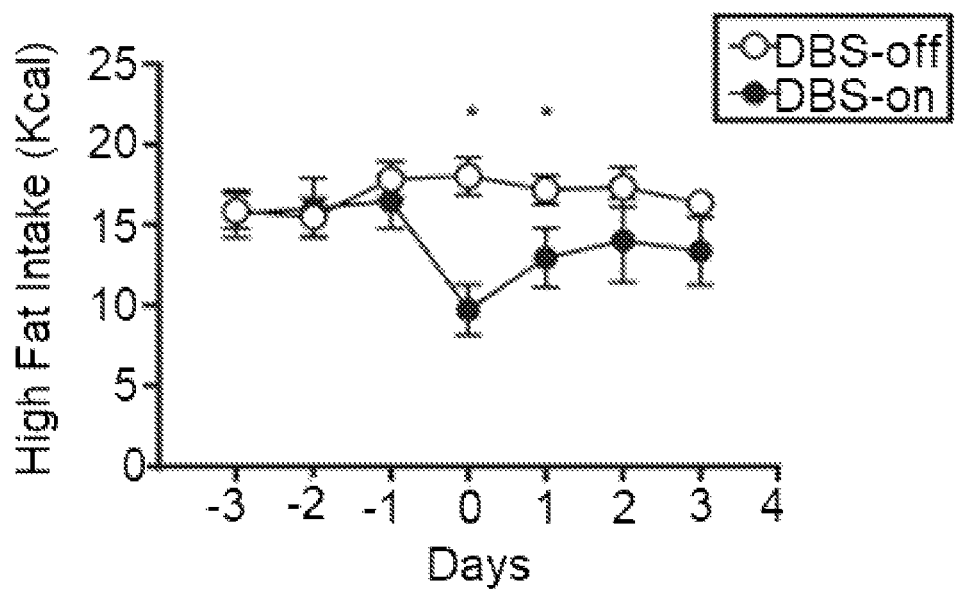
Figure 1D:
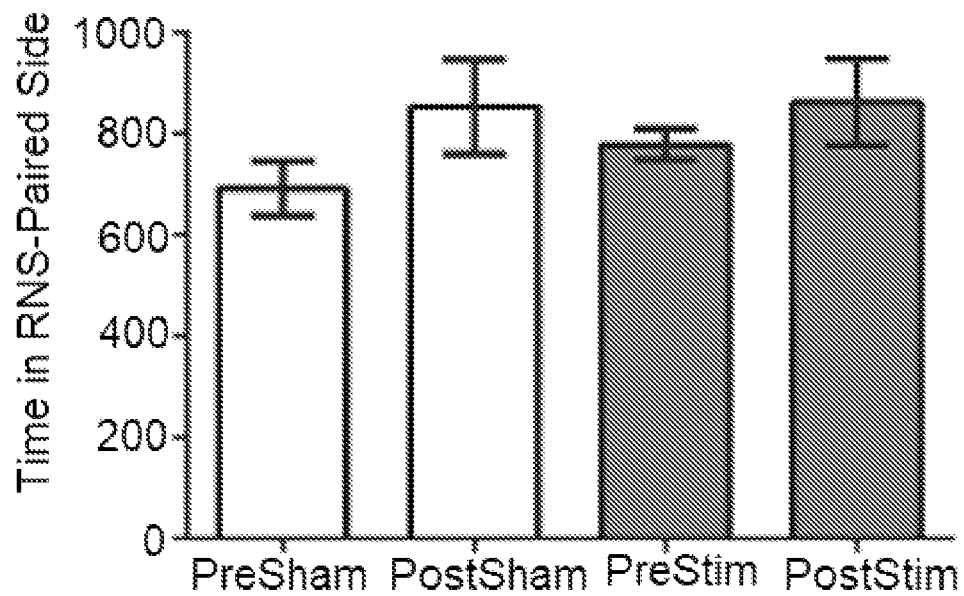
Figure 1E:
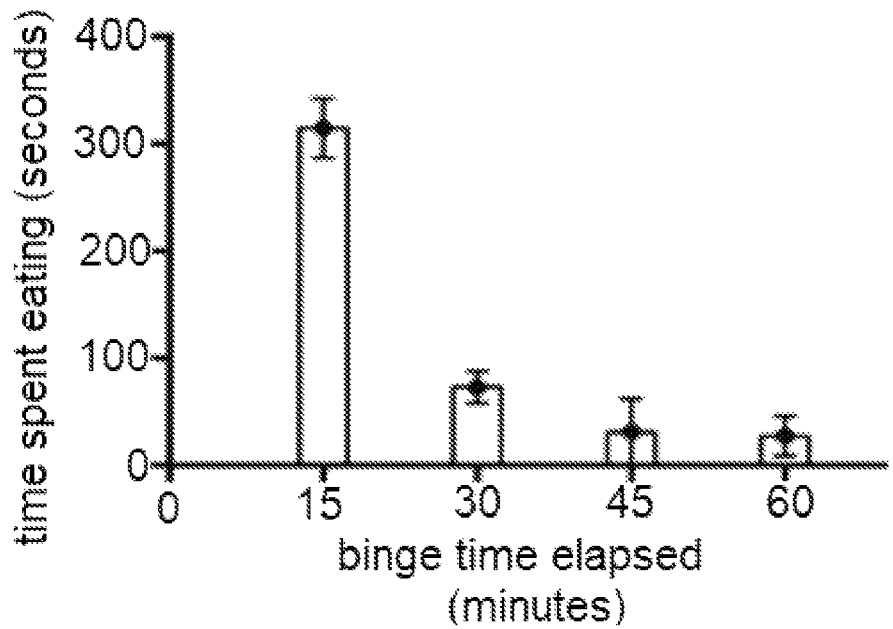
Figure 1F:
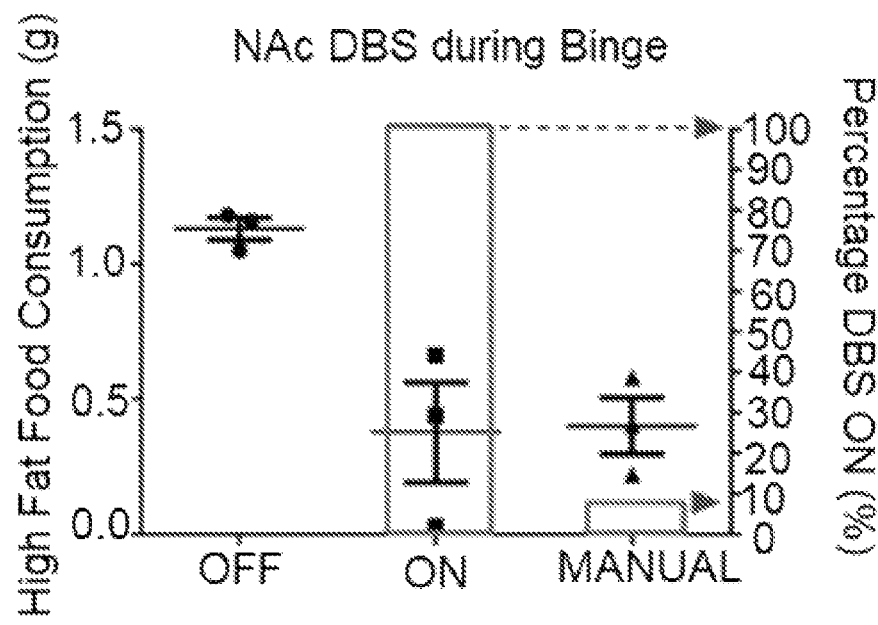

It was found that electrically stimulating the nucleus accumbens (NAc) attenuates binge-like eating of high fat (HF) food (FIG. 1B), and this effect exhibited "dose" response.[42,40] Stimulation (DBS) was turned on immediately before and during 1-hour access to the food. Subsequent chronic studies in mice revealed reduced intake with continuous NAc DBS, but a tolerance effect was evident (FIG. 1C). NAc DBS did not induce a place preference, suggesting binge blockade did not involve reward substitution (FIG. 1D). Binge-like behavior in mice is episodic, much like LOC eating in humans (FIG. 1E).[15] This episodic behavior, combined with an apparent tolerance effect to chronic continuous stimulation supports stimulating intermittently only to block binge onset. Indeed, binge blockade was seen in the preliminary studies with manually administering stimulation only during approach to the high fat food with >90% decrease in the cumulative "dose" (i.e. percent time on) (FIG. 1F).

The RNS® System.

Figure 2A:
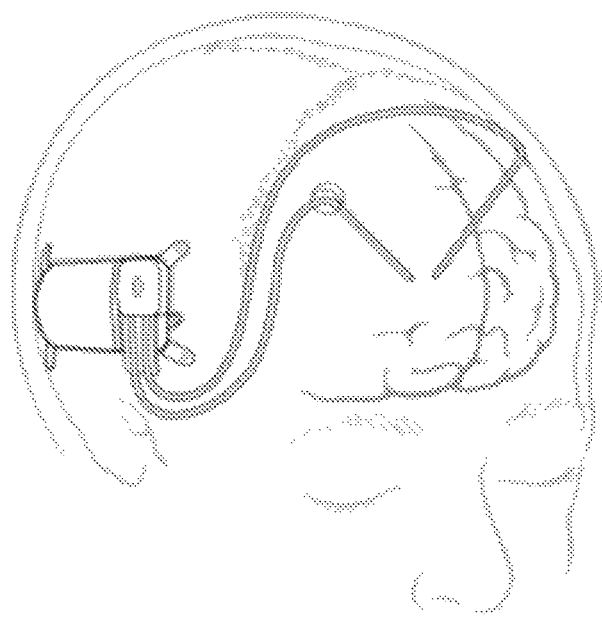
FIGS. 2A-2C: Components of the proposed rRNS System.
Figure 2B:
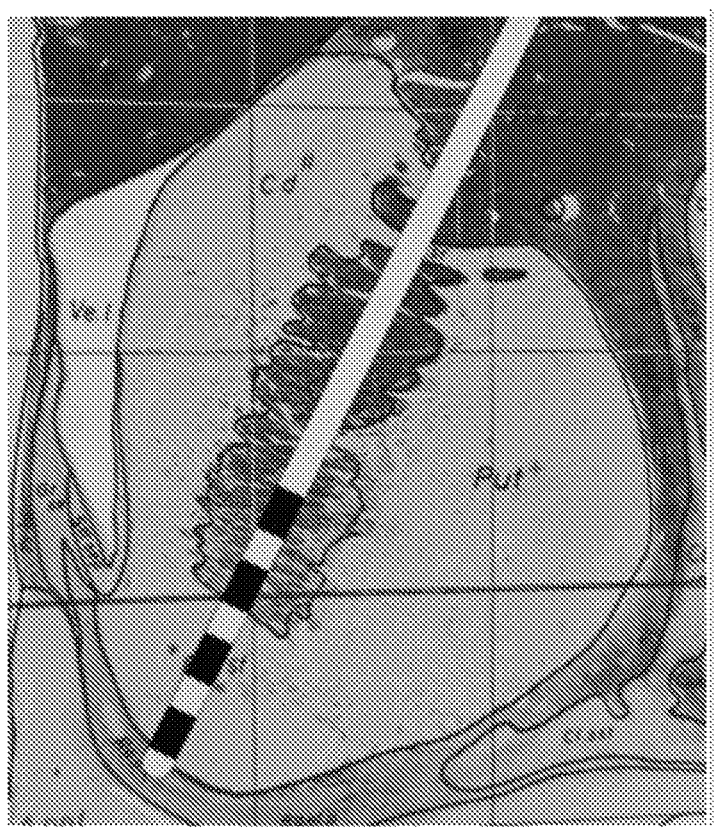
Figure 2C:
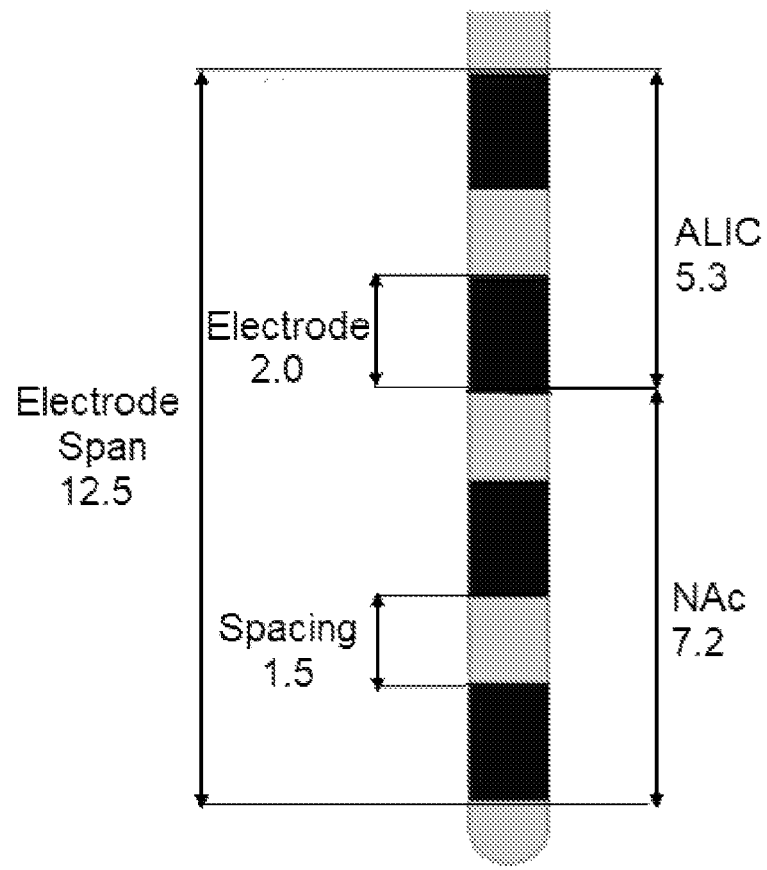

This is the first FDA approved responsive neurostimulation system, and includes a cranially implanted responsive neurostimulator connected to 2 leads, a physician programmer, a patient remote monitor, and an internet-based data repository for physicians and NeuroPace, Inc. to review stored local field potentials (LFPs). The proposed system (rRNS) for the EFS includes approved depth leads targeted to the human NAc (FIGS. 2A and 2B). The depth leads (DL-330-3.5 or DL-344-3.5) have four electrodes with 1.5 mm spacing (FIG. 2C). A prototype rRNS will be developed for the non-clinical mouse study and refined for the EFS. The rRNS System will incorporate new software features (only) into the existing hardware. Using this system for the proposed studies will leverage: (1) FDA-approved hardware; (2) prior clinical safety data; (3) experience adapting the system to rodents; (4) chronic implantation; (5) responsive stimulation capabilities; (6) ability to collect a rich electrographic dataset; and (7) a proven successful user interface.

Clinical Safety

FDA approval for the RNS® System was based on data from 3 clinical trials including a feasibility study to demonstrate safety (N=65) and a 2-year multi-center double-blind randomized controlled pivotal trial to assess safety and efficacy (n=191). These studies demonstrated that the RNS® System is safe and effective for medically intractable partial onset seizures.[6] An open-label trial that follows patients for an additional 7 years (n=256) is ongoing. As of the last data cutoff (Dec. 1, 2015), the mean follow-up was 6.8 years with an accumulated 1715 patient implant years and 1613 stimulation years. Responsive neurostimulation was well-tolerated, and efficacy was durable and even significantly improved at long-term.[6] Moreover, no cognitive decline was detected, but rather significant improvements in naming, verbal learning, and QOL.[62,68] Serious adverse events (SAEs) included infections (3.5%) at a rate similar to if not better than other implants.[41,70] The overall rates of SAEs related to the implanted neurostimulator and leads were not higher than intracranial electrodes used to localize seizure foci,[21,93] or for DBS.[104]

The safety profile of implanting and using the rRNS for LOC eating is further complemented by safety and efficacy data available on targeting and stimulating the NAc with DBS for OCD, and more recently major depression.[19,33] OCD studies have demonstrated that significant improvements can be predicted by a positive affect induced during monopolar assessments intraoperatively and in the clinic.[46] This is standard in the DBS protocol for obsessive compulsive disorder (OCD) and this protocol will be implemented in the early feasibility study (EFS) for LOC eating. Long-term outcomes have demonstrated benefits to OCD, as well as safety of chronically stimulating the NAc, as no adverse effects on neuropsychological outcomes or psychosocial functioning, including sexual function, have been reported.[75] In fact, significant improvements in quality of life (QOL) have been documented.[75] The most common adverse effect reported is transient hypomania at high stimulation voltages and amplitudes, and thus, current amplitude will be kept low, starting at 0.5 mA (see Monopolar Assessment), and the psychiatrist with expertise in NAc DBS will closely monitor subjects during stimulation phases.[19] Given that the NAc, will be intermittently stimulated it is expected that the overall "dose" or time-on of stimulation to be significantly less than DBS (as seen in the mouse model, FIG. 1F). In fact, even using a duty cycle (1 min on, 5 mins off paradigm) leads to 4 hrs/day of stimulation as was attempted in the SANTE DBS epilepsy trial, which is far higher than the average time-on in NeuroPace's RNS® pivotal trial of about 5 mins/day.[52,70]

The RNS® Prototypes in Rodents

Figure 4A:
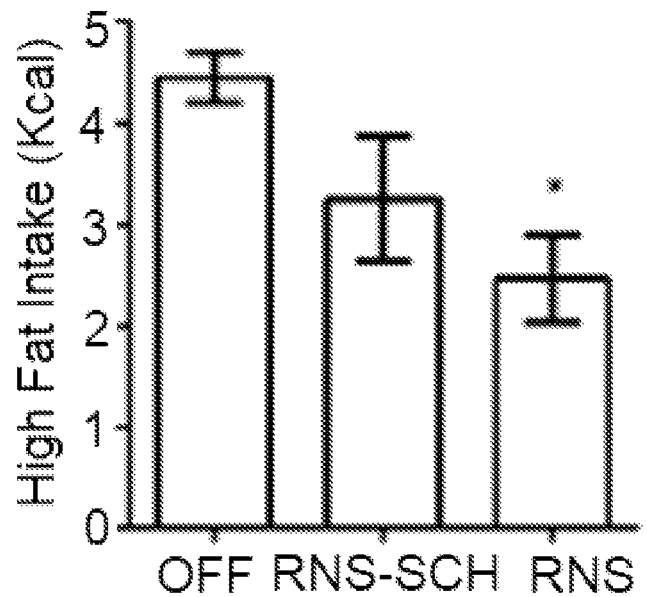
FIGS. 4A-4B.

Real-time LFP activity from the mouse NAc is can be recorded using a prototype neurostimulator (FIG. 3). Increased power in low frequency oscillations (mostly delta) in the NAc prior to binge onset has been detected (FIGS. 3A and 3B). Behavioral specificity was assessed by reviewing LFPs prior to chow intake and social interaction (FIGS. 3C and 3F). None of these behaviors were associated with increased low frequency oscillatory power in the NAc. Thus, a new cohort of mice was prepared, and a variety of parameters were assessed, including scheduled (RNS-Sch) and responsive stimulation optimized by delta power (RNS, FIG. 4A). There was no social impairment with closed-loop stimulation optimized by delta power. Complementing the mouse LFP data are intraoperative LFPs recorded from the NAc in a patient with OCD. In an IRB-approved study (IRB-33146), this patient partook in a financial task that was confirmed to recruit NAc activity during DBS (FIGS. 5A and 5B).[55] This study revealed corollary changes in low frequency oscillations during anticipation of financial gain, and the power was proportional to the magnitude of the gain (FIGS. 5C and 5D). Working with NeuroPace it was determined if the existing detection algorithms can sense these oscillations. FIG. 5E shows the detection by a benchtop RNS®. This finding suggests that LFPs from the mouse NAc can reflect what is expected in humans, despite different sized electrodes, impedances, and modified sensing hardware. Moreover, power fluctuations in this low frequency may be specific to certain gain anticipation as seen in fMRI studies of the NAc, suggesting potential for behavioral specificity with closed-loop stimulation in humans.[55]

Real-Time Continuous LFPs with RNS® System

Participants will partake in in-office experiments. During these controlled assessments, RNS® System accessories will be used to record real-time continuous LFPs while patients participate in experiments (e.g. Milkshake Paradigm, LOC Lab Study). Real-time, continuous LFP data synchronized with ambulatory and cognitive tasks will be collected. A similar approach synchronized with videoed tasks and the LOC eating laboratory will be employed.

Chronic Implantation.

One approach used to develop neurotechnologies has been initially testing them in the subacute setting. There are concerns about generalizability of the subacute response to stimulation. During the RNS® System pivotal trial, median seizure reduction was 38% over months 3 through 5, increasing to 44% at 1 year and reaching 66% after year 3.6,47 Similar improvements over time have been observed for other neuromodulatory therapies. 83 Second, there is a subacute implant effect on seizures given an immediate reduction of seizures independent of stimulation.[25,70]

Responsive Stimulation.

The RNS® System has also been used to examine other episodic disorders, such as Tourette Syndrome (TS).[64] Stimulation resulted in tic reduction, and LFP recordings revealed a potential predictor of tic occurrence. A follow-on study to identify a biomarker of spontaneous tics in TS patients is ongoing. LOC eating in obesity is another episodic behavioral disorder, and the RNS® System's success in identifying biomarkers of other episodic disorders will be leveraged to define for the first time an LFP signal that predicts LOC and effectively triggers stimulation to block it.

Example 2: Algorithm Development and Testing Using a Validated Mouse Model

Optimize Stimulation Parameters.

A limited number of parameters have been evaluated.[42] Initial stimulation parameters will be optimized by sequentially screening a range of frequencies (e.g. 5, 12, 160, and 333 Hz), burst durations (e.g. 100 ms, 1 min, 15 min, 1 hr), duty cycles (e.g. continuous, 1 s—on, 5 s—off, bursting), timing (e.g. before, after binge onset, schedule), and laterality (unilateral, bilateral). Specific parameters will be tested longitudinally. After testing, candidate parameters will be rank ordered by the average reduction in high-fat intake; the highest ranking candidates ("Optimized" in Table 1) will be promoted to further testing. Behavioral data will be collected using real-time video software (Noldus EthoVision® XT), which is time-synchronized to the electrophysiology unit.

TABLE 1

Preclinical studies planned for optimization of stimulatory parameters.

| Task | Laterality | Timing | Frequency | Duration | Duty Cycle | N | Calendar Weeks |
|---|---|---|---|---|---|---|---|
| 1.1 | Unilateral | Before pellet | Vary | 1 hour | None | 10 | 8 |
|  |  |  | Optimized | Vary | None | 10 | 8 |
|  |  |  | Optimized | Optimized | Vary | 10 | 8 |
|  | Unilateral | After binge (manual)* |  | Optimized |  | 10 | 6 |
|  |  | Scheduled |  |  |  | 10 | 8 |
|  | Bilateral vs unilateral |  | Optimized |  |  | 10 | 6 |
| 1.2 |  |  | Optimized |  | LFP-responsive* | 10 | 12 |
| 1.3 |  | Optimized with sucrose pellet |  |  |  | 10 | 6 |
|  |  | Optimized with 16 hr food deprivation |  |  |  | 10 | 6 |
|  |  | Optimized + female |  |  |  | 10 | 6 |
| Total |  |  |  |  |  | 100 | 74 |

*to assess manual triggering of stimulation

Optimize Detection Algorithms for Low Frequency Biomarker.

Real-time LFP data from the mouse NAc will be continuously and simultaneously recorded using the prototype rRNS neurostimulator (500 Hz sampling rate) and off-the-shelf acquisition software (5000 Hz sampling rate) for further characterization of low frequency power oscillations associated with binge onset. Novel detection algorithms will be implemented for real-time detection and settings will be refined in each mouse. Algorithms may include half-wave based spectrograms, and methods for identifying changes in cross-frequency coupling, signal attenuation, and power fluctuations. An additional cohort of mice will be used to assess the efficacy of responsive stimulation using parameters and detection algorithms optimized as described herein.

Evaluate Behavioral Specificity of Responsive Neurostimulation.

Figure 3A:
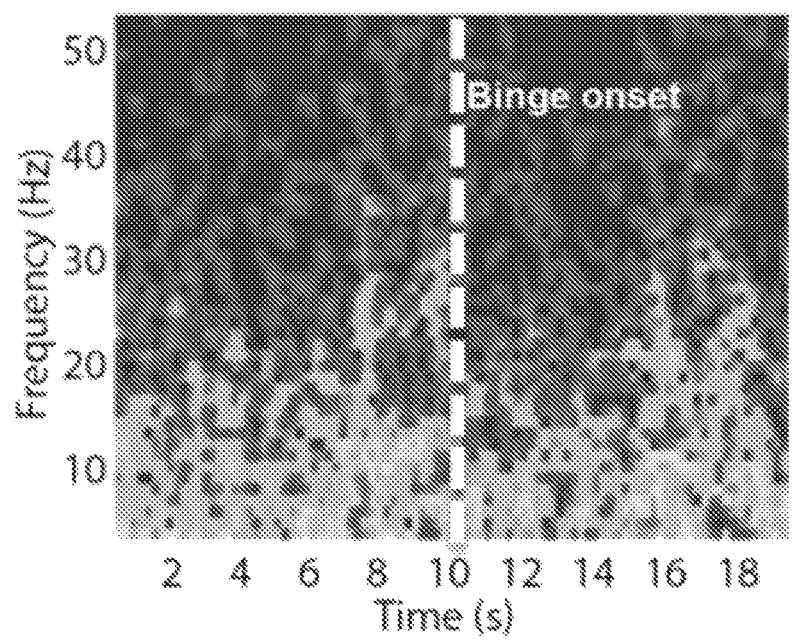
FIGS. 3A-3F.
Figure 3B:
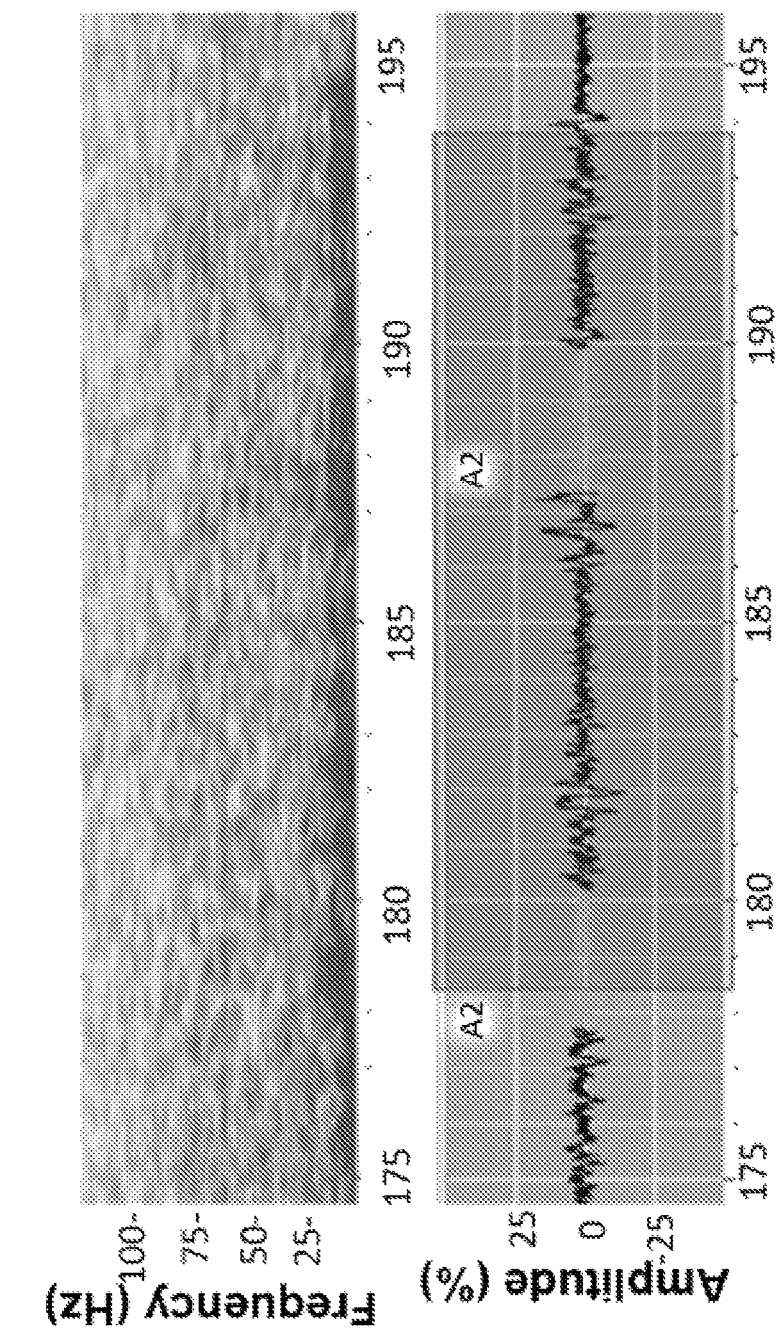
Figure 3C:
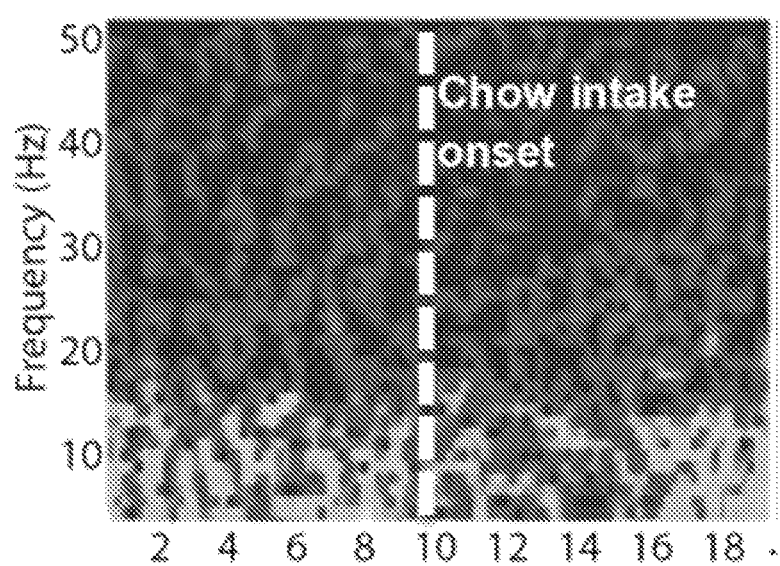
Figure 3D:
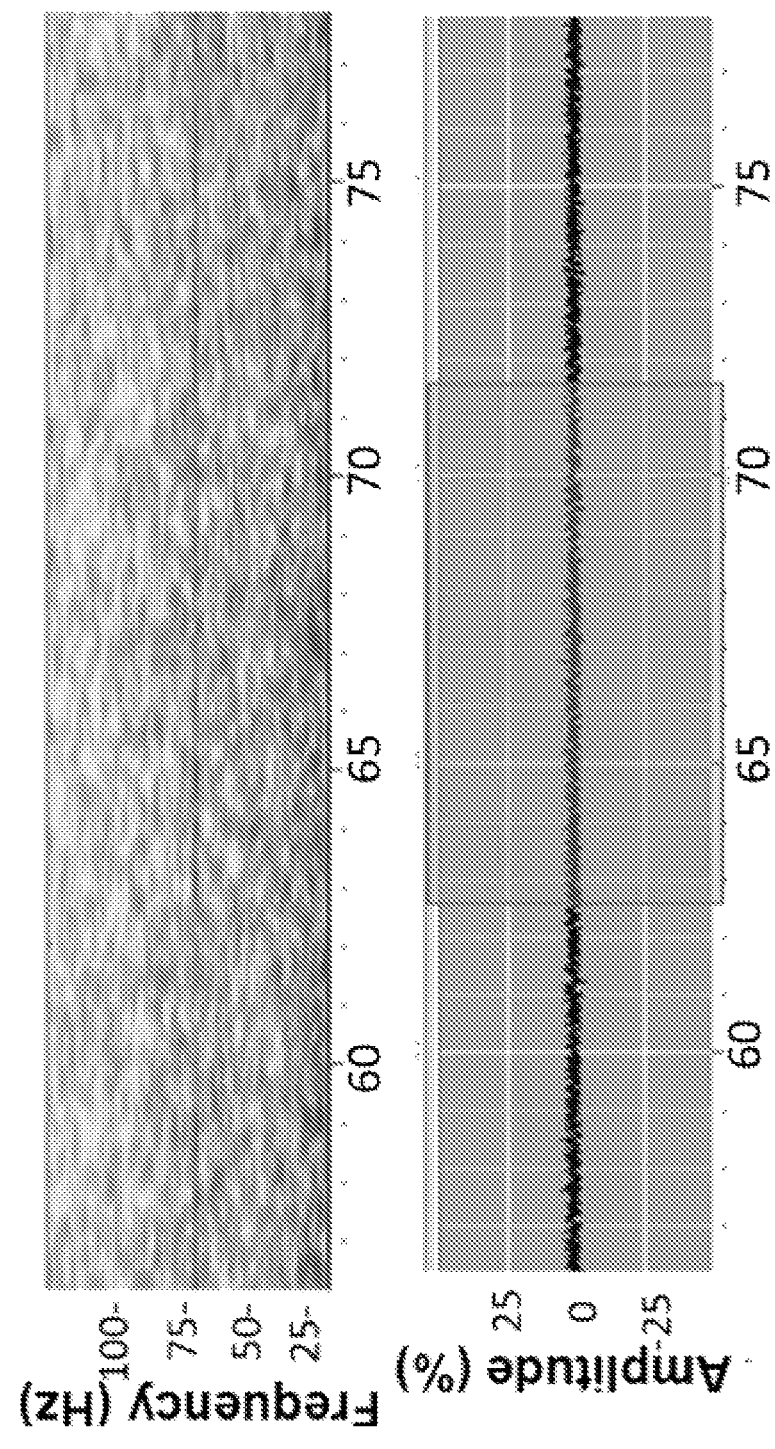
Figure 3E:
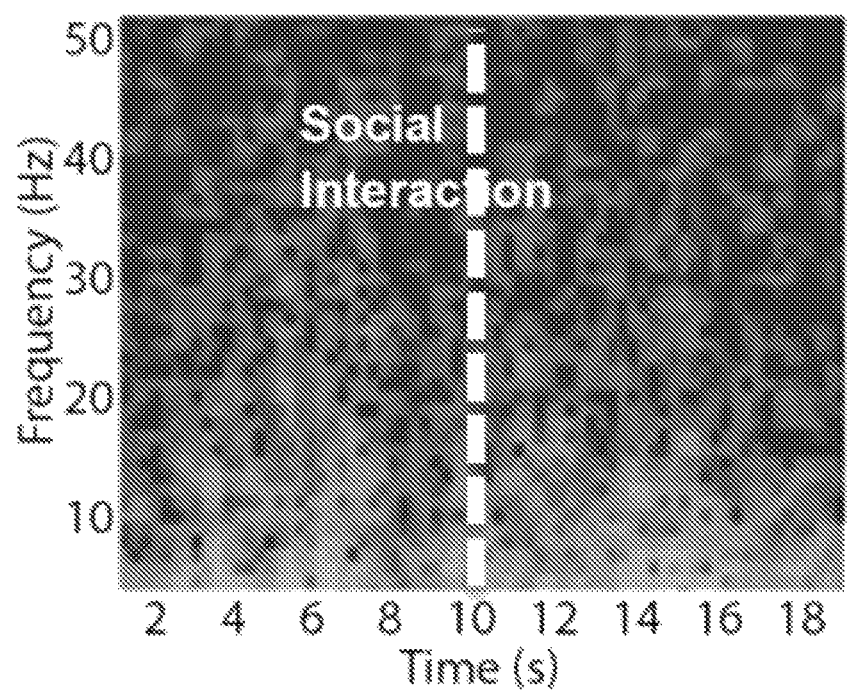
Figure 3F:
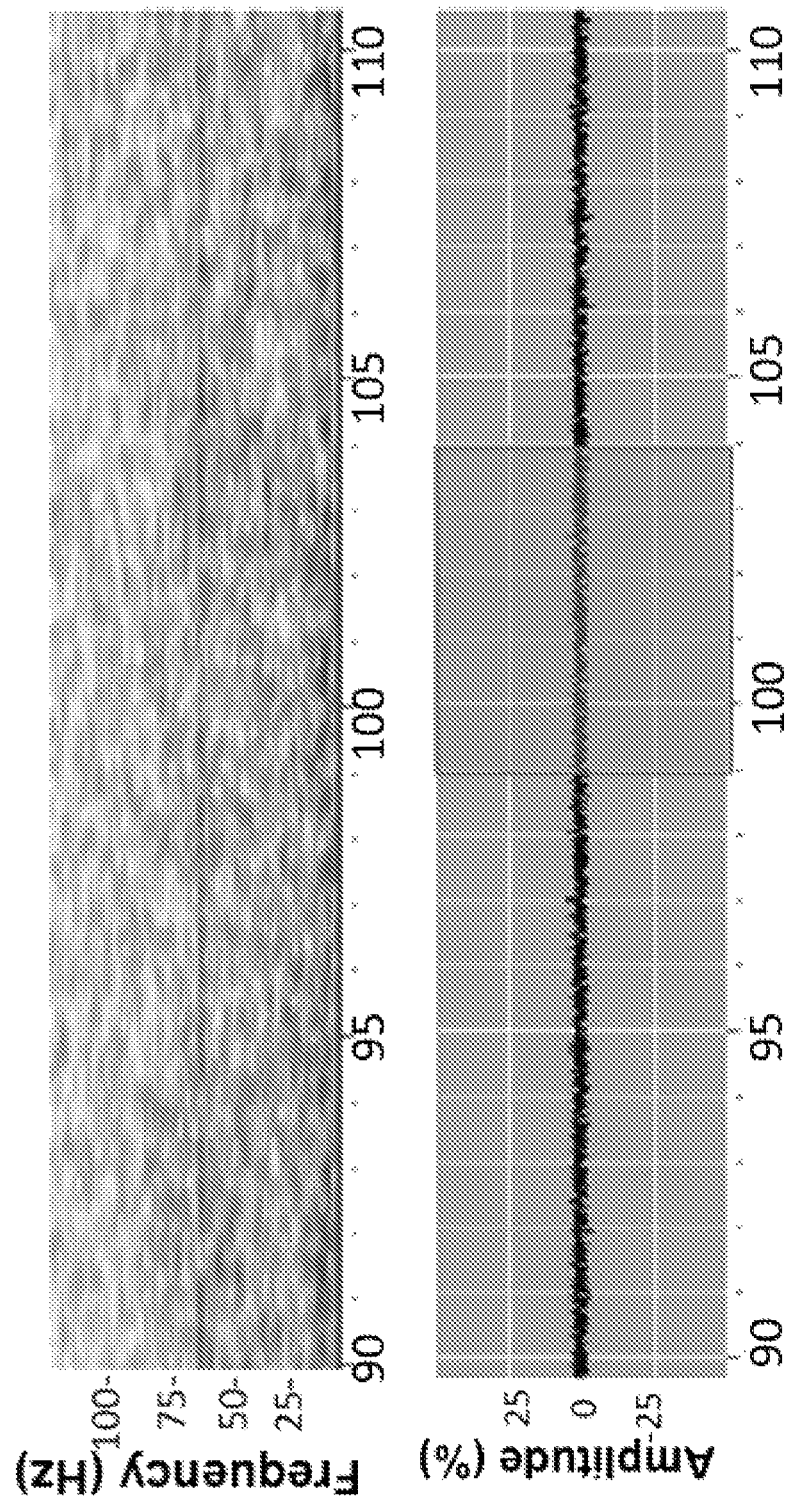
Figure 4B:
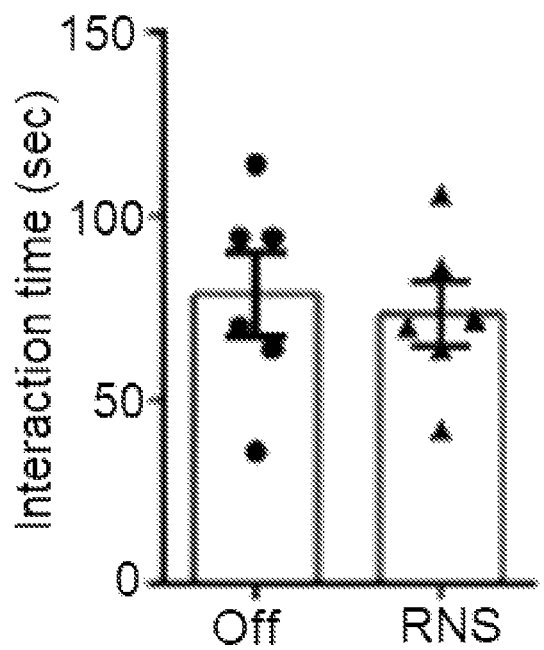

Responsive NAc stimulation could impact other behaviors associated with similar LFP changes to binge-like eating. Notably, the data suggest delta power and NAc stimulation may be able to be quite specific (FIGS. 3A, 4A, and 4B). Nevertheless, experiments to further evaluate this will be similar in design to those used to optimize stimulation parameters, but a pellet composed of sucrose will be used.[4] Chow consumption in a caloric restriction mouse model will also be examined, in order to assess optimized stimulation parameters and LFPs associated with homeostatic feeding.[76] Sex differences will also be re-examined using settings optimized in males. Last, potentially reinforcing and antidepressant properties of these optimized stimulation settings will be re-tested using conditioned place preference and a social juvenile interaction task, as well as the tail suspension tests.[92] These assessments will follow evaluations of optimized parameters and detection settings for binge-like eating in the same cohorts of mice. During these tasks, locomotor, grooming, and drinking behaviors using lickometers will also be assessed to ensure that NAc stimulation does not alter normal behaviors. Real-time LFP data will be recorded during stimulation-off time and analyzed offline to identify associated LFP changes.

Data Analysis:

An investigator blinded to treatment groups will conduct all analyses and verify electrode placement post-mortem. Parametric methods will be utilized to analyze food intake and body weight. The investigation of each of the parameter settings is done in a cross-over fashion as each mouse will have measurements taken with stimulation on and off. For each measurement taken, the paired differences will be calculated and summary statistics for the paired results will be compiled. Basic locomotor activity measurements, conditioned place preference, tail suspension and social interaction data will be summarized for stimulation on and stimulation off, as well as the paired differences between the two.

Example 3: Development of the rRNS

This example will leverage the device development experience of NeuroPace, Inc. and its existing RNS® neurostimulator hardware platform to develop a system that incorporates novel software advances designed to anticipate and attenuate LOC eating.

rRNS System Development and Testing Strategy
(1) Prototype rRNS System Software Algorithm Development/Testing.

This development phase will follow an iterative process. First, test algorithms will be integrated into the prototype rRNS neurostimulator and programmer for use in the closed-loop stimulation system that already exhibits effective detection of the candidate LFP biomarker to attenuate a binge (FIG. 4A). The utility of these algorithms will be assessed once stimulation parameters are optimized, and then refined for implementation in the rRNS.
(2) Finalize rRNS System.

Software development for the rRNS System will follow NeuroPace's product development standard operating procedure. All software features developed will undergo appropriate testing required for the IDE submission.

Key Innovative Claims Proposed for the rRNS System Development.

Sensing and Signal processing: Detection algorithms will support real-time identification of long durations (>2 s) of LFPs such that brief (non-specific) low frequency oscillations from longer oscillations that are currently seen before and during binge-like eating can be differentiated (FIGS. 3A-3F). The rRNS neurostimulator will incorporate the ability to detect LFPs from all 4 channels simultaneously (increased from 2), program more detectors, and combine detectors in different ways. This will enable detection of complex LFP features (e.g. cross-frequency coupling), and increase the span of sampling along the entire length of the NAc. In addition, the ability to uncouple detectors from stimulation will be provided to allow for detection without delivering responsive stimulation during magnet triggered stimulation.

Measurement: The rRNS neurostimulator will be able to store 24/7 measurements. This new information is significant because it will provide an uninterrupted record of measurements that can be used to identify LFP changes associated with a LOC event. For example, the neurostimulator will collect and store average, minimum, and maximum bandpass measurements (1-60 second resolution). This will allow for identification of changes in power, which may be associated with LOC eating. Given increases in power are thought to be predictive of and specific to an upcoming binge (FIGS. 3A-3F), this capability is exceedingly relevant.

Stimulation: The rRNS neurostimulator will incorporate new stimulation capabilities informed by parameter testing described above. Some key algorithms include new triggering methods (e.g. magnet triggered and scheduled) and stimulation burst options (e.g. intermittent bursting). Magnet triggering will enable subjects to trigger stimulation in response to LOC. Scheduled stimulation will allow for intermittent stimulation delivery, and may be informed by magnet swipe, EMA and bite counter timestamped data. As described, the proposed rRNS System will also require software modifications to the physician Programmer, Patient Monitor and Patient Data Management System (PDMS).

Example 4: EFS for Responsive Neurostimulation for LOC Eating

The rRNS neurostimulator will be tested in a limited number (n=10) of subjects with refractory obesity suffering from LOC eating. The study is designed to provide initial safety and feasibility data, and to ensure that new software features in the rRNS perform as intended. This first-in-human study will allow for initial assessments of the behavioral specificity of a candidate LFP biomarker and intermittent NAc stimulation for LOC eating. Feasibility and concordance of controlled and ambulatory assessments of LOC eating will also be evaluated as to how they inform a targeted, post-hoc LFP analysis. Finally, this EFS is designed to provide support for more advanced studies and the continued development of responsive NAc stimulation for LOC eating in obesity.

A brief overview of the Clinical Protocol Synopsis that details the EFS design is provided herewith.

Subjects will undergo extensive psychiatric interviews, involving eating disorder assessments, as well as a diagnostic psychiatric evaluation by a psychiatrist with expertise in NAc stimulation. Applicant will review the results of this screening, which will include an offline assessment of the videoed consent to ensure capacity by an Ethics Advisory Team that has direct experience assessing severely impaired psychiatric patients enrolling in early phase brain device trials.[14,24] Eligible subjects will be enrolled. Following surgery, subjects will start the three strategic phases of the EFS during which they will be seen at least monthly by the contact Applicant and a NeuroPace field engineer joined by a psychiatrist once stimulation is initiated:

Phase 1—Recording only (5 months)
Phase 2—Magnet Triggered Stimulation (3 months)
Phase 3—LFP-Responsive Stimulation (3 months)

The EFS is designed so that 5 months of recordings during controlled and ambulatory assessments (Phase 1) and the first stimulation phase (Phase 2) will occur for the first patient before any subsequent surgeries are performed to provide some initial measure of safety and feasibility for the planned assessments and intervention. In addition, Phase 2 is designed to be initiated after the implant-associated electrode tissue interface variability has resolved.[87] Subjects will be required to attend monthly (weekly during initial stimulation periods) follow-up visits during each of the 3 phases, where medical history, neurological/physical exam, adverse events, body weight, as well as EMA, bite-counter, and magnet-swipe data will be assessed.

Phase 1—Recording Only (4 months). Months 1-4 after implant will consist of LFP recordings and an activity measurement phase using magnet swipes to target LFP analyses. Feeding behavior (normal and LOC meals) will be recorded separately utilizing Ecological Momentary Assessment (EMA) and bite-counter data. Both controlled and uncontrolled (ambulatory) assessments of LOC eating and LFPs will be performed and feasibility of these assessments examined:

Controlled Assessments:

Laptop tasks that evoke changes in striatal fMRI BOLD signal will be used to assay NAc LFPs.[8,55] Real-time LFPs will be streamed to the rRNS programmer, stored and analyzed offline. Commands will be sent from the laptop controlling the tasks to the rRNS programmer to initiate real-time LFP recording and to introduce markers in the LFP records that can be used to line up the LFP records with the task conditions. Synchronized video recordings will be performed.

Behavioral laboratory assessment of LOC eating with real-time recording and LFP streaming.[96] Real-time LFPs will be stored and analyzed offline. Synchronized video recordings will provide additional timestamps for post-hoc LFP analyses. Commands will be sent from the video acquisition computer to the rRNS programmer to initiate real-time LFP recording and to introduce timestamps in the LFP records. Further, the commands will trigger LED lights on the rRNS accessories that can be included in the video frame to allow for data synchronization. These studies will yield human LFPs associated with LOC to optimize a candidate biomarker (FIGS. 3A-3F and FIGS. 4A-4B) and rRNS detection settings for ambulatory LFP recordings.

Uncontrolled (or Ambulatory) Assessments:

Multiple 1-3 min snapshots of LFP activity will be recorded daily. These recordings will be triggered by detection of a candidate LFP biomarker (FIGS. 3A-3F), which was identified and characterized in mice and will be refined by controlled assessments. Snapshots of LFP activity will also be stored in response to magnet swipes and at scheduled times.

Times for scheduling stimulation will be determined on an individual basis using magnet swipe, EMA and bite-counter timestamps to approximate average times of day of normal and LOC meals and time periods without eating.

Subjects will magnet swipe when LOC is sensed, as is routine for EMA logging.[31] Fidelity of magnet swiping will be assessed by reviewing EMA timestamps. The bite-counter may also provide precise timestamps of meal onsets. These multi-modal timestamps together with magnet swipes will facilitate offline LFP analyses targeted to time periods associated with LOC eating.

In addition to LFP snapshots, 24/7 measurement data (e.g. changes in area under the curve) will be captured by the rRNS. Measurements can be used to identify changes in LFP activity associated with LOC eating even in the absence of stored LFPs.

Phase 2—Magnet Triggered Stimulation (3 months). Following a monopolar stimulation assessment at the beginning of month 5 (see below), a contact will be activated unilaterally in monopolar mode that appears to induce the most positive affect for magnet triggered stimulation. The experiments will start with parameters optimized in mice. A limit to the total number and rate of daily swipes will be determined by prior EMA logs, bite-counter data, and magnet swipe timestamps. Stimulation parameters and detection settings may be adjusted at weekly-monthly clinic visits based on clinical judgment of each participant's progress, LOC logs, eating disorder questionnaires, and adverse effects (Table 2). The contralateral lead will be activated after the first week of stimulation once safety is confirmed as is standard in the OCD DBS protocol. Behavioral lab assessments will be repeated, and subjects will be allowed to trigger stimulation during LOC for further optimization of LFP detections and stimulation parameters. LFPs and activity measurements will continue to be stored for offline LFP analyses as will EMA logs and bite-counting for LFP biomarker characterization (Phase 3).

TABLE 2

Staged stimulation-on with weekly-monthly clinical safety monitoring phases with stim-off to ensure safety of intermittent NAc stimulation.

| 1 week | 1 week | 2 weeks | 1 week | 4 weeks |
|---|---|---|---|---|
| Stim-on | Stim-off | Stim-on | Stim-off | Stim-on |

Phase 3—LFP-Responsive Stimulation (3 months). Detection algorithms will be used to sense and store LFP biomarkers characterized in Phases 1 and 2 and will be optimized for each subject. Stimulation will be delivered only when the biomarker is detected, and magnet swipe timestamps, EMA logs and bite-counting will continue. Stimulation parameters will be based on optimized parameters above that are refined in Phase 2. Laptop tasks and the LOC eating lab will be used to assay detector and stimulation sensitivity in a controlled setting in the beginning of this phase.

Surgical Procedure.

The standard frameless stereotactic approach will be used to target the NAc.[12] Each depth lead has 4 independently programmable cylindrical electrode contacts. Per the targeting protocol for OCD surgery, the distal-most contacts (0,1) are expected to be in ventral and central NAc, and contact 2 in caudal NAc (and partially the anterior commissure). The dorsal-most contact (3) will be at the ventral margin of the anterior limb of the internal capsule (FIG. 2B). Sedation is administered, and the head is prepped, and draped. Incisions are made, and disposable stereotactic navigation hardware is placed. The outer cannula is placed into the brain 20 mm above the target on the first side. A microelectrode (10 µm at the tip) is advanced stepwise, continuously recording single- and multi-unit activity for 1 min every 1 mm to physiologically define the NAc. This is repeated contralaterally. Once the depth leads are implanted, and a monopolar assessment is conducted, intraoperative imaging is obtained to confirm accuracy. Once confirmed, the leads are secured in place using the NeuroPace burr hole covers, and a small right parietal craniotomy (2×4 cm) is made for the rRNS neurostimulator. The depth leads are connected to the device and an impedance check is performed as well as real-time LFPs to confirm a functioning rRNS system.

Monopolar Assessment.

In the operating room and immediately prior to initiating Phase 2 of the EFS, monopolar test stimulation will be performed, starting with the ventral-most electrode. Stimulation is initiated and titrated per the optimized parameter findings and using current intensity ranges from the standard OCD DBS protocol. The anticipated effects are elevations in mood, facial expressiveness, and even heart rate. Patients who will be blinded to test conditions are asked to report their mood, anxiety, and alertness verbally using 10-point scales. Stimulation is tested for approximately 2 min with the subjects blinded, interspersed with periods of no stimulation. Initially, the current amplitude will be set at 0.5 mA less than the lowest amplitude needed to induce a positive affective response.

Data Analysis.

This is a small EFS aimed at assessing safety and feasibility of responsive neurostimulation for LOC eating. This small feasibility study is not powered or intended to test any statistical hypotheses. Results, per patient, will be described using standard summary statistics, evaluating outcomes at each visit and assessing changes from baseline. Standard summary statistics will also be generated for results across the ten subjects. Outcomes described will include safety, feasibility, and preliminary efficacy assessments. Descriptive statistics will be provided to evaluate changes within subject for LOC and mood assessments taken before and after an eating episode. The results obtained from multi-modal ambulatory assessments of LOC episodes using magnet swipes, EMA, and bite counters will be assessed for their congruence. The relationship among these measures will be evaluated graphically and the Spearman and Pearson correlation coefficients will be calculated. The feasibility of calculating the performance of LFPs as predictors of LOC episodes will be examined using each of these three separate assessment approaches. Diagnostic accuracy will be calculated for each method.

Safety and Tolerability.

Safety assessments include treatment-emergent adverse event documentation, weekly-monthly monitoring visits, psychiatric assessments, the Columbia-Suicide Severity Rating Scale, vital signs, body weight, labs, and overall nutrition throughout the study. Weight is recorded using a calibrated scale in shoeless participants, rounded to the nearest 0.5 pounds, and converted to kilograms (to convert, multiply by 0.45) for data reporting. Two additional clinical evaluations are budgeted per patient during the stimulation phases of the study to further support any untoward side effects of NAc stimulation, as well as a neuropsychology visit for any unanticipated cognitive effects.

LFP Biomarker Identification.

Snapshots of LFP activity as well as 24/7 LFP activity measurement data will be recorded and downloaded daily from the device by each subject and uploaded to a secure web-based data management system. The data will be analyzed by NeuroPace to assess LFP changes associated with LOC eating. Clustering algorithms may be used to differentiate LFP features associated specifically with LOC eating. The results of the analyses will then be displayed on a web-based system for the investigators. The analyses will update as new data are uploaded providing near real-time identification of biomarkers. A similar data analysis approach has been successfully implemented for the analysis of seizure LFP activity in animal models by NeuroPace.[17] Identical methods will be used to identify biomarkers in the continuous real-time LFP data collected during controlled assessments. LFP analyses informed by LOC eating logs will be conducted in all three phases of the clinical study. As stimulation only will be delivered intermittently (in response to magnet swipe or an LFP biomarker), NeuroPace will be able to assess LFP activity between stimulations. Over the course of a day, the total amount of stimulation is anticipated to be less than 5 mins. During stimulation phases, the rRNS settings will be adjusted to minimize sample loss during stimulation allowing for near-concurrent sense and stimulation (FIG. 6). The capability for near simultaneous sensing and stimulation may also provide a physiologic read-out for titrating stimulation parameters in the clinic using laptop-based tasks.

Example 5: Closing the Loop on Impulsivity Via Nucleus Accumbens Delta Band Activity in Mice and Man Abstract. Reward hypersensitization is a common feature of neuropsychiatric disorders, manifesting as impulsivity for anticipated incentives. Temporally specific changes in activity within the nucleus accumbens (NAc), which occur during anticipatory periods preceding consummatory behavior, represent a critical opportunity for intervention. However, no available therapy is capable of automatically sensing and therapeutically responding to this vulnerable moment in time when anticipation-related neural signals may be present. To identify translatable biomarkers for an off-the-shelf responsive neurostimulation system, we record local field potentials from the NAc of mice and a human anticipating conventional rewards. We find increased power in 1-4 Hz oscillations predominate during reward anticipation, which can effectively trigger neurostimulation that reduces consummatory behavior in mice sensitized to highly palatable food. Similar oscillations are present in human NAc during reward anticipation, highlighting the translational potential of our findings in the development of a novel treatment for a major unmet need.

We reveal prominent delta oscillations in the nucleus accumbens preceding food reward in mice, and use them to guide responsive neurostimulation to suppress binge-like behavior. Similar electrographic signatures are observed in human nucleus accumbens during reward anticipation as well, suggesting their translational potential in the development of a novel treatment for a major unmet need.

Introduction. Impulsivity is one of the most pervasive and disabling features common to many disorders of the brain (1-3). Heightened responsivity in the nucleus accumbens (NAc) during anticipation of a rewarding stimulus predisposes to impulsive behavior, which can have severe implications for development of maladaptive behaviors (4-8). Notably, electrophysiological, neurochemical and functional neuroimaging correlates have been reported in multiple species during brief windows of anticipation (5, 9-13). These correlates (or biomarkers) that precede a "moment of weakness" have potential to inform a novel therapeutic to deliver a time-sensitive intervention.

Recently, a responsive neurostimulation (RNS®) system was approved by the United States Food and Drug Administration for adjunctive treatment of partial onset seizures (14). This novel intracranial closed-loop system has proven capable of detecting epileptiform activity and preventing propagation by responsively delivering electrical stimulation directly to the seizure-onset zone. Here, we examine the potential for RNS® to intervene during a vulnerable period immediately preceding receipt of highly rewarding stimuli, an undertaking that has immediate translational potential given the availability of this novel system. We leveraged the finding that electrically stimulating the NAc in mice anticipating a food reward effectively attenuates binge-eating behavior (15). To "close the loop" on this intervention using an automatic stimulatory system, however, the identification, characterization, and refinement of an anticipatory biomarker is a critical next step.

Given the currently approved RNS® system is limited to local field potential (LFP) recordings due to its implanted depth macroelectrodes' spatial resolution, we make LFP recordings from the mouse and human NAc during a period of reward anticipation, and find prominent delta oscillations elicited during anticipation of a highly rewarding stimulus. Multi-unit analysis reveals strong correlations between delta oscillations and unit activities in the NAc. Utilizing this translational biomarker as a trigger, RNS® blocked binge eating in mice with remarkable behavioral specificity, thereby taking the first critical step towards the development of a targeted intervention for neuropsychiatric patients suffering from hypersensitivity to pathological motivations.

Results

Figure 9A:
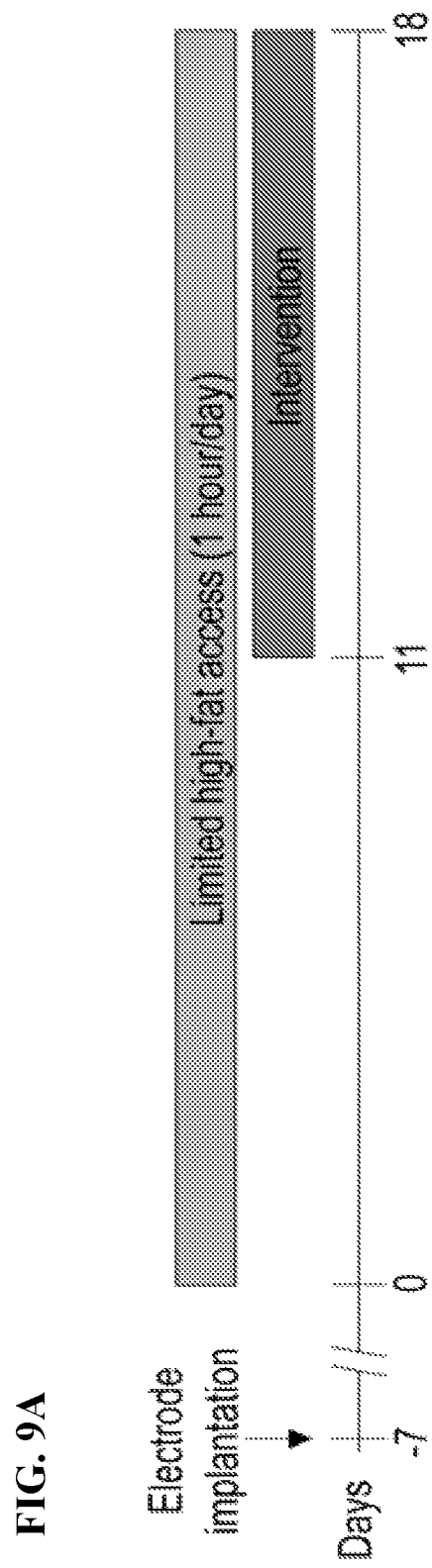
FIGS. 9A-9G: Schematic of the Animal Experiment, Histology, Electrode Design, and High-Fat (HF) Intake Summary.
Figure 9B:
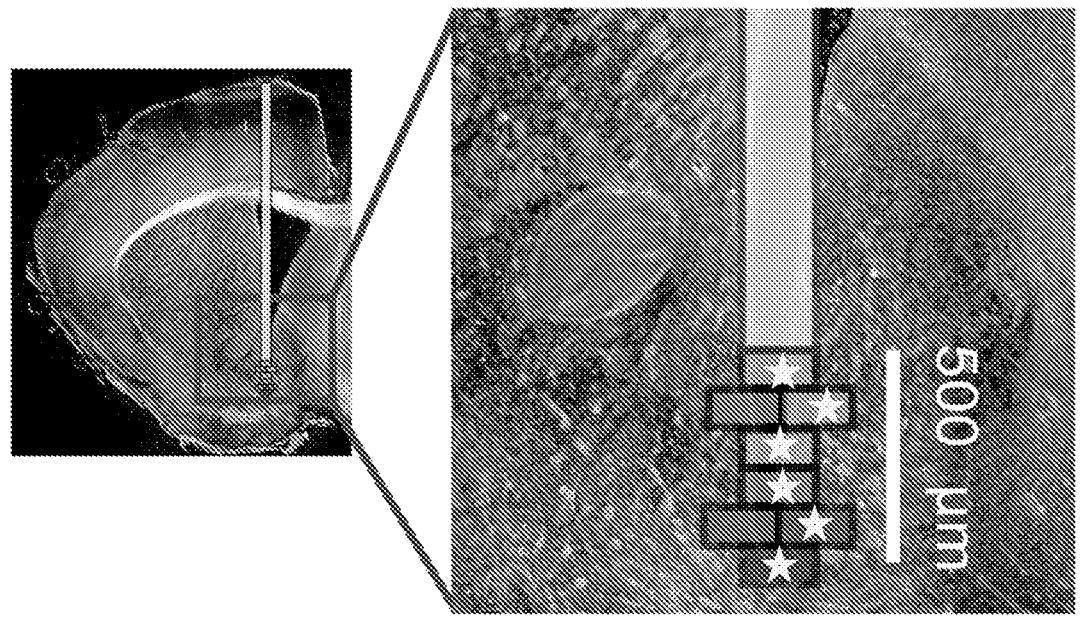
Figure 9C:
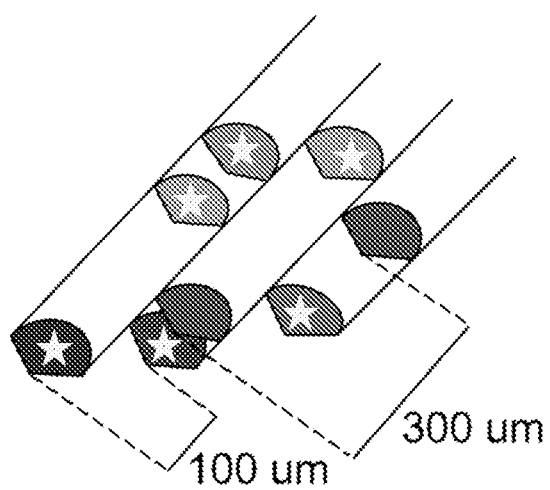
Figure 9D:
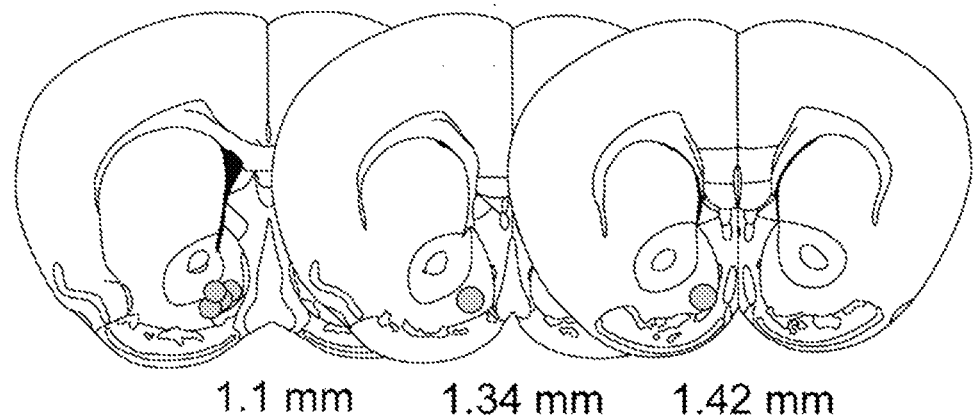
Figure 9E:
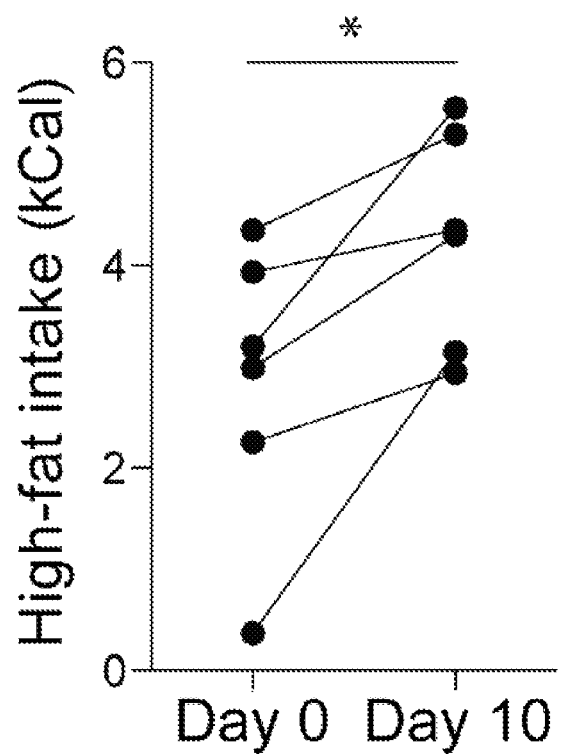
Figure 9F:
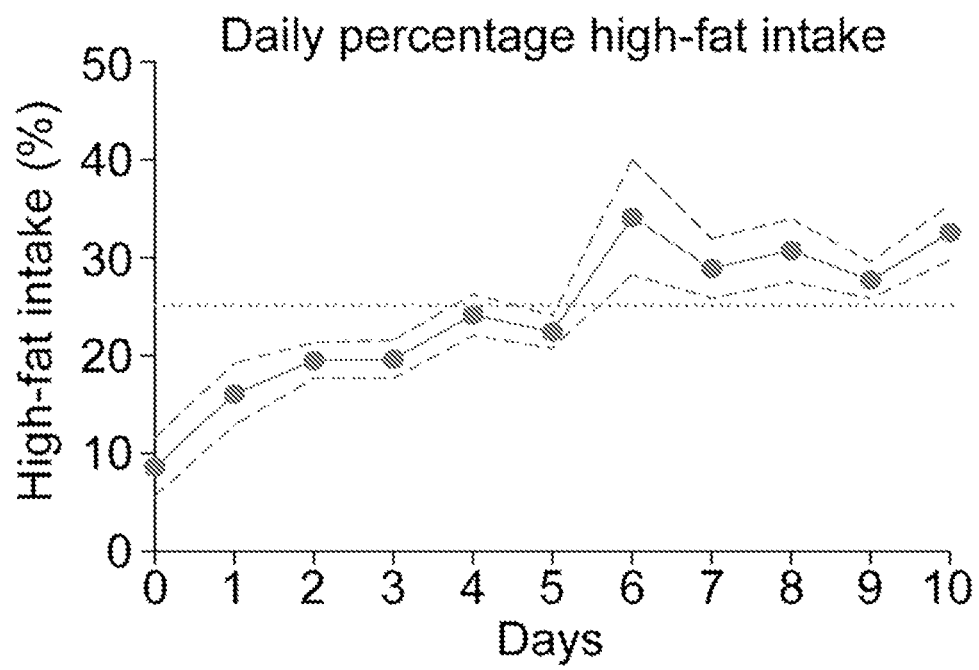
Figure 9G:
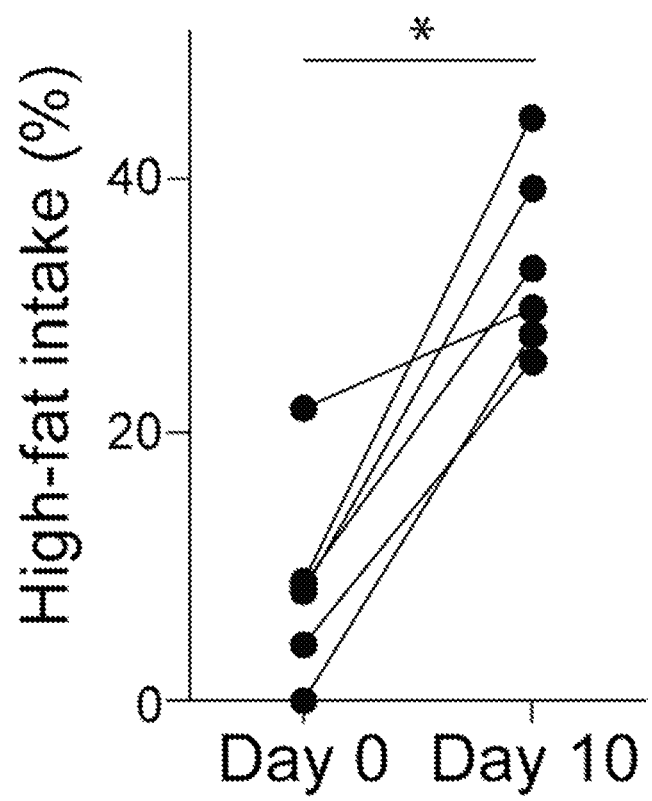
Figure 10A:
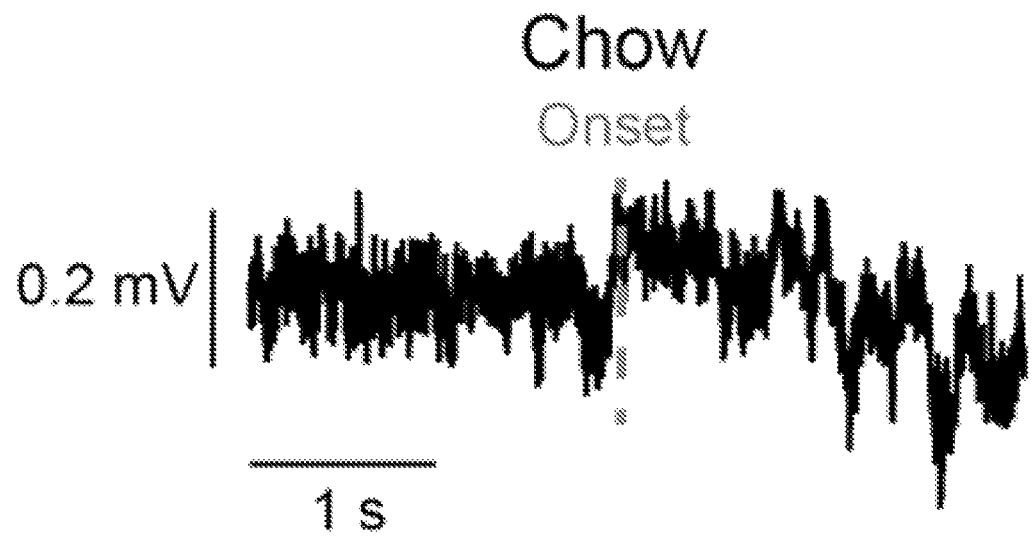
FIGS. 10A-10L: Raw Local Field Potentials (LFPs), Power Spectral Density, Time-Frequency Analyses of the Nucleus Accumbens (NAc) LFPs, Delta Power Characterization, and System Block Diagram of the Responsive Neurostimulation Setup.
Figure 10B:
Figure 10C:
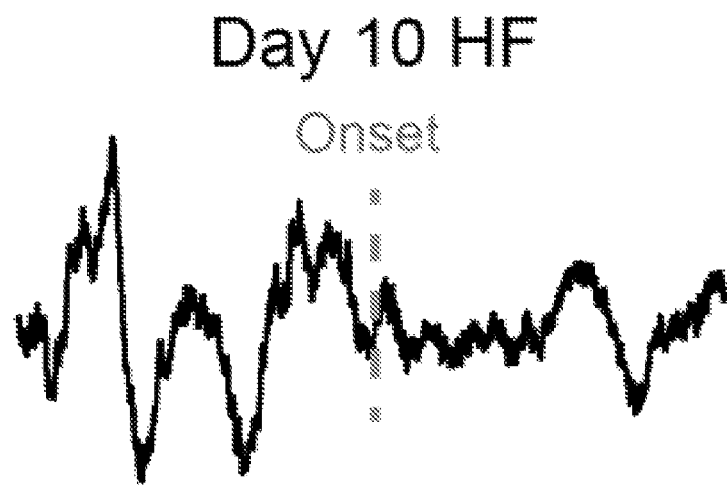
Figure 10D:
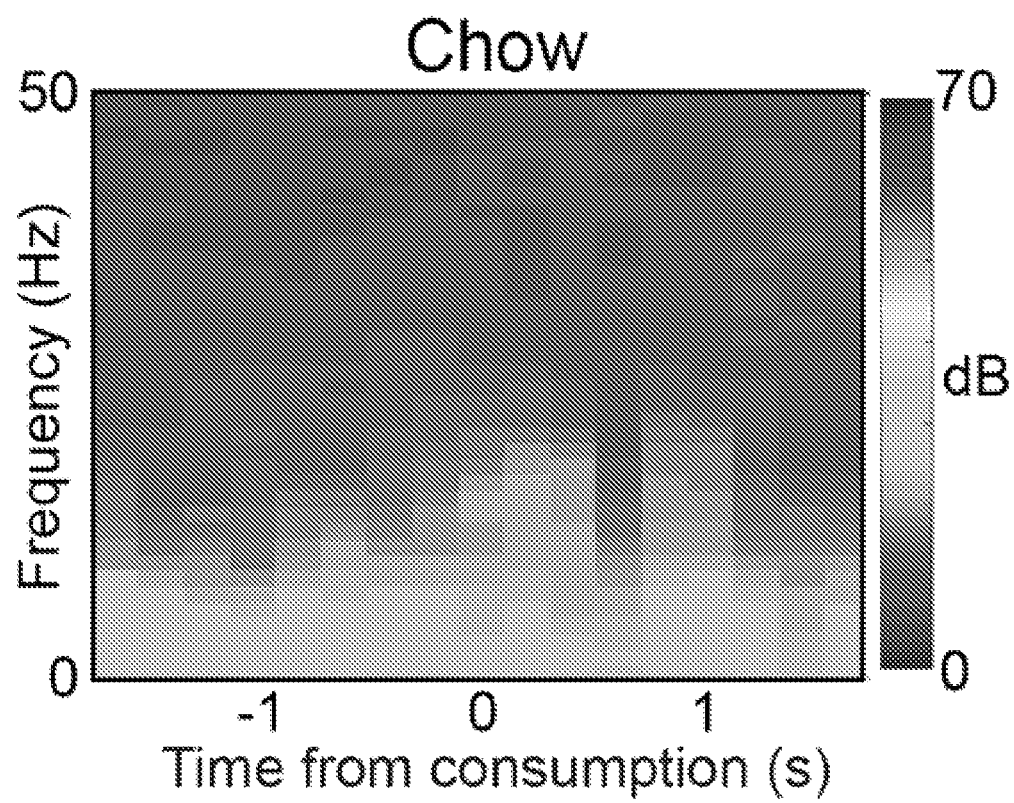
Figure 10E:
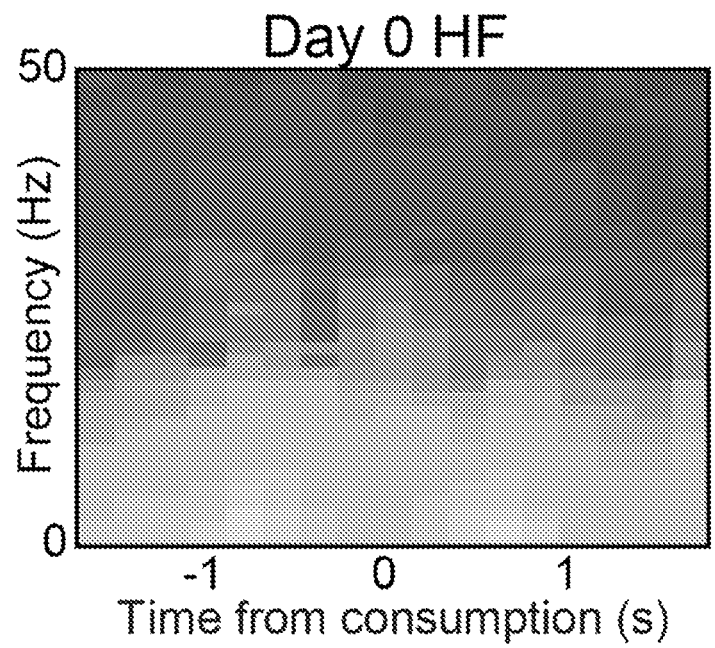
Figure 10F:
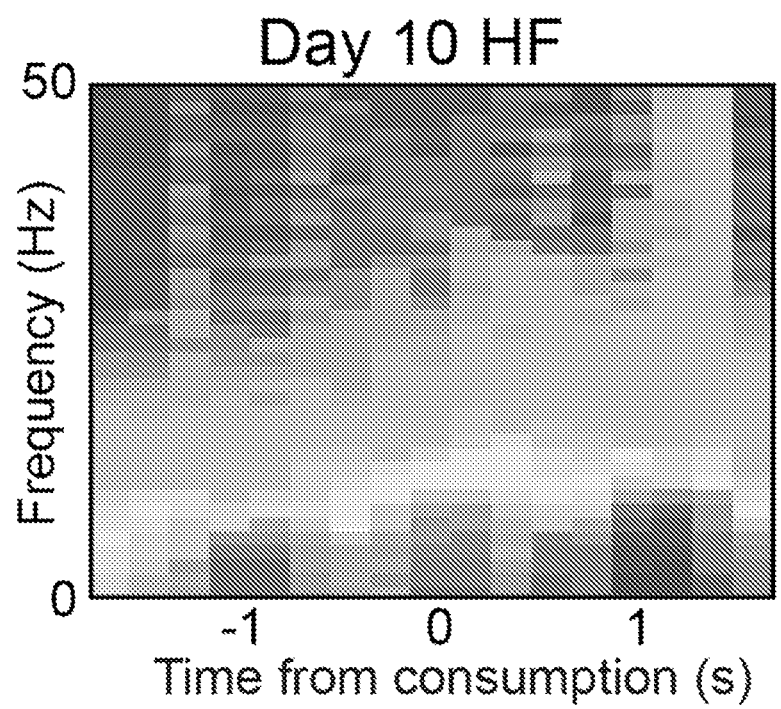
Figure 10G:
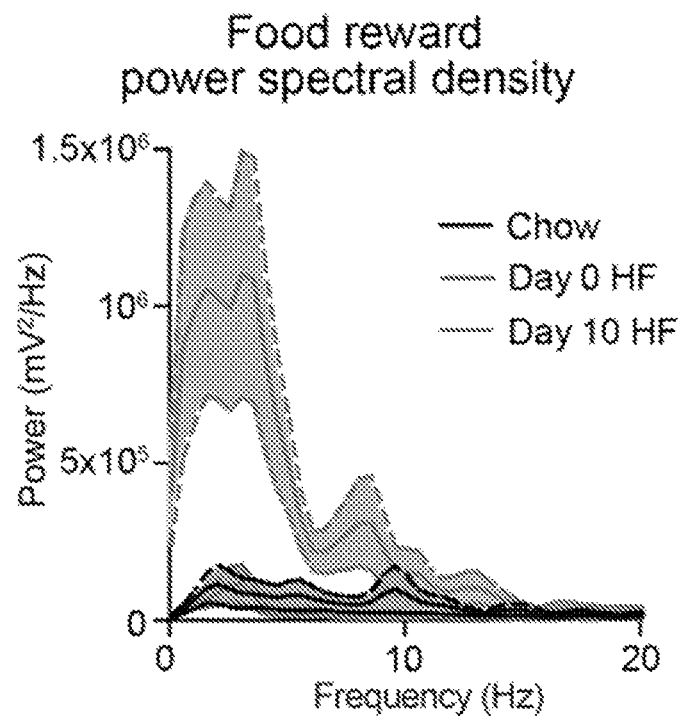

Increase in NAc Delta Range Field Potentials Precedes Binge Eating in Mice. Multielectrode arrays were implanted into the NAc of mice (n=6) (FIGS. 9A-9D). Following a 1-week recovery period, these mice were put on a protocol of 1-hr daily exposure to high fat (HF; standard house chow ad libitum) known to induce binge-like eating behavior (defined as consumption of >25% of daily caloric intake from HF; FIGS. 9E-9G). Given prior reports across species of changes in NAc cell firing during reward anticipation (13, 16, 17), mouse NAc LFPs were recorded daily for 2 hours, 1 h before and 1 h during limited-exposure to HF food. All mice reached criterion for stable binge eating by day 10 (<10% variation across 3 consecutive days) (15). Power spectral density analyses of NAc LFPs averaged across mice immediately before (2-second window across 4-second epoch, which covered from 2-second before to 2-second after the onset of a binge, This window was utilized as we were attempting to interrupt a brief vulnerable window in time immediately prior to a pathological impulse such as binge.) HF intake on days 0 and 10 were carried out. As a control, identical analyses were performed immediately before the mice ingested standard chow (FIGS. 10A-10C).

Figure 10H:
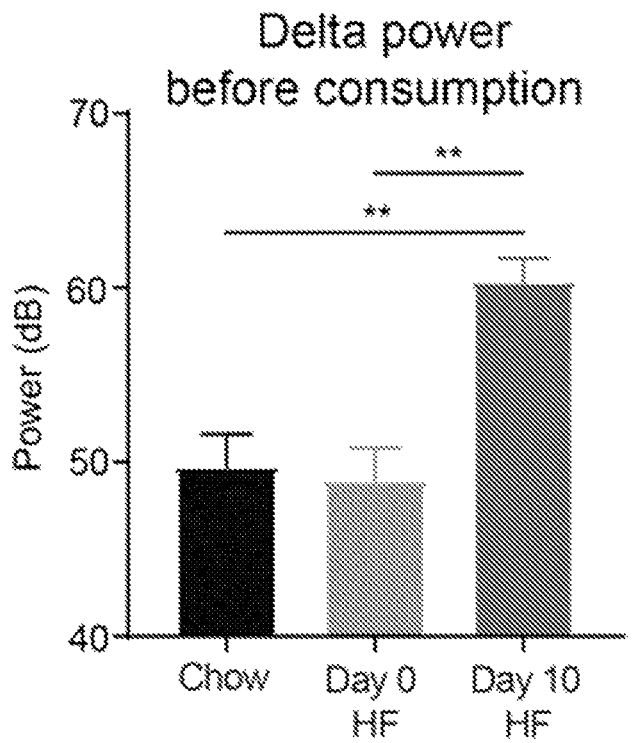

The most robust change in LFPs was increased power in very low frequency (delta) oscillations once binge eating developed on day 10 immediately prior to HF intake (FIGS. 10D-10H). Mean time-frequency spectrograms and comparison of individual frequency bands (delta: 1-4 Hz, alpha: 4-8 Hz, theta: 8-12 Hz, beta: 12-30 Hz, gamma: 30-50 Hz) confirmed that the only statistically significant change in spectral power occurred in the delta frequency range immediately prior to HF intake after the development of binge-like behavior, compared to baseline (day 0) HF and chow control (delta: $F=6.165$, $P<0.001$; Tukey post hoc test: chow vs day 0 HF: n.s., chow vs day 10 HF: $P<0.01$, day 0 HF vs day 10 HF: $P<0.01$; FIG. 10H. Alpha, theta, beta and gamma, chow vs day 10 HF: n.s.). This increase in power in the delta range was not detected immediately prior to chow intake, suggesting it was not related to movement or bite artifact.

Figure 10I:
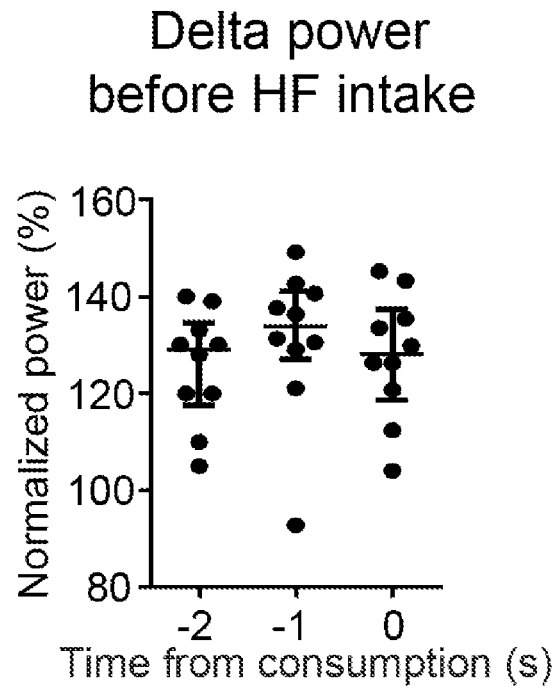
Figure 10J:
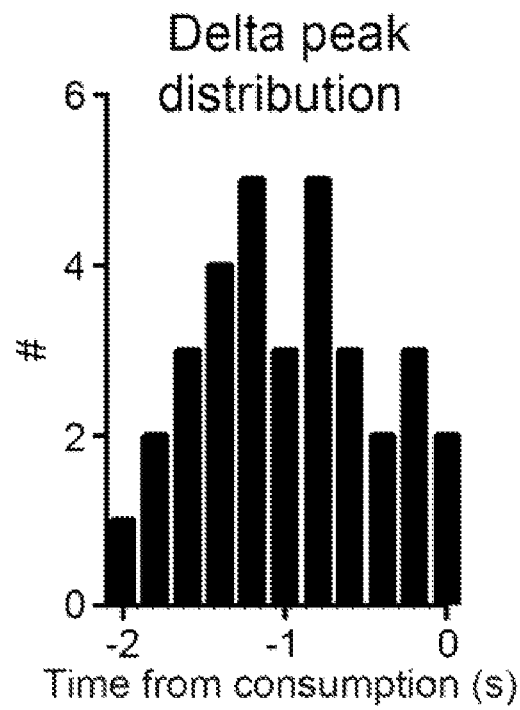
Figure 10K:
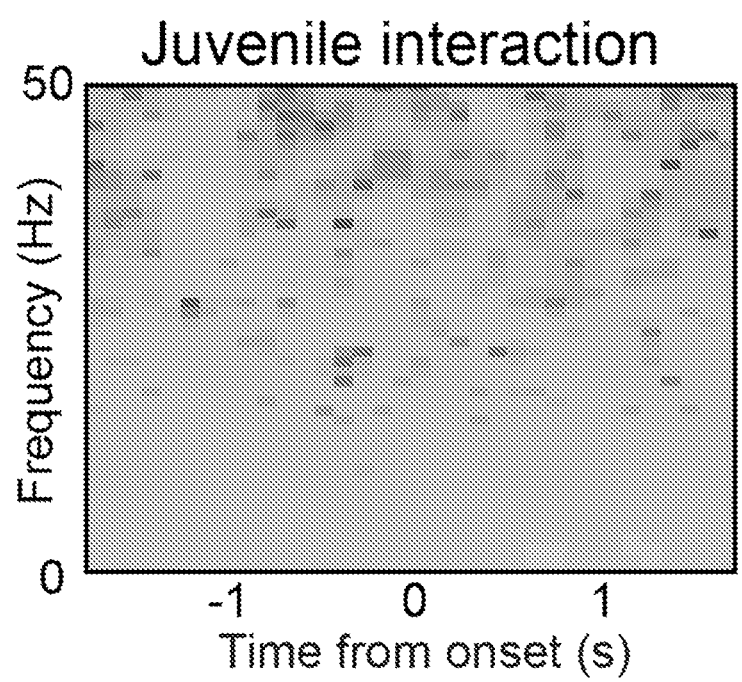
Figure 14:
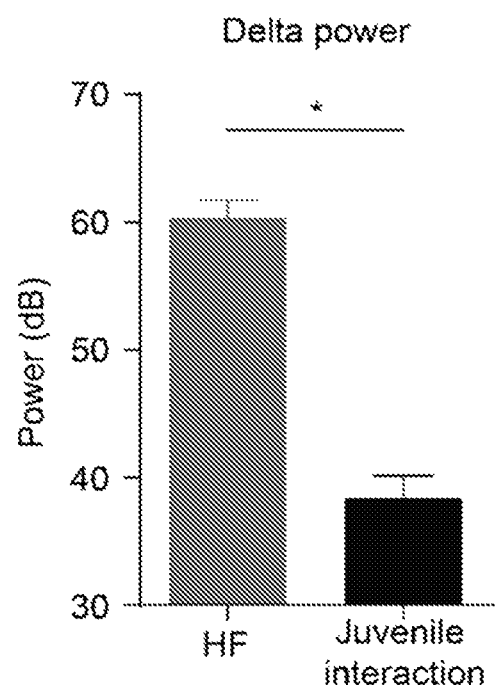
FIG. 14: Related to FIGS. 10A-10L. Delta power prior to the immediate onset of HF intake was significantly higher than delta power prior to the immediate onset of juvenile interaction. In this figure, "*" indicates p<0.05.

We next compared the delta power immediately prior to HF consumption on day 10 with that during the entire 1-hour exposure to HF. NAc delta oscillations normalized to the entire 1-hour period of HF exposure revealed a 30% increase in power during the 2 second window before onset of HF consumption (FIG. 10I). Analysis of delta power peak distribution, revealed a peak at approximately 1 second prior to the onset of HF consumption (FIG. 10J). To further test if the increase in delta power was specific for this highly appetitive food, we recorded LFPs immediately prior to the interaction of the experimental mice with a novel juvenile, an appetitive experience with a finite, definable onset (FIG. 10K). Delta power was significantly lower prior to the onset of juvenile interaction compared to the time period prior to onset of HF intake ($T(35)=2.719$, $P<0.05$; FIG. 14). Together these results suggest that an increase in delta power in LFPs recorded from the NAc precede intake of HF in binge-eating mice and therefore may be a useful biomarker to trigger RNS®.

Figure 10L:
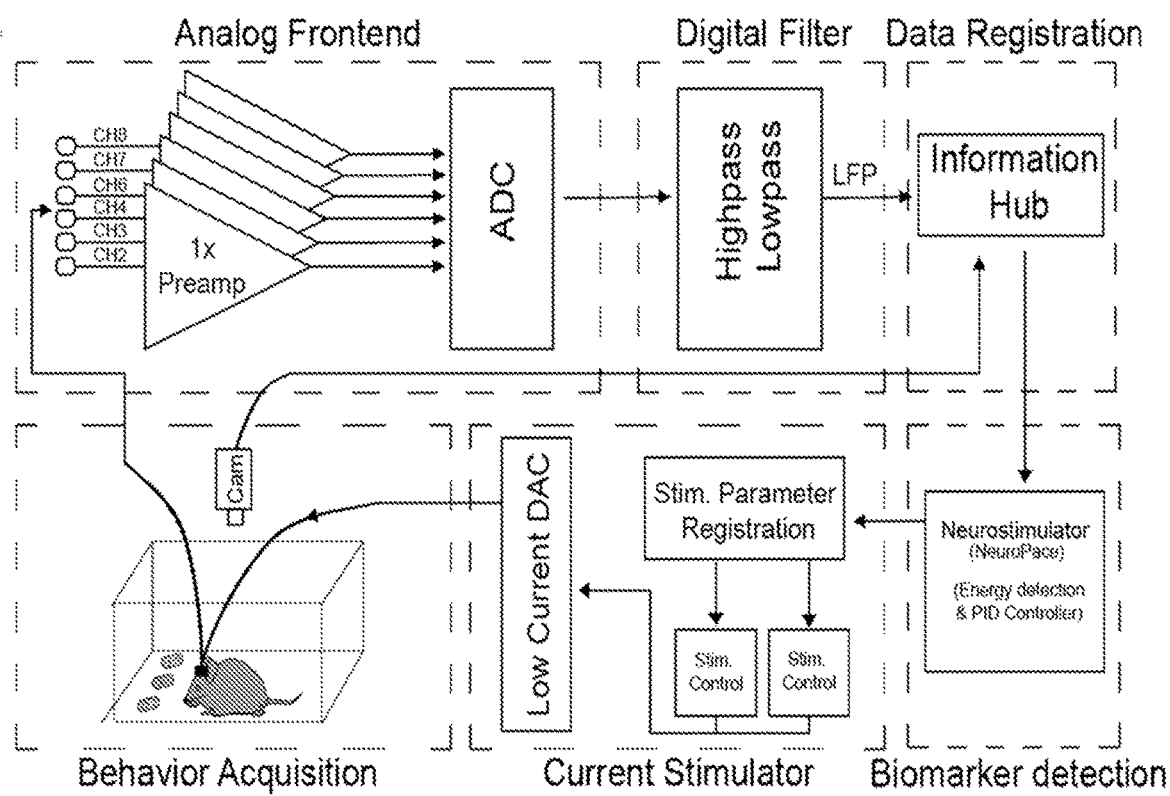
Figure 11A:
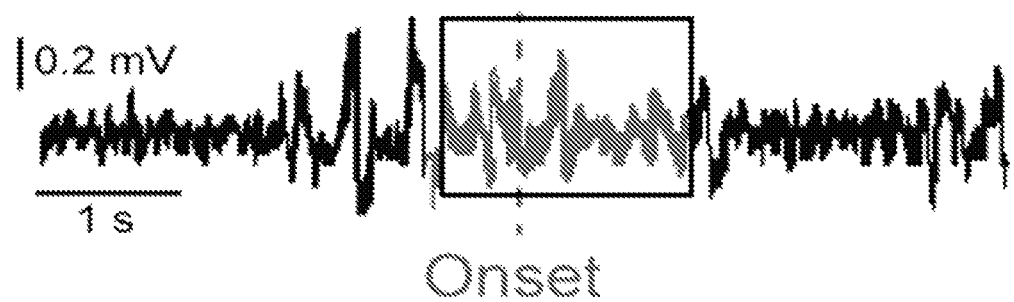
FIGS. 11A-11M: Schematic of the Intervention Period during Limited High-Fat (HF) Access in Mice, and Result Summary of Different Electrical Stimulation Protocols on HF Intake and Juvenile Interaction.

Delta Oscillations as a Biomarker for Responsive Neurostimulation. Based on the previous findings, we assessed whether a delta power threshold could serve as a biomarker to optimize RNS® to attenuate HF intake in mice. The closed-loop system (FIG. 10L) was set to trigger whenever delta power exceeded a predefined threshold based on delta peak distribution and power analyses (a threshold of 20% higher than baseline delta power was used, or 1 standard deviation below the mean power immediately prior to the onset of HF intake, FIG. 10I). When this threshold was reached, electrodes delivered a bipolar, biphasic, 0.1 mA stimulation at 130 Hz for 10 seconds (FIG. 11A). We compared the efficacy of RNS® with that of other neurostimulation protocols in the same experimental animals. Specifically, we also tested: (1) continuous electrical stimulation during the entire 1 hour exposure to HF, a pattern of stimulation commonly referred to as deep brain stimulation (DBS; 130 Hz, 0.1 mA, bipolar, biphasic), (2) manually-triggered stimulation during which an experimenter remotely observed the subjects' behavior via video-monitoring and triggered electrical stimulation (130 Hz, 0.1 mA, 10 seconds, bipolar, biphasic stimulation) at the immediate onset of HF consumption, and (3) random stimulation during which bouts of stimulation (130 Hz, 0.1 mA, 10 seconds, bipolar, biphasic stimulation) were delivered randomly throughout the entire 1-hour HF exposure such that the total number of stimulation bouts matched that delivered during the RNS® protocols.

Figure 11B:
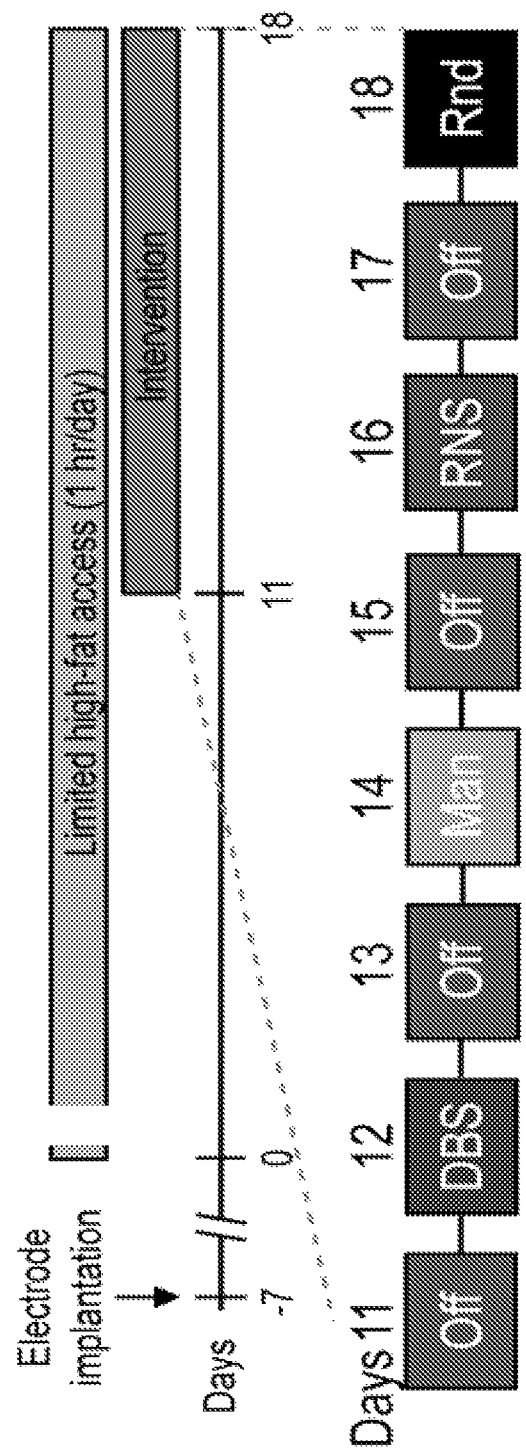
Figure 11C:
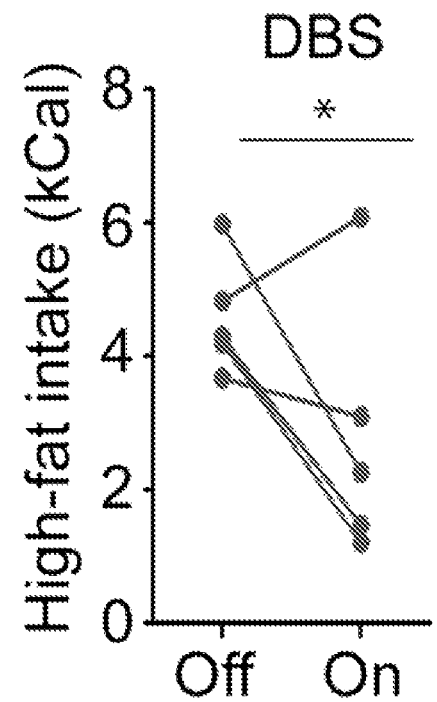
Figure 11D:
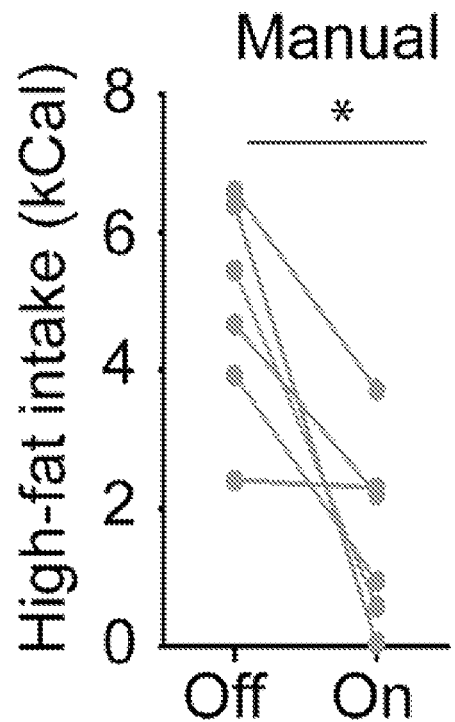
Figure 11E:
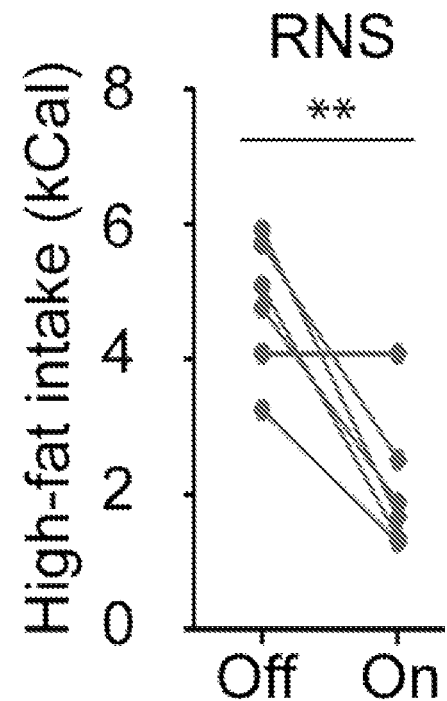
Figure 11F:
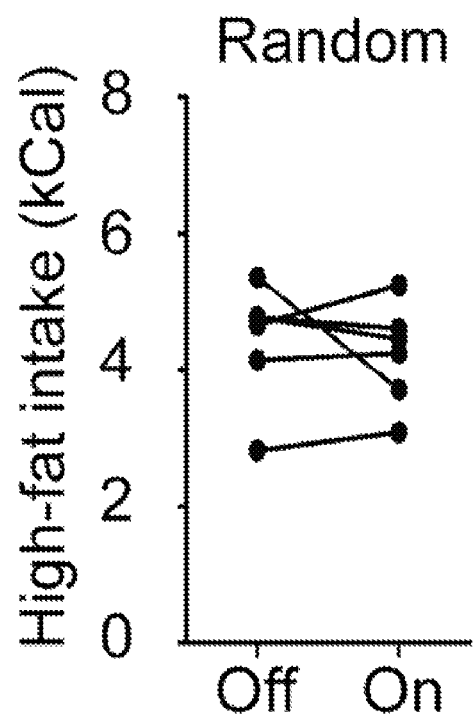
Figure 11G:
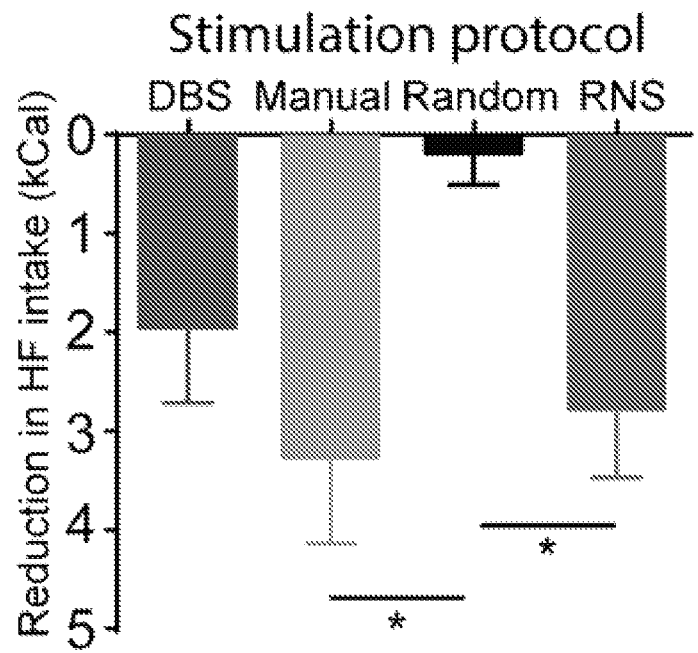
Figure 11H:
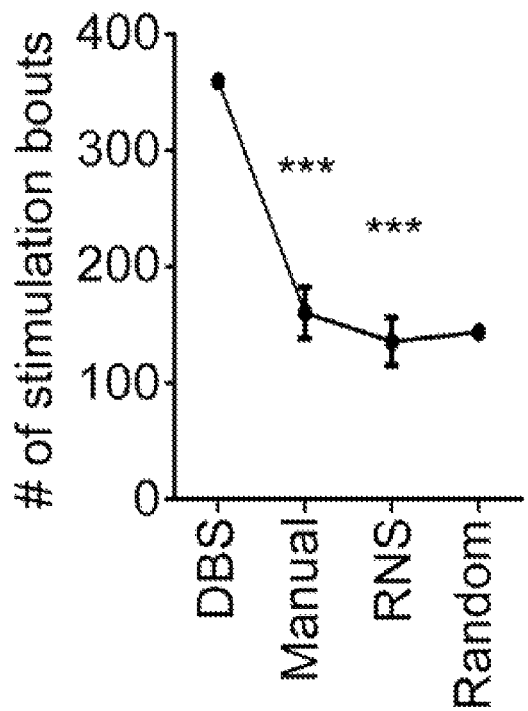
Figure 15A:
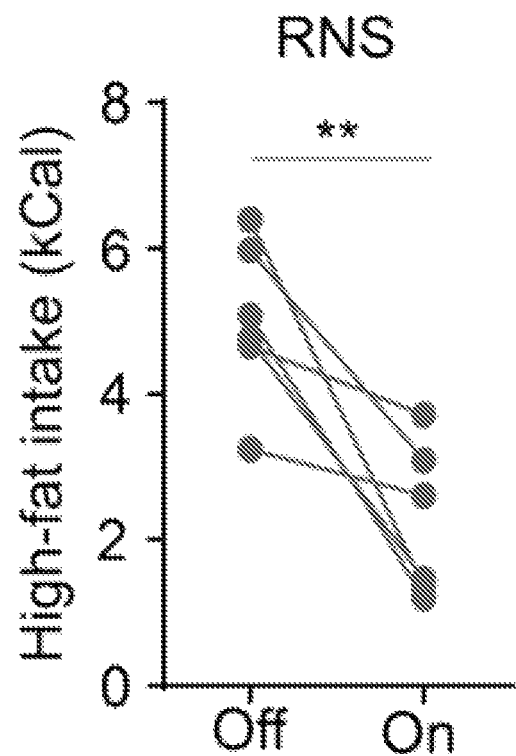
FIGS. 15A-15B: Related to FIGS. 11A-11M.

To ensure that caloric intake from HF returned to baseline in between the stimulation days, each session was followed by a stimulation-off period (FIG. 11B). All the stimulation protocols significantly reduced HF intake except random stimulation (FIGS. 11C-11F; DBS $T(5)=2.58$, $P<0.05$; manual $T(5)=3.75$, $P<0.05$; RNS® $T(5)=4.29$, $P<0.01$; random $T(5)=0.62$, $P=0.56$). At the end of these experiments, we repeated another session of RNS®, which reproduced the previously seen significant decrease in HF intake ($T(5)=3.999$, $P<0.01$; FIG. 15A). We compared the reduction of HF intake between each stimulation protocol, and found that the reductions in HF intake induced by manual stimulation and RNS® were significantly more robust than random stimulation (sphericity assumed, $F(4)=7.034$, $P<0.01$; post-hoc: Manual vs Random: $P=0.042$, RNS® vs Random: $P=0.029$, DBS vs Random, DBS vs Manual, DBS vs RNS®, Manual vs RNS®: n.s. Bonferroni corrected; FIG. 11G). Furthermore, the number of bouts of stimulation used for manual and RNS® were significantly lower than DBS ($F(1.566, 7.813)=65.80$, $P<0.0001$; post-hoc: DBS vs manual: $P<0.0001$, DBS vs RNS®: $P<0.0001$, RNS® vs manual: n.s. Tukey's correction applied; FIG. 11H).

Figure 11I:
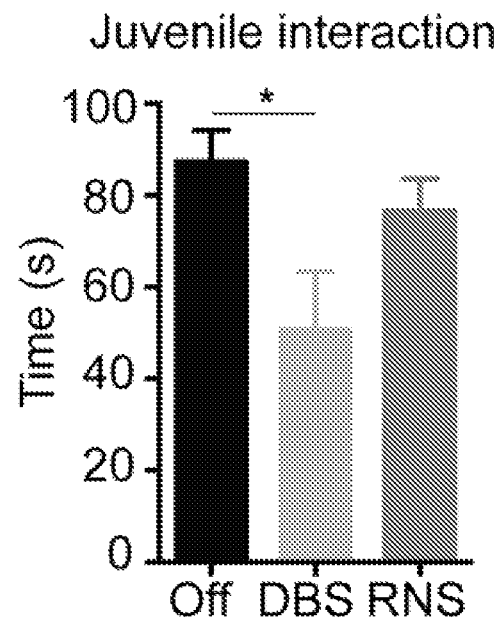
Figure 11J:
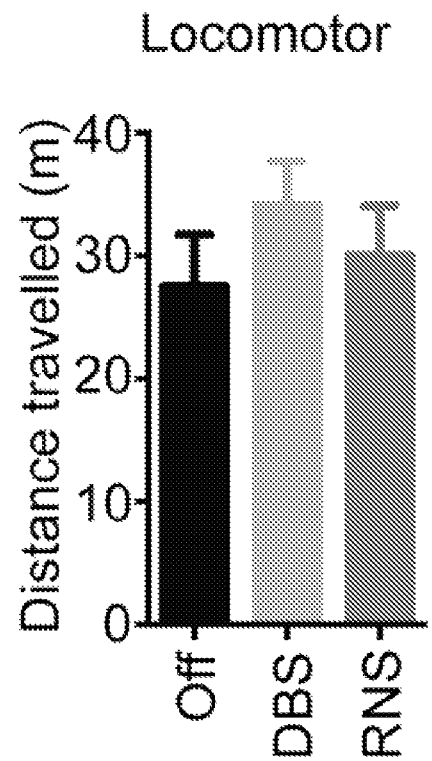
Figure 11K:
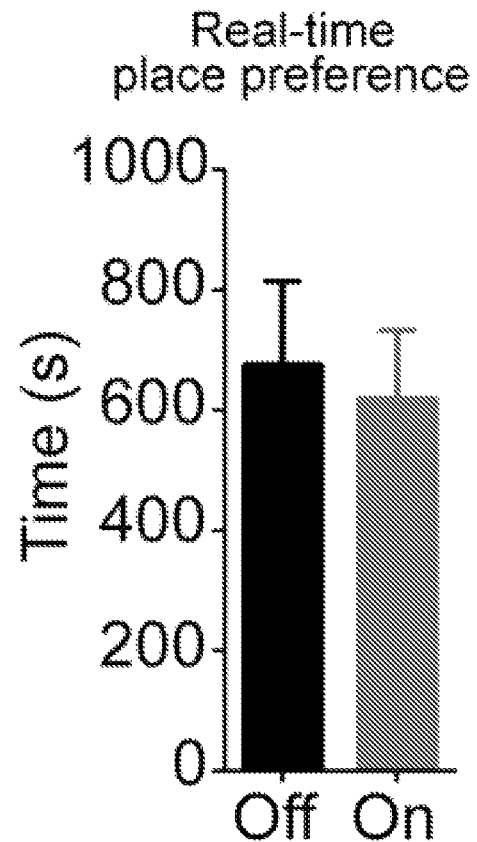
Figure 11L:
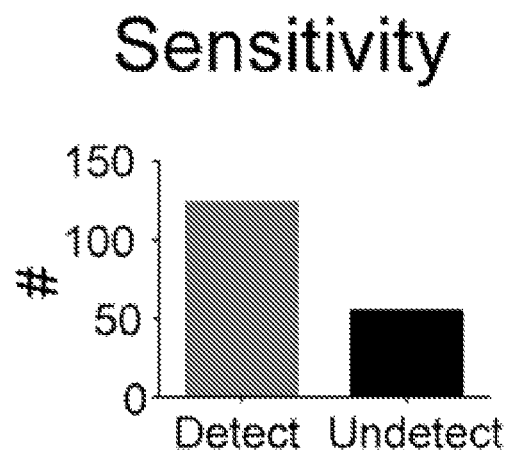
Figure 11M:
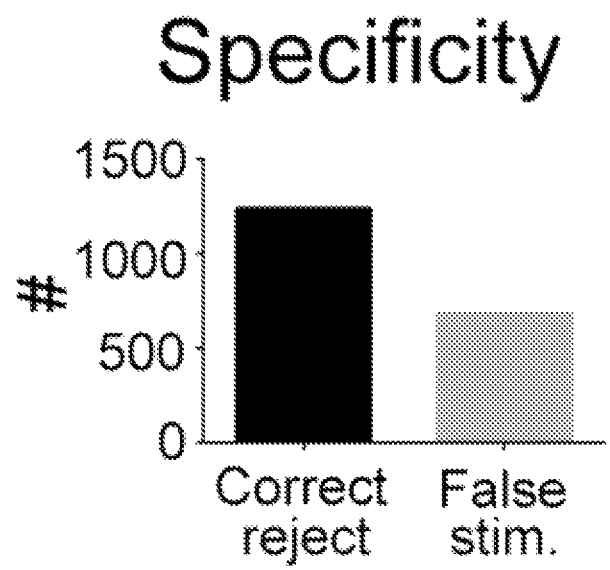
Figure 15B:
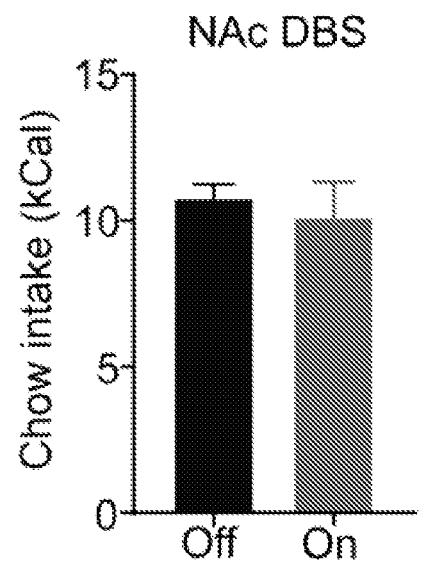

We conducted a number of additional behavioral assays to determine whether RNS® of the NAc might have detrimental side effects. While DBS of the NAc significantly reduced the time spent socially interacting in a juvenile interaction task, RNS® using the same delta band power threshold as a trigger had no significant effect on interaction time ($F(2, 21)=4.557$, $P<0.05$; post-hoc: Off vs DBS, $P<0.05$; Off vs RNS® and RNS® vs DBS, n.s. Tukey's correction applied; FIG. 11I). The number of electrical stimulation bouts during RNS® was again significantly lower than DBS ($T(5)=16.15$, $P<0.0001$, data not shown). Spontaneous locomotor behavior during the limited-exposure HF protocol was not affected by DBS nor RNS® ($F(1.699, 8.493)=0.891$, $P=0.429$; FIG. 11J). Furthermore, NAc stimulation (130 Hz, 0.1 mA, continuous, bipolar, biphasic stimulation) did not induce real-time place preference ($T(5)=0.2283$, $P=0.8285$, FIG. 11K). These results suggest that RNS® of the NAc is neither reinforcing nor aversive, and its effects can block consumption of HF food while sparing normal locomotor and social behaviors. We also investigated the sensitivity and specificity of delta oscillations as a biomarker for food reward anticipation by reviewing the videotaped behavior and determining when bouts of electrical stimulation triggered during RNS® occurred. Out of a total of 179 HF pellet approaches 124 were detected by the RNS® device such that stimulation was triggered (sensitivity=0.693, FIG. 11L). There were also 1241 correct rejections (stimulation withheld when no HF approach occurred) and 685 stimulations triggered when no pellet approach occurred (specificity=0.644, FIG. 11M). Lastly, we found that NAc DBS had no significant on 24-hr chow consumption (FIG. 15B).

Figure 12A:
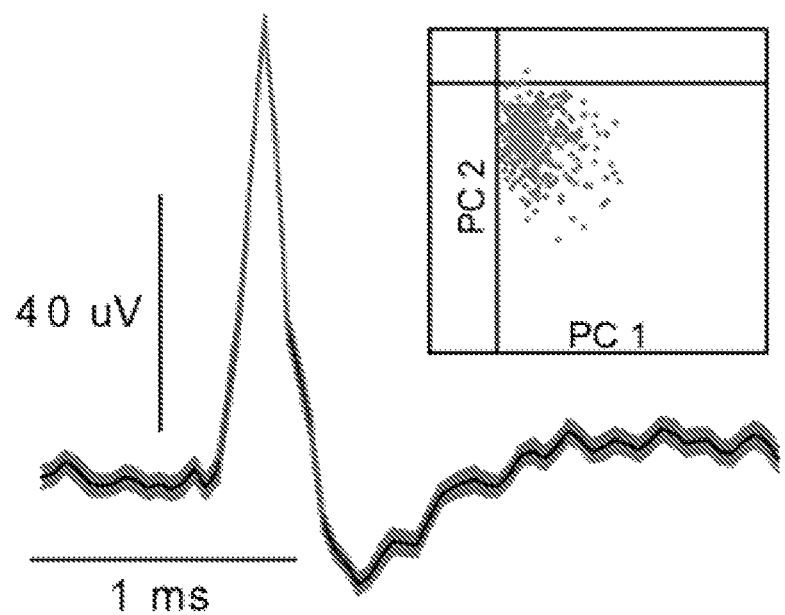
FIGS. 12A-12F: Multi-unit and coherence analyses.
Figure 12B:
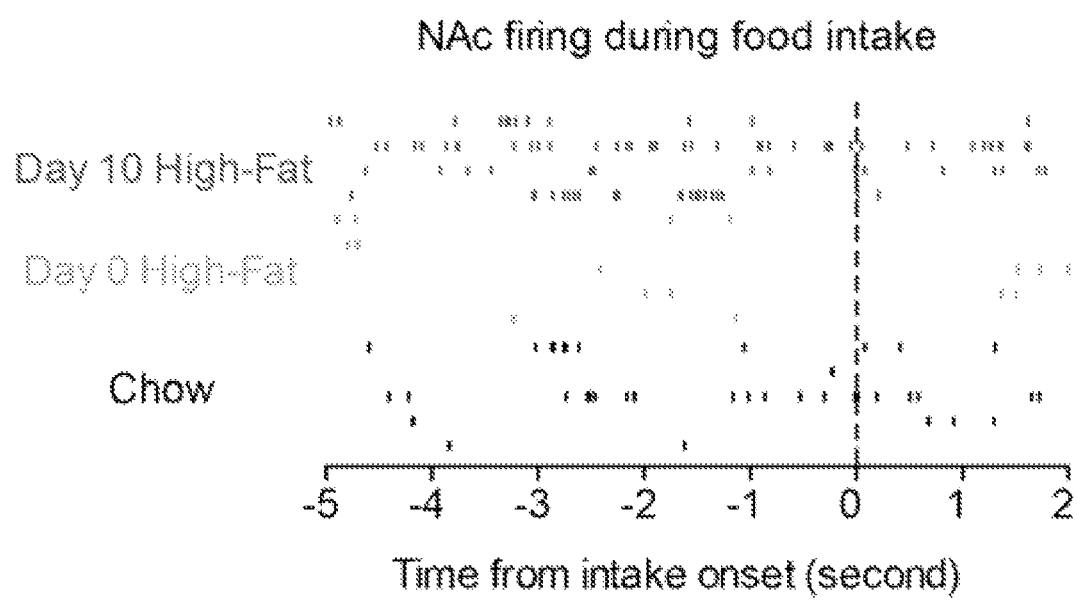
Figure 12C:
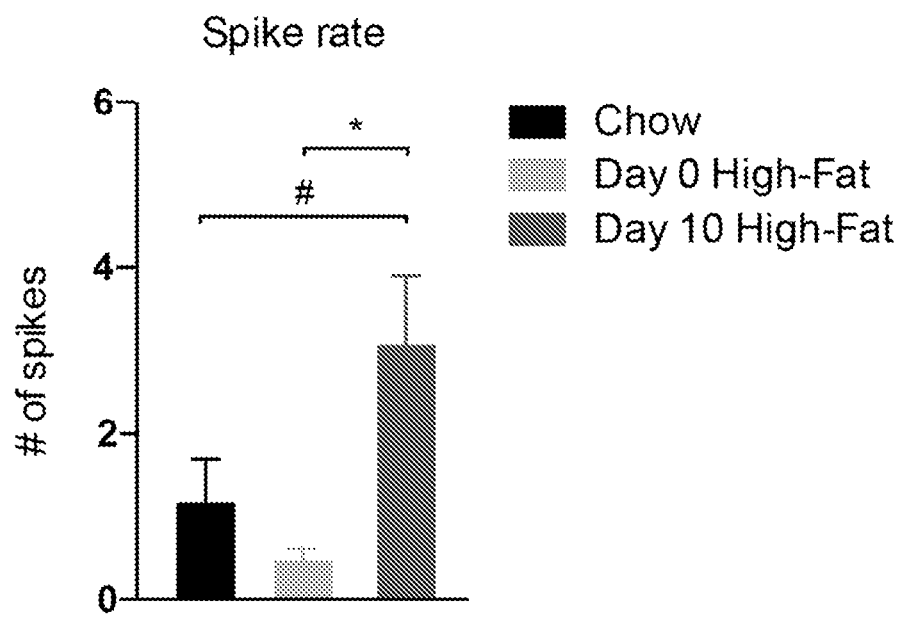

To investigate the source of delta oscillations in the NAc during high-fat consumption in mice, we searched for the occurrence of single unit activity in the LFP recordings. We identified one type of spike shape consistently (FIG. 12A), which appeared significantly more frequently on day 10 during HF consumption when binge eating was prominent ($F(2, 12)=5.221$, $P<0.05$, post hoc: chow vs day 0 HF: n.s., chow vs day 10 HF: $P<0.1$, day 0 HF vs day 10 HF: $P<0.05$, Tukey corrected, FIGS. 12B-12C). The delta spike-field coherence, the strength of coupling between spike times and the phase of LFP at delta frequency range, was significantly higher on day 10 immediately before and during HF consumption ($F(2, 12)=8.102$, $P<0.01$, post hoc: chow vs day 0 HF: n.s., chow vs day 10 HF: $P<0.05$, day 0 HF vs day 10

Figure 12D:
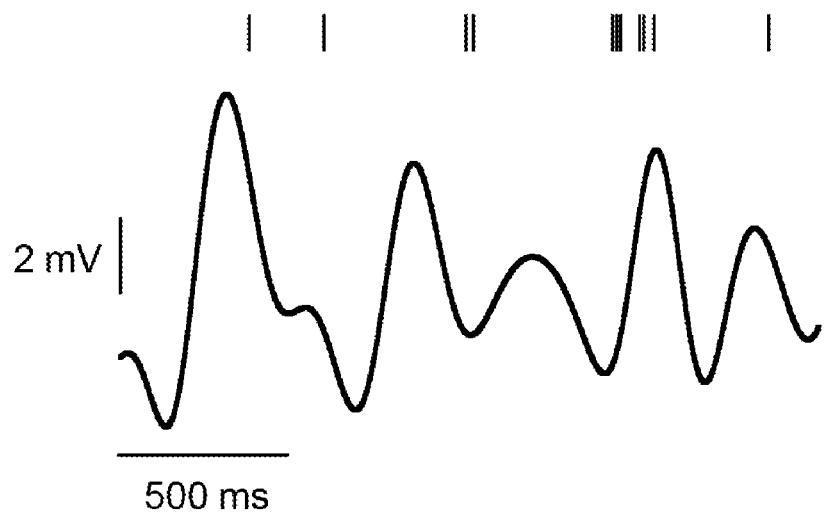
Figure 12E:
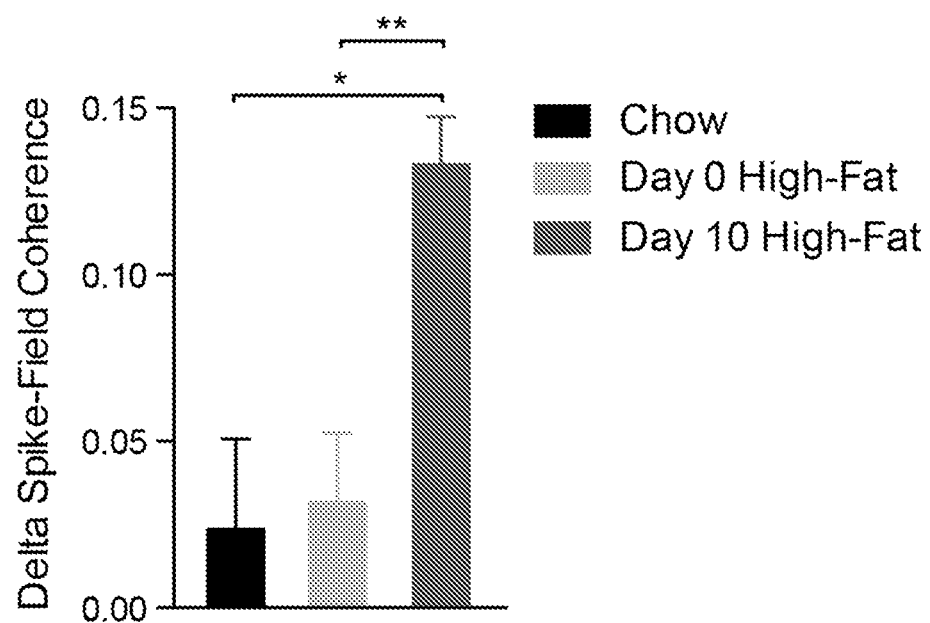
Figure 12F:
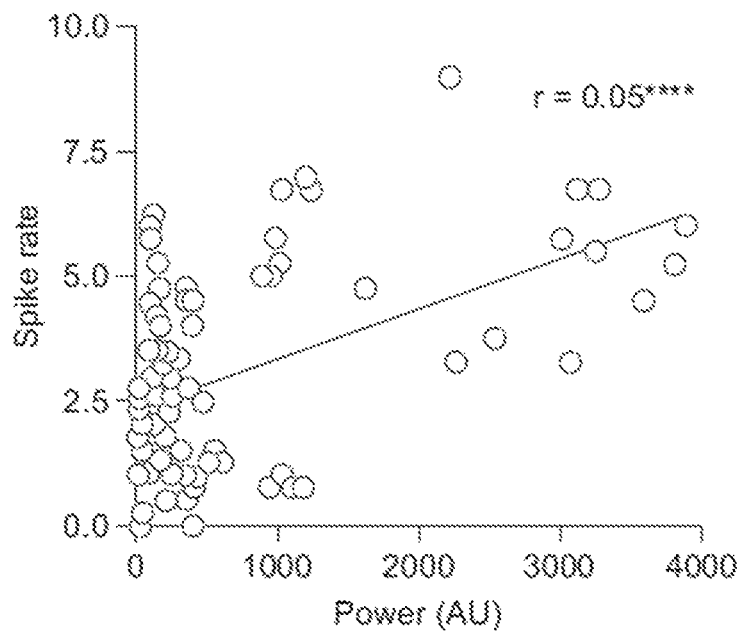
Figure 12F:
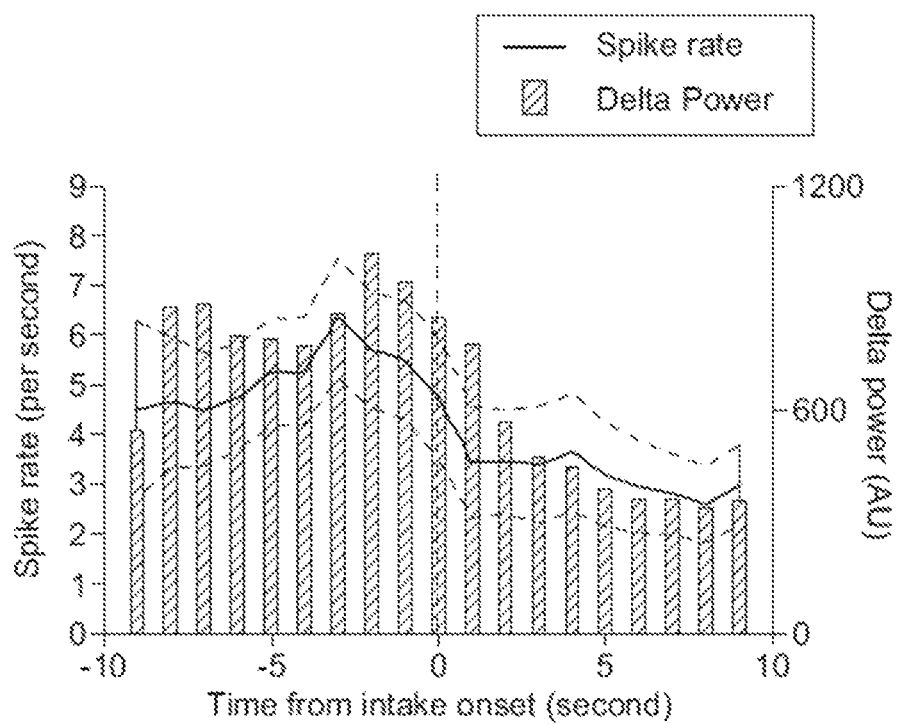
Figure 13A:
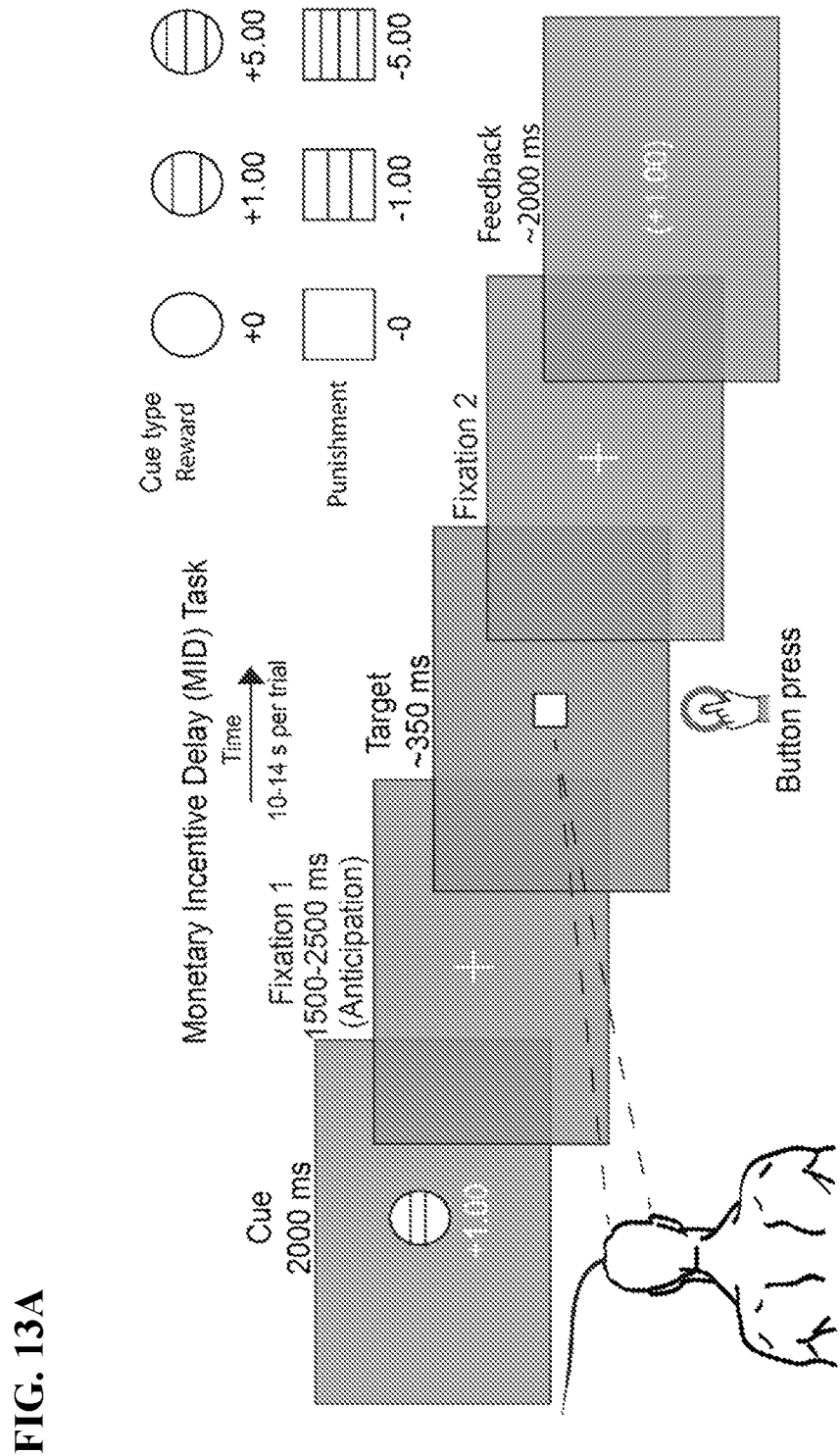

HF: P<0.05, Tukey corrected, FIGS. 12D-12E). Lastly, the spike rate significantly correlated with delta power, on day 10 immediately before and during HF consumption (Pearson r=0.50, P<0.0001, FIG. 12F).

fMRI Activity and Delta Oscillations in Human NAc during Reward Anticipation. To evaluate the translational potential of delta range field potentials providing physiologic, real-time optimization for RNS® in human patients suffering from impulsivity, we recorded intraoperative LFPs from the NAc in a human subject suffering from intractable obsessive-compulsive disorder during a period of reward anticipation analogous to the phase of food reward anticipation examined in mice. Specifically, because in the operating room food rewards could not be provided, we instead elicited anticipation of monetary rewards with a well-established neuroimaging task (i.e., the Monetary Incentive Delay (MID) task). During each trial of the MID task, a subject sees a visual cue indicating that they will gain or avoid losing an indicated monetary incentive (reward or punishment) by subsequently pressing a button in response to a rapidly presented target. This task allows researchers to distinguish neural responses during different stages of reward processing, including reward anticipation and outcomes (FIG. 13A) (10).

Figure 13B:
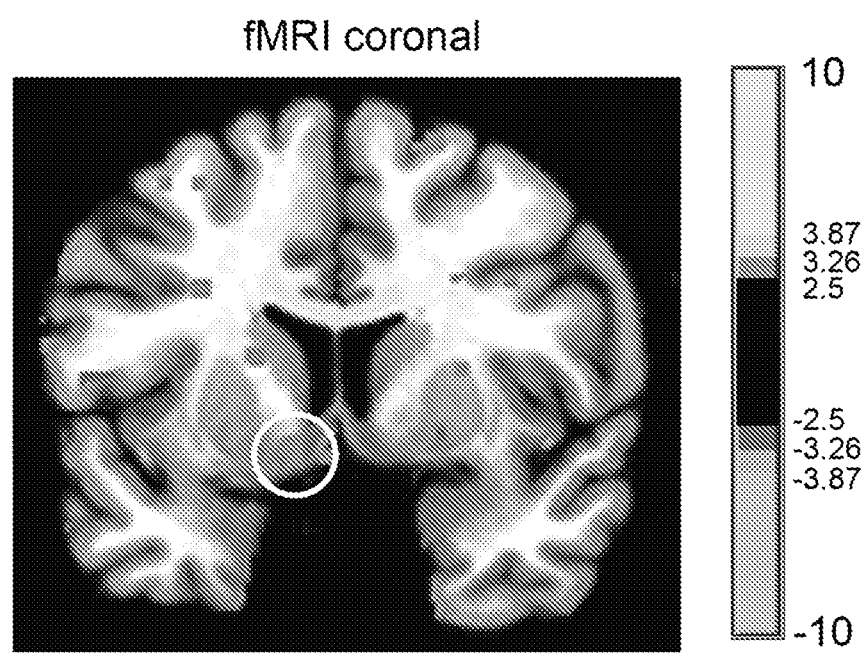
Figure 13C:
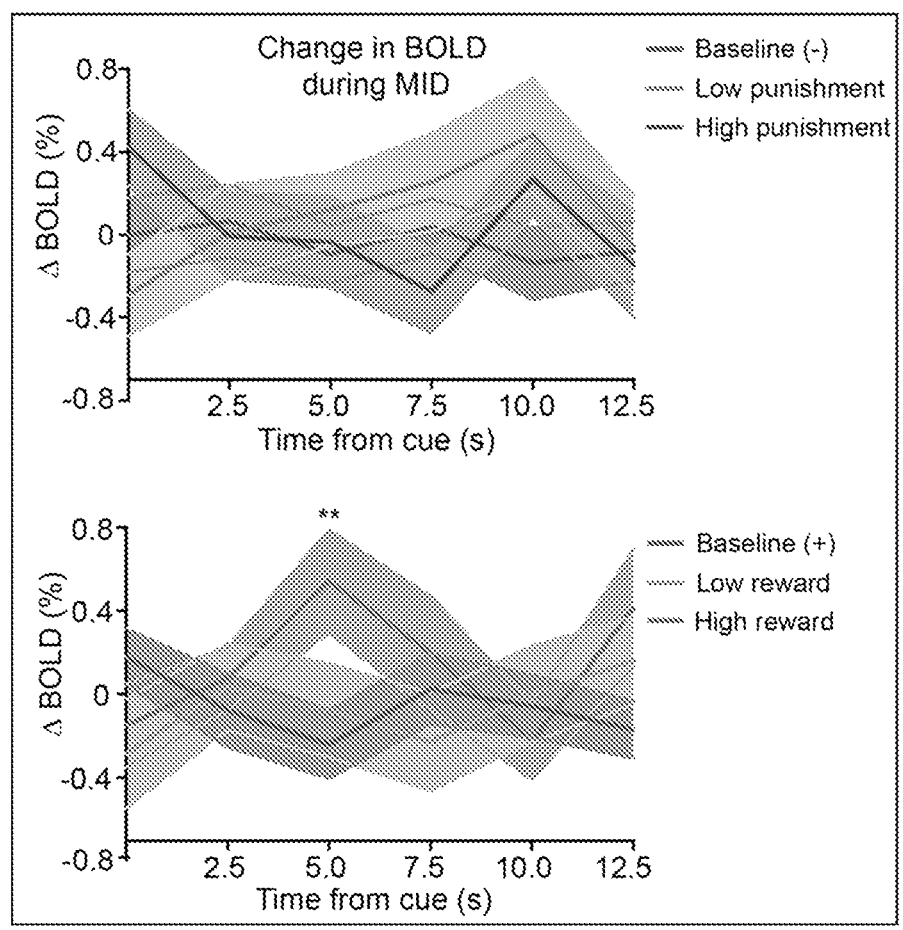
Figure 13D:
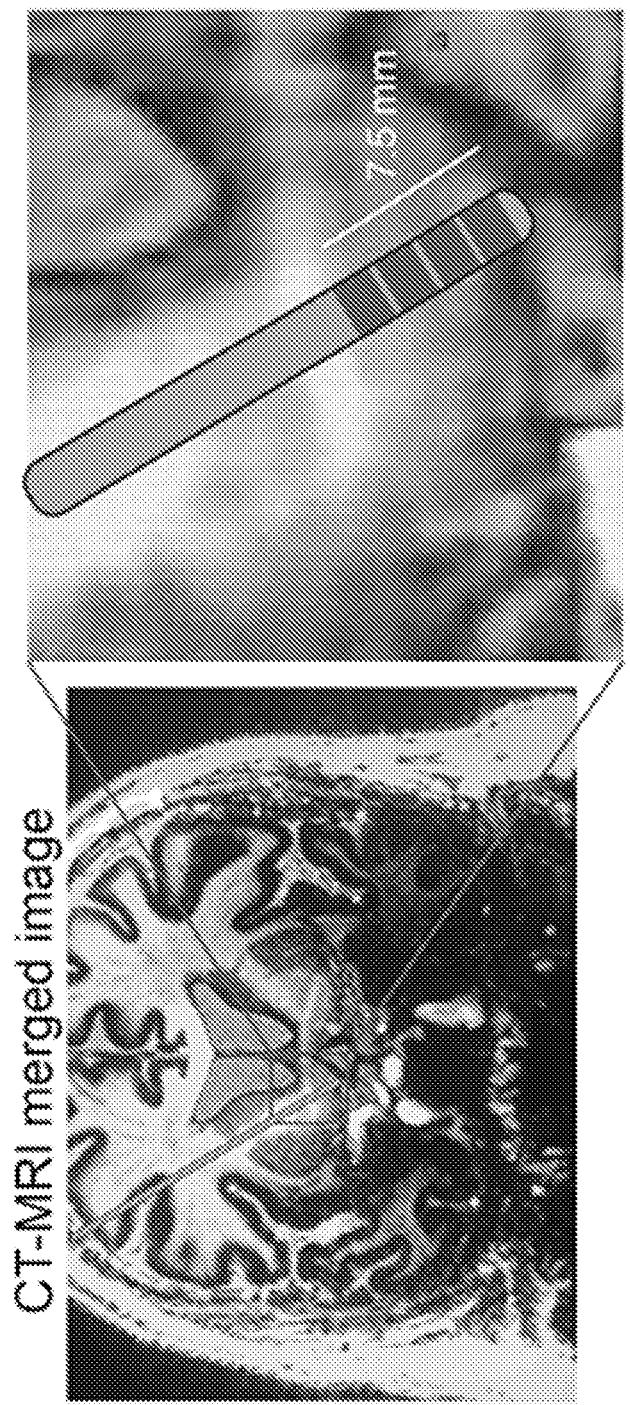
Figure 13E:
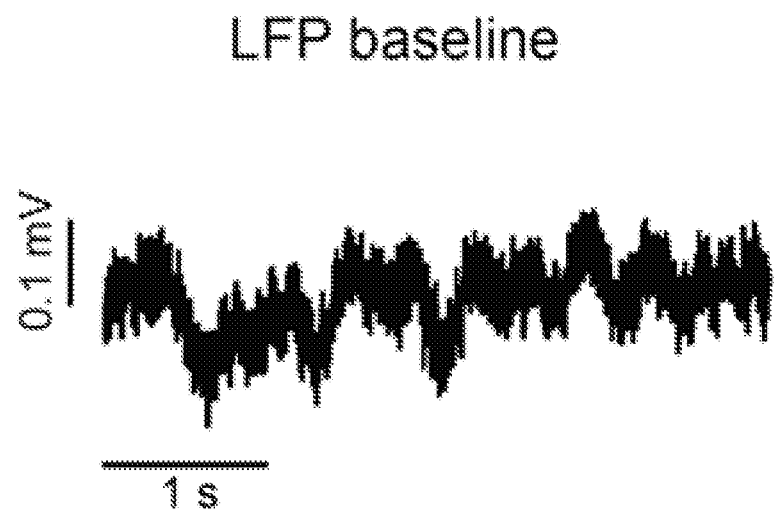
Figure 13F:
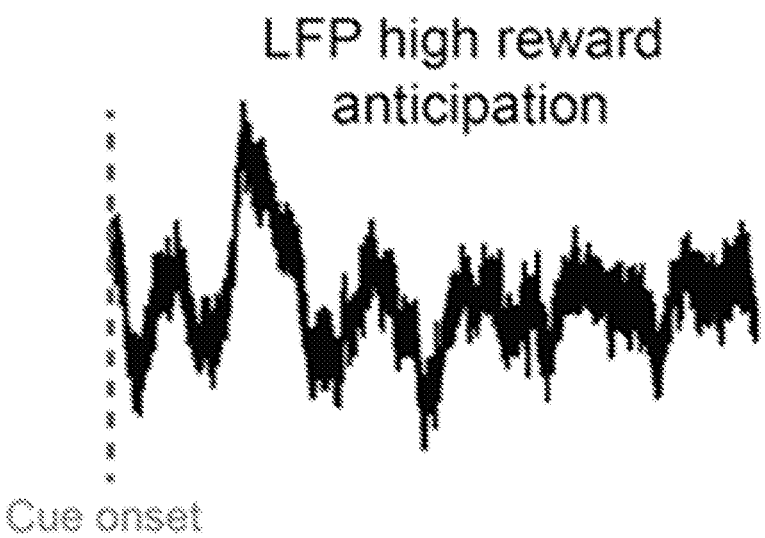
Figure 13G:
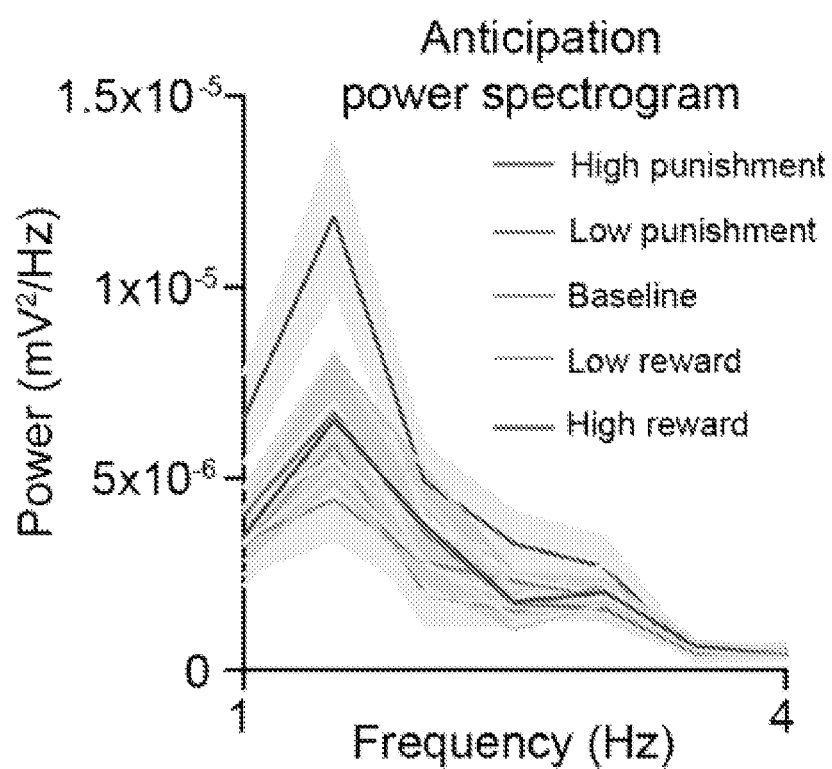
Figure 13H:
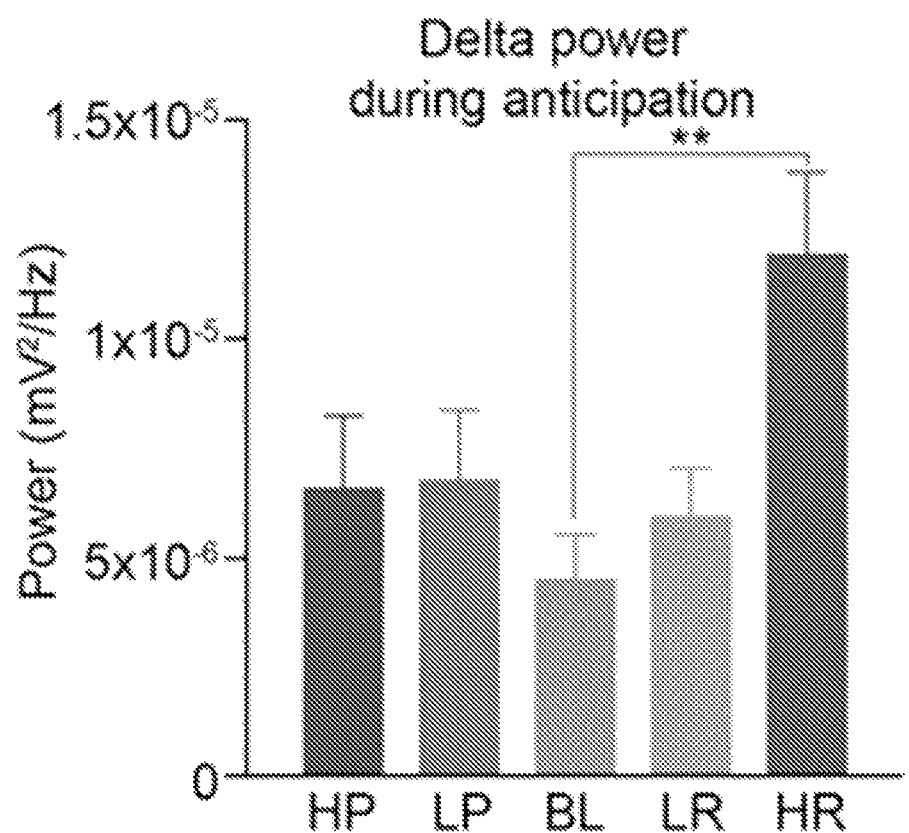
Figure 13I:
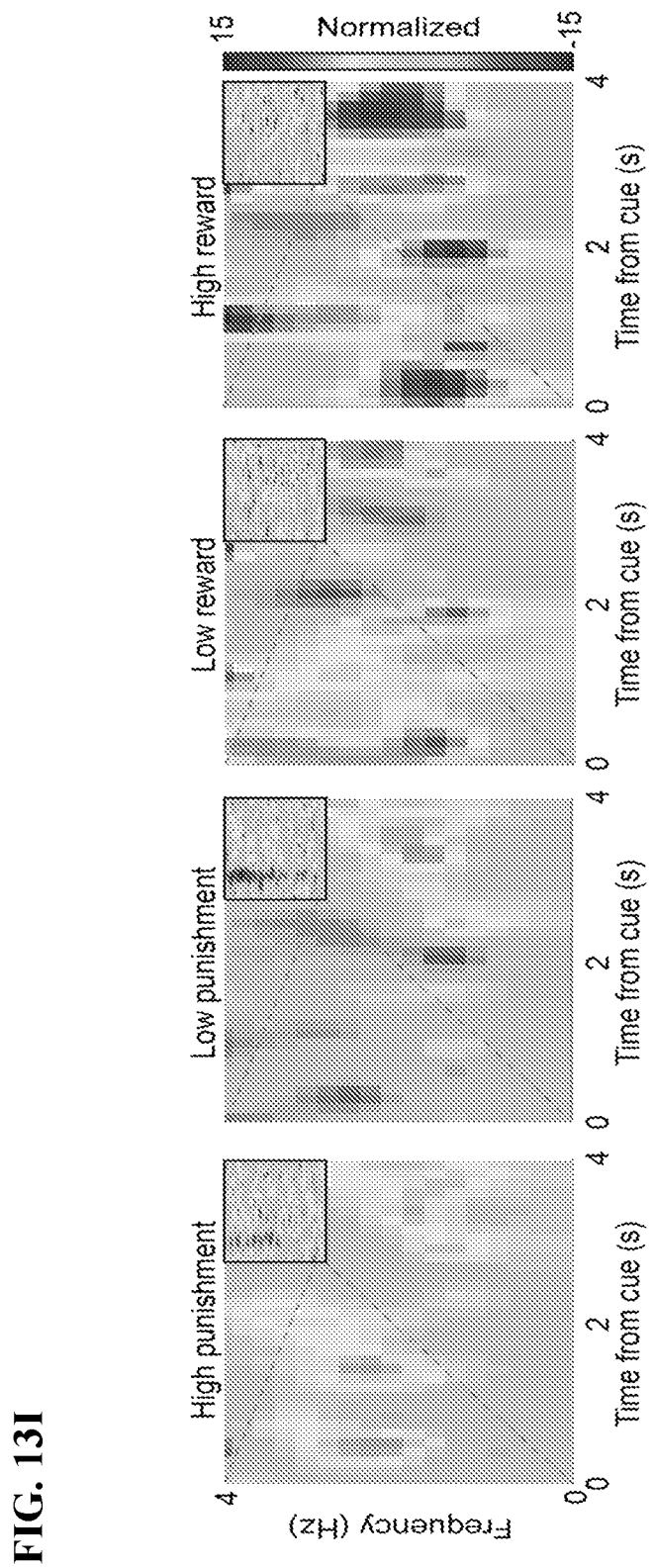
Figure 16A:
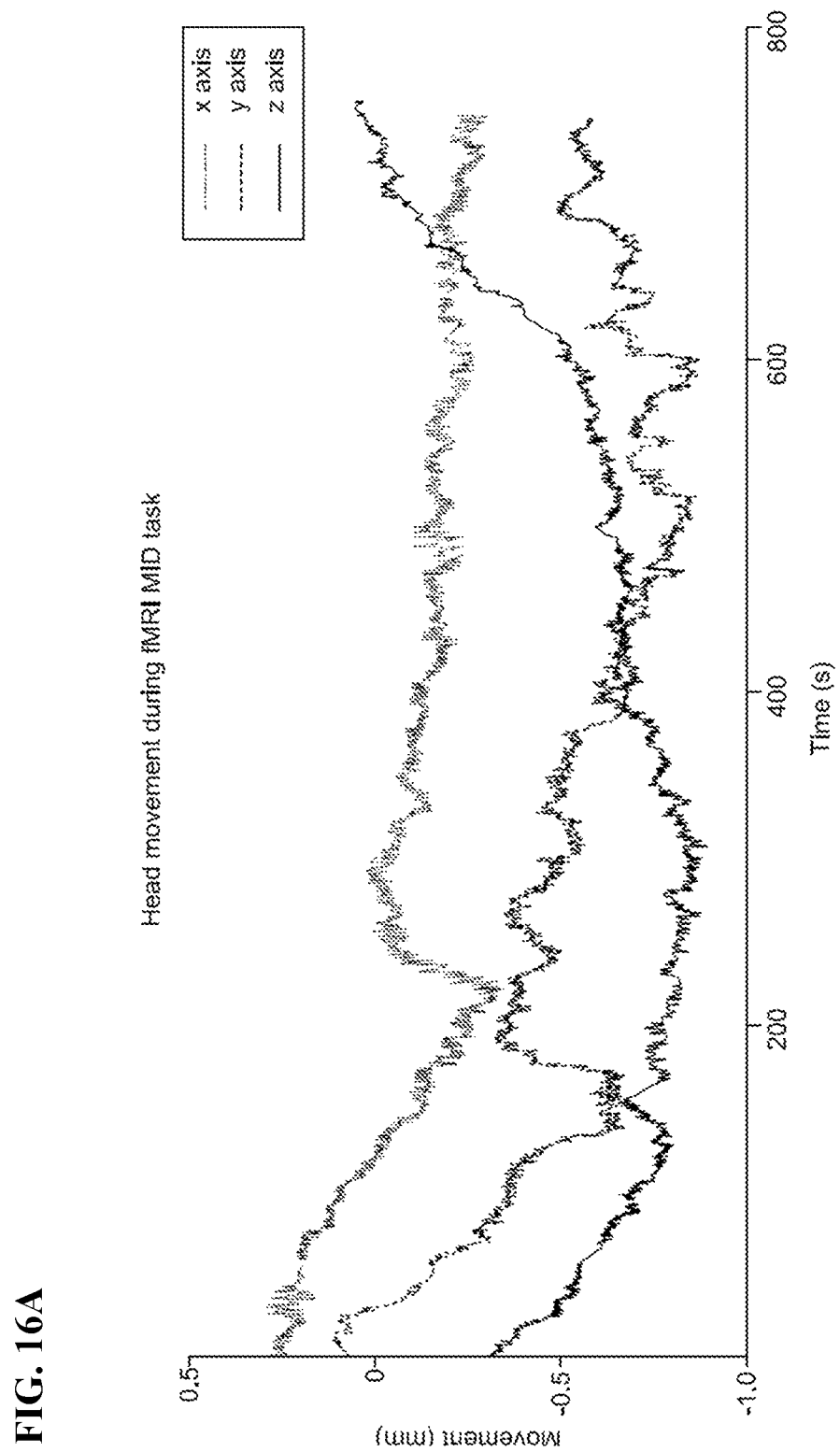
FIGS. 16A-16B: Related to FIGS. 13A-13I.
Figure 16B:
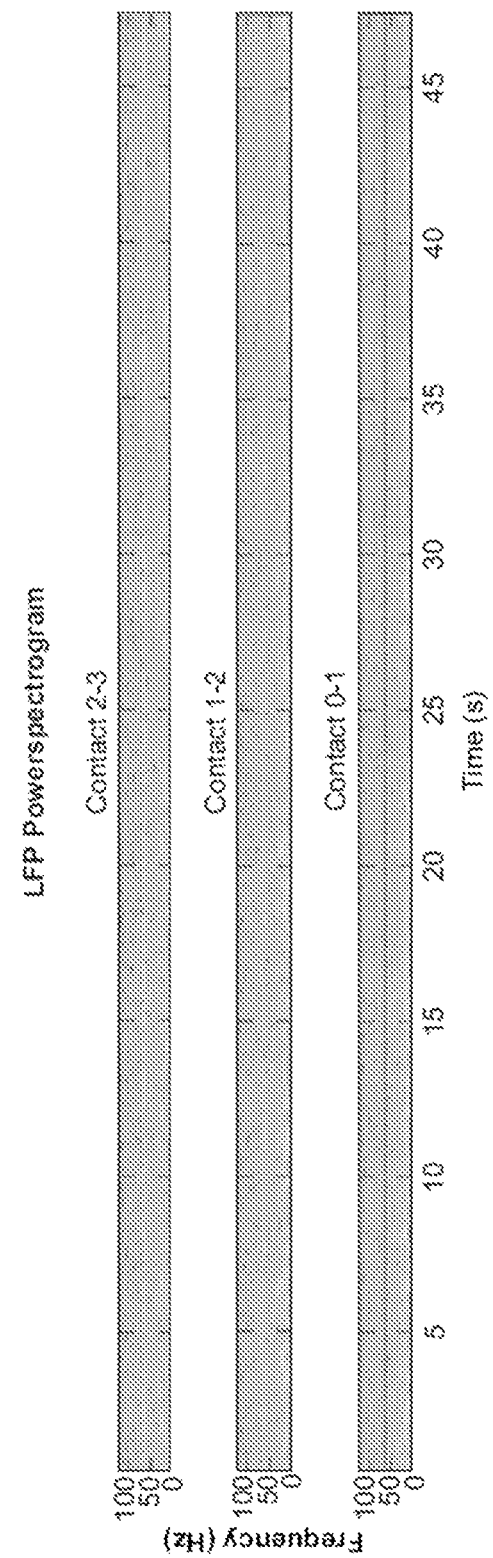
Figure 16B:
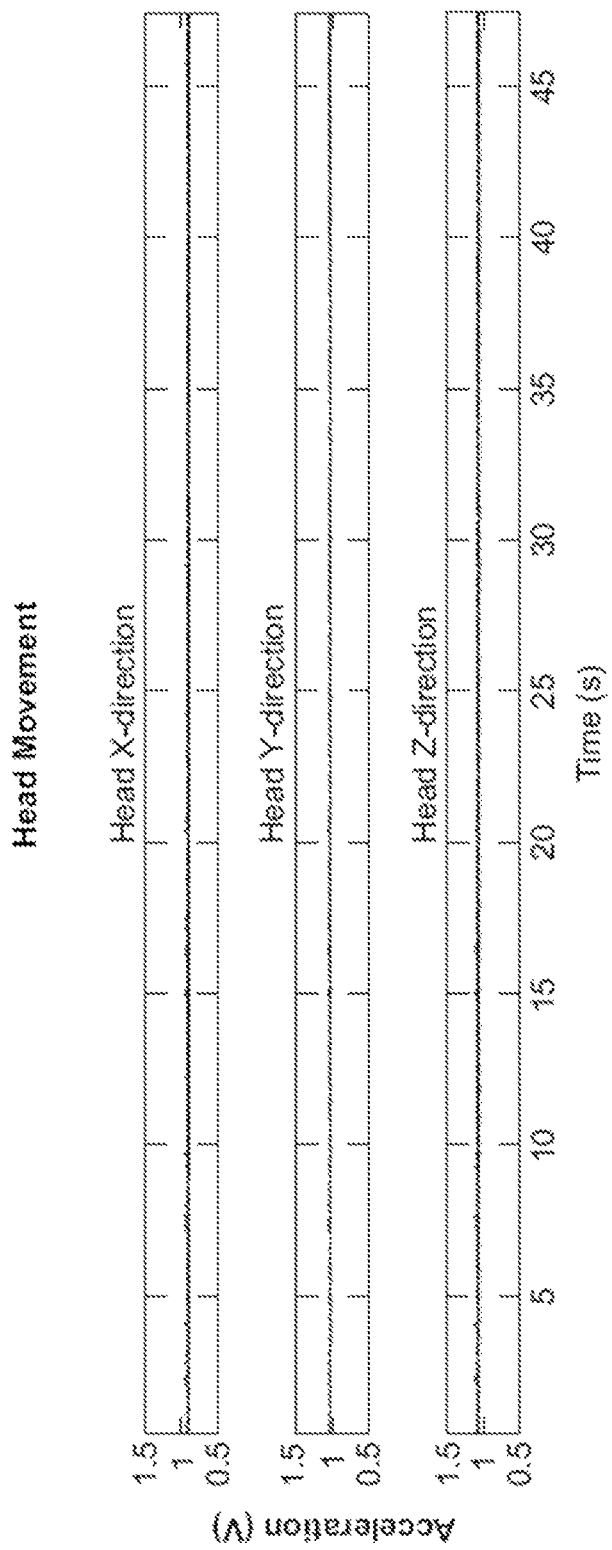
Figure 16B:
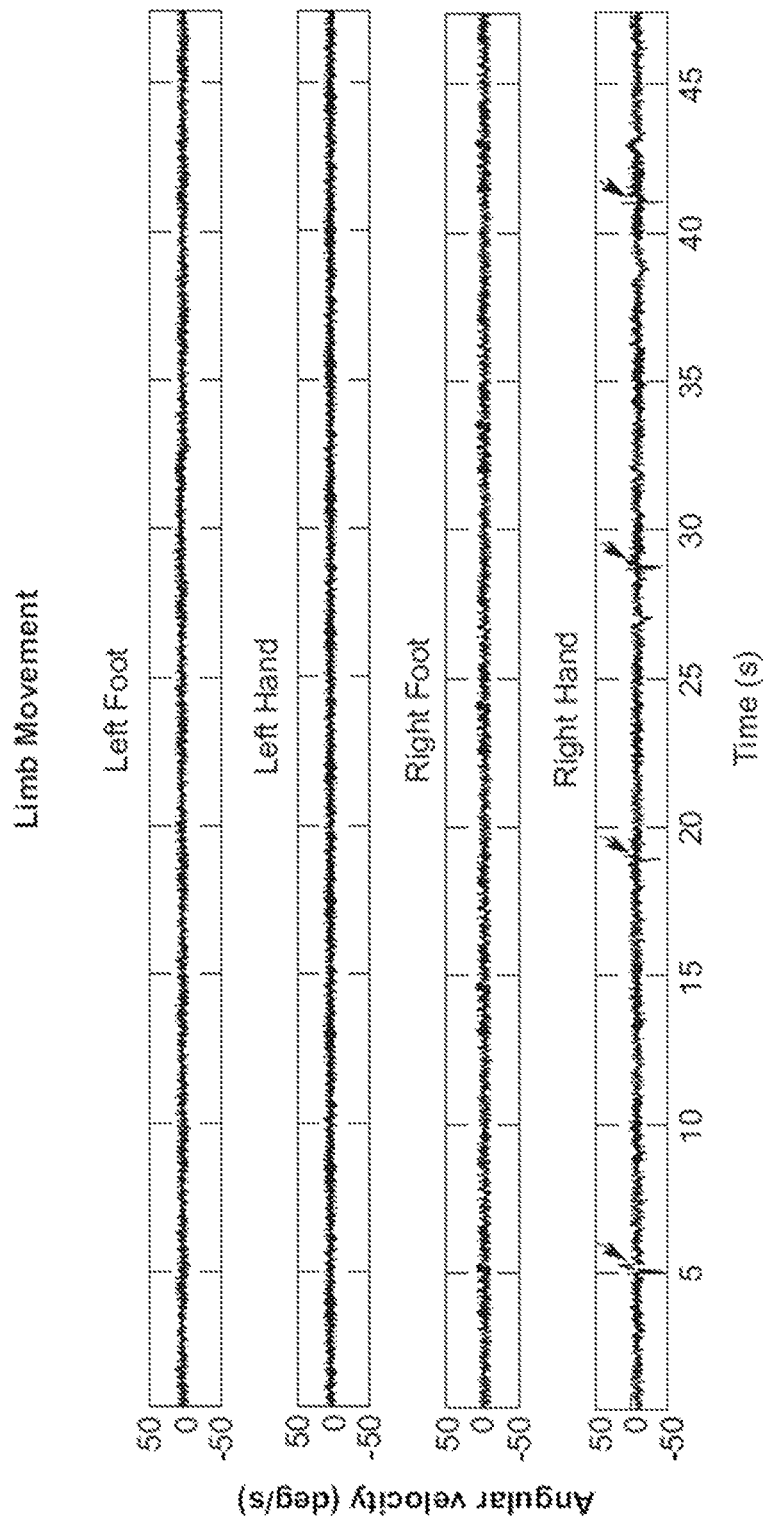
Figure 17:
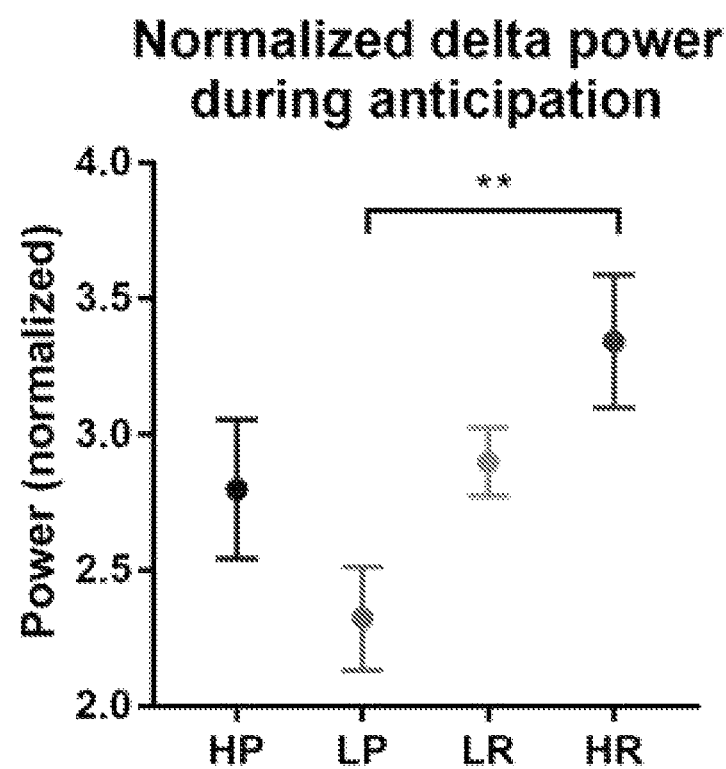
FIG. 17: Related to FIGS. 13A-13I. Normalized delta power in the human nucleus accumbens during anticipation of high monetary reward was significantly higher than during anticipation of low punishment in the monetary incentive delay task (ANOVA: F=3.964, p=0.0138, post-hoc pairwise: high reward vs low punishment: p=0.0070).
Figure 18A:
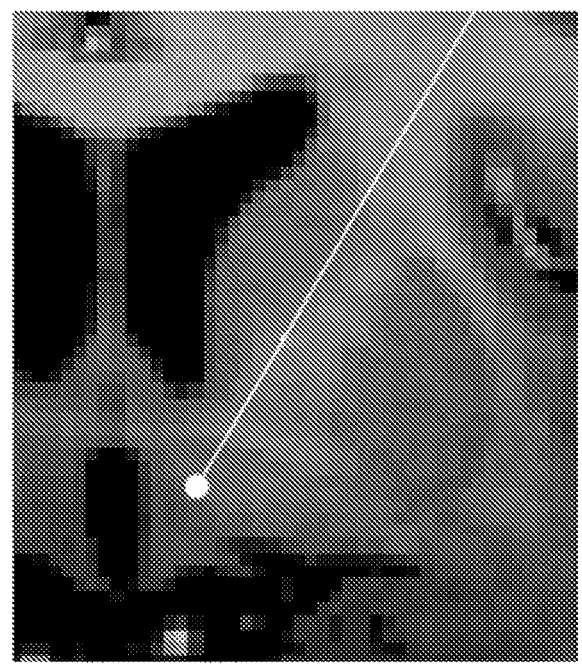
FIGS. 18A-18G: Related to FIGS. 13A-13I. Spike isolation for single unit in the ventral nucleus accumbens.
Figure 18B:
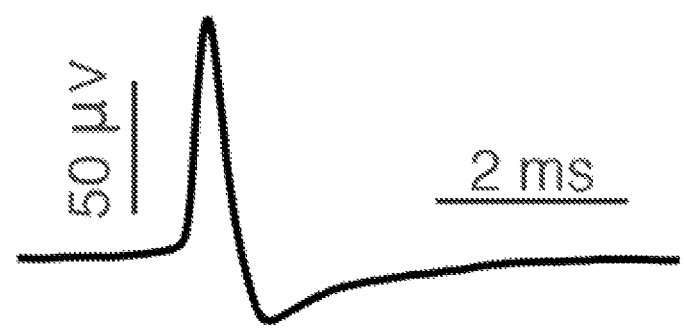
Figure 18C:
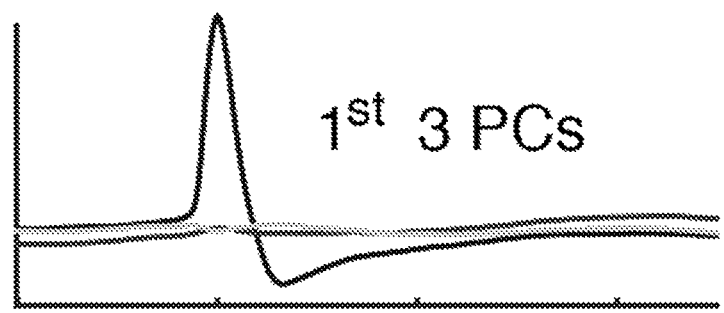
Figure 18D:
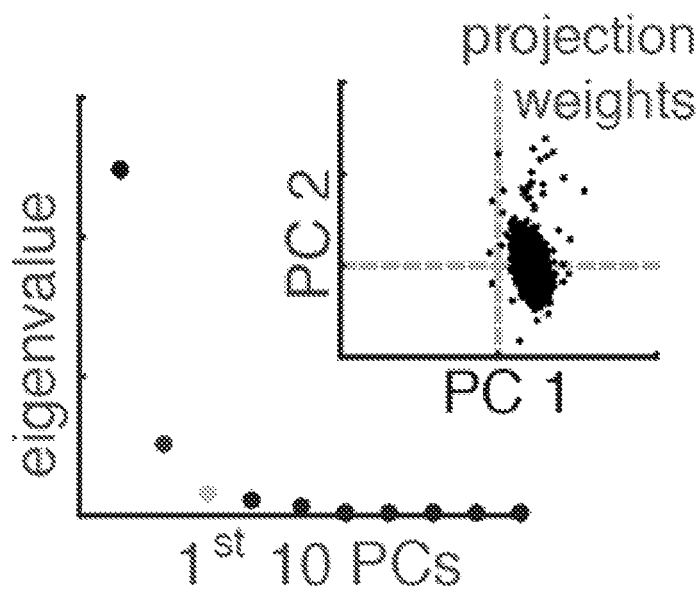
Figure 18E:
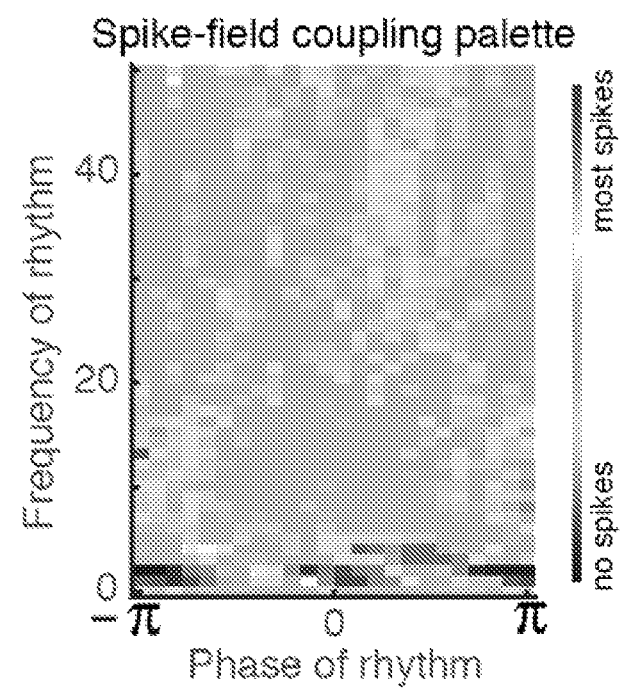
Figure 18F:
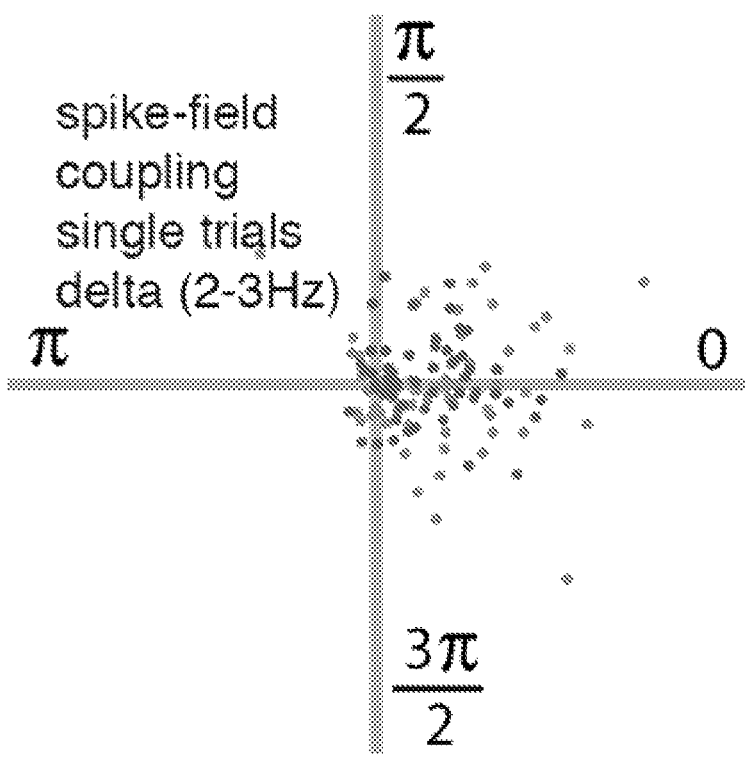
Figure 18G:
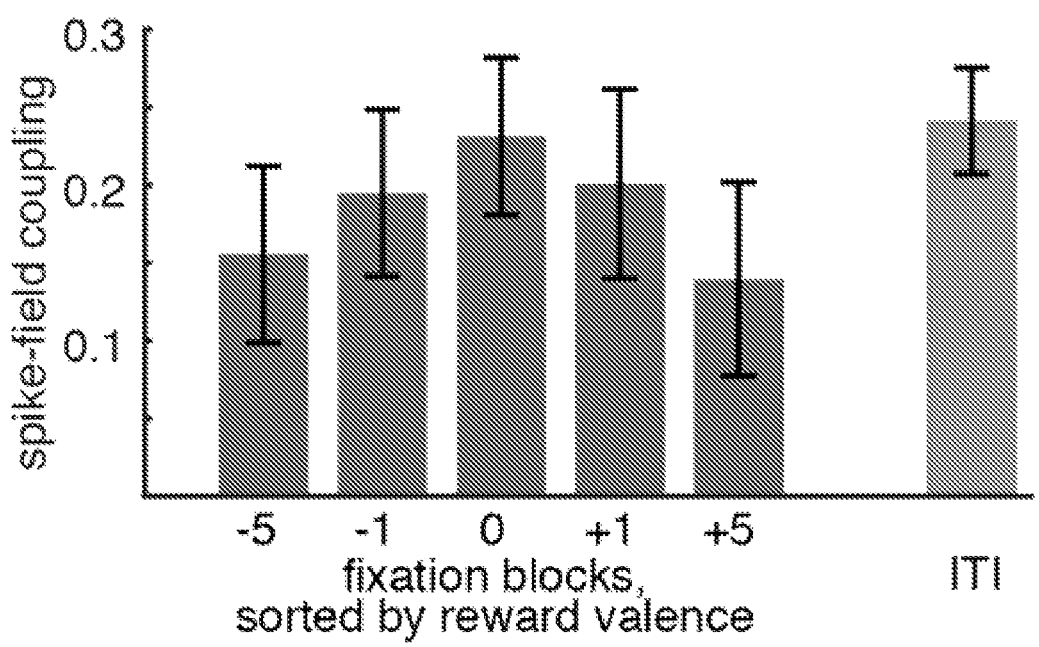

Prior to surgery during a diagnostic magnetic resonance imaging (MRI) scan, functional MRI revealed a significant increase in blood oxygen level dependent (BOLD) signal in the NAc during anticipation of high monetary reward (high reward:baseline, T(17)=3.23, P<0.01, uncorrected; low reward:baseline, high punishment:baseline, low punishment:baseline, n.s. FIGS. 13B-13C; summary of head movement shown in FIG. 16A, demonstrating <1 mm of head movement). This finding replicated previous reports using normal subjects and corroborates a well-established involvement of the human NAc during reward anticipation (18). LFPs were recorded via an implanted quadripolar electrode (3389, Medtronic, Minneapolis, MN, USA) in the NAc, the location of which was defined by merging a postoperative computed tomography scan of the head to a preoperative 7 T MRI scan using gray matter nulled sequences that indicate precise white matter-grey matter boundaries (FIG. 13D). Power spectral density analysis of NAc LFPs during no reward and high reward anticipation (FIGS. 13E-13H) revealed an increase in delta power during the anticipation period for high reward compared to no reward in the most ventral channel (FIG. 13H: F(4, 67)=3.514, P<0.05, post-hoc: high reward vs baseline: P<0.01, Tukey's correction applied). Head and limb movement during intraoperative LFP recordings (FIG. 16B) indicated that there was very little detectable movement. Comparison of delta power measurements during anticipation of high punishments, low punishments, and low rewards normalized to baseline showed significant increase during anticipation of high reward vs low punishment (FIG. 13I and FIG. 17). We also investigated the correlation between NAc LFP and unit activity during MID task, and found selective phase-locking of spikes to the peak (phase 0) of the delta (2-3 Hz) oscillations (FIGS. 18A-18G).

Discussion We have demonstrated that anticipation of large rewards increases delta oscillatory power in the NAc in mice, and preliminary findings from a single human subject support the translatability of this potential biomarker for RNS®. In sated mice exhibiting binge-eating behavior, strong delta oscillations are detected 2 seconds prior to consuming food reward, but not prior to intake of house chow. This increase in delta power is not observed prior to or during general locomotor behavior or social interaction, and is strongly positively correlated with unit activity in the NAc. Using a threshold in delta band power as a biomarker to trigger delivery of a brief train of high-frequency electrical stimulation pulses to the NAc resulted in significant attenuation of HF intake. The effectiveness of this RNS® was reproducible and behaviorally specific. Namely, utilizing power in the delta band as a trigger for RNS® did not interfere with social interaction or locomotor behaviors. Moreover, the number of stimulation bouts delivered during RNS® was significantly lower than DBS to achieve the same reduction in HF intake. Stimulation of the NAc was not reinforcing or aversive as assayed by a real-time place preference protocol, suggesting that stimulation-induced blockade of HF intake was not substituting for the anticipated food reward or inducing an aversion. Post-hoc review of stimulations triggered during RNS® revealed that our biomarker settings correctly anticipated about two thirds of HF binge onsets, while approximately one quarter of the triggered stimulations were not associated with subsequent binge onset.

To examine the translational potential of our findings, we analyzed NAc LFPs during anticipation of monetary rewards in a human, which like HF in mice, demonstrably elicits vigorous approach (10). The MID task was used here so that we could examine the human NAc LFPs during a similar brief period of reward anticipation that was studied in mice. Anticipation of large financial incentives are known to reliably increase NAc BOLD signal activity in healthy individuals (18). Because BOLD activity has been reported to correlate with changes in LFPs (19, 20), we predicted that anticipation of large rewards would induce measurable changes in LFPs in the NAc. Consistent with what is commonly observed in healthy individuals, event-related functional MRI in a human subject suffering from severe OCD revealed increased NAc BOLD signal during anticipation of large rewards. Most importantly, NAc LFPs recorded from this subject exhibited an increase in power in the delta band during anticipation of high monetary rewards. These electrophysiological changes echoed those seen in mice anticipating HF reward and importantly was detected by a clinically-approved benchtop system. Moreover, the MID task is a good probe of reward anticipation in that it increases positive arousal associated with monetary reward anticipation as has been demonstrated in food reward studies in mice (21, 22). This illustration of spike-field coherence in humans illustrates that oscillations in the delta-range, at the spatial scale of the local field potential measured by the high-impedance microelectrode (at ~200 μm (23), influence the timing of action potentials in the ventral NAc. Although the DBS scale field potential recordings of power change during the reward task (at ~2 mm) are not related in any simple way, the finding of spike-field coherence does establish the saliency of the delta range power as a marker of local computation. Together, these findings demonstrate that NAc LFPs carry information relevant to reward anticipation, and have the potential to be used as a neural electrographic biomarker to guide RNS® treatment for neuropsychiatric disorders exhibiting impulsivity.

RNS® remains a highly novel therapeutic approach with which clinicians have limited experience. For intractable temporal lobe epilepsy, RNS® has proven efficacious in reducing seizure frequency and severity with outcomes that are not only durable but also improve over time (24). Several lines of evidence also suggest that responsive or closed-loop DBS using power in the beta band detected in the subthalamic nucleus across species may be superior to traditional continuous DBS for Parkinson's disease treatment (25-28).

Moreover, other proposed mechanisms of closed-loop neurostimulation strategies have exhibited promise for neuropsychiatric disease, demonstrating the broad potential for this line of research (29).

Our findings provide preliminary evidence that RNS® has potential for treating intractable behavioral disorders that have not previously been considered optimal candidates for neurosurgical approaches, including addiction, obsessive-compulsive disorder, eating disorders, and even obesity. We used chow as the primary food control in our study, and social interaction as another behavior control as this is considered an assay of reward processing in mice. Other conditions, such as drugs and mating, are of tremendous research interest to better refine biomarkers of different rewards. Nevertheless, the fact that mouse and human NAc LFPs exhibit similar changes during reward anticipation suggests that mechanistically driven research in rodents can inform what is eventually done in human subjects. Furthermore, we have demonstrated that the candidate biomarker can be detected using an off-the-shelf, commercially available RNS® device, suggesting that rapid progress can be made toward a neurostimulation treatment for patients suffering from intractable, life-threatening impulse-control disorders.

Materials and Methods

Animal Studies

Animals. All mice were male C57BL/6J (8 weeks) purchased from The Jackson Laboratory. Mice were individually housed on a 12 h light/dark schedule and were sated with food and water ad libitum. House chow contained 18.6% protein, 44.2% carbohydrates, and 6.2% fat by calories and 3.10 kcal/g (Teklad Diet). Given a previously validated model of binge-eating behavior using limited-exposure to a very high fat diet protocol, a diet, which contained 20% protein, 20% carbohydrates, and 60% fat by calories and 5.24 kcal/g (Research Diets), was used in this study to model binge eating (Halpern et al., 2013).

Surgery and Histology

After 1 week of habituation to our facility, mice were anesthetized with ketamine/xylazine and mounted in a stereotaxic frame (Kopf Instruments). Custom multielectrode arrays (70/30% Pt/Ir, 125 um, Microprobes, Gaithersburg, MD) were implanted unilaterally into the left NAc, according to the following coordinates relative to bregma: 1.34 mm anterior, 0.60 mm lateral, and 4.25 mm deep to brain surface (1). Skull screws overlying the frontal cortex served as reference. At the end of our behavioral protocol, mice were anesthetized with pentobarbital and perfused trans-cardially with 4% paraformaldehyde fixative. Electrodes then were removed. Whole brains were extracted from the crania, postfixed for 24 h, and submerged in phosphate-buffered saline for 48 h. Brains were cut by microtome into 60 um coronal sections, and examined under a confocal microscope to verify electrode placement.

Behavioral Assays

Binge-eating behavior. Binge eating, defined here as consumption of 25% of a mouse's daily caloric intake within a 1 h period, was observed in all mice using a limited-access protocol. This protocol is known to induce binge-like behavior in non-calorically restricted mice because of the brevity and intermittent nature of the exposure (Halpern et al., 2013). A single, preweighed high-fat (HF) pellet was provided to the mice in their home cage daily for 1 h. Intake of the HF diet within that 1 h period was measured, as was 24 h consumption of house chow. Stimulation protocols were only initiated following 3 days of stable binge eating (<10% variation across 3 consecutive days). Consumption of chow and HF were recorded with timestamp via a CCD camera interfaced with Ethovision® software (Noldus, Wageningen, the Netherlands).

Juvenile interaction test. Novel male C57BL/6J (4 weeks) mice purchased from The Jackson Laboratory were used as the juvenile mice. Open-field arenas and the video-tracking apparatus and software (Ethovision®, Noldus, Wageningen, the Netherlands) were set up to monitor behavior (2). Experimental mice were habituated to the testing suite for ~1 h before testing. Each juvenile interaction test is composed of two 150-s phases either with or without NAc stimulation (see Electrical stimulation section below) separated by a duration of 30 s. Immediately after terminating phase 1, we removed the test mouse from the arena and returned it to its home cage until phase 2. The test mouse encountered a novel juvenile mouse during each phase.

Real-time place preference test. Mice were placed in a custom-made 3-chamber behavioral arena (75×25×25 cm black Plexiglas) for 30 min (3). One side chamber (30×25 cm) was assigned as the continuous stimulation side and the other as non-stimulation (30×25 cm). At the start of the session, mice were placed in the center chamber (15×25 cm). Every time the mice crossed to the stimulation chamber, electrical stimulation was delivered to the NAc until the mice crossed back into the center chamber. Percentage of time spent on the stimulation-paired and movement were recorded via a CCD camera interfaced with Ethovision® software (Noldus).

Behavioral and neural signal recording and analyses. During all of the behavioral assays, mice were tethered to a neural recording device (Alphalab SnR, Alpha Omega, Nazareth, Israel), and neural signals were recorded at 22k Hz continuously, together with synchronized behavioral data (Ethovision®, Noldus, Wageningen, the Netherlands). To extract information in the local field potential range, signals were downsampled offline to 1375 Hz, and segments corresponding to chow and HF intake (during exposure to HF) and juvenile interaction (in juvenile interaction test) were extracted (2-s epoch prior to the onset of the task). The short-time Fourier transform was used to approximate the power spectrum (Welch's method, window of 1 s, 50% overlap) and averaged across individual mice (4). Time-frequency domain analysis was performed using a short-time Fourier transform of a 1 s sliding window and 90% overlap (averaged across individual mice). For multi-unit analysis, raw signals were analyzed using the Wave_Clus toolbox (5). Signal processing was performed using the MatLab software package and custom scripts. Behavioral analyses were performed manually (examiner blinded) for identification of the onsets of chow and HF consumptions and juvenile interaction, and using EthoVision® (Noldus, Wageningen, the Netherlands) for place preference test.

Electrical stimulation. Electrical stimulation (0.1 mA, 130 Hz, bipolar, biphasic, 90 μsec) was used throughout different behavioral assays. Electrical stimulation was applied continuously to mimic DBS conditions. In the manual setting during HF exposure, electrical stimulation was turned on for 10 s by an experimenter (HW) remotely as soon as HF consumption was observed, then turned off until the next binge-like behavior was observed. In the RNS® setting, stimulation was triggered by a programmable biomarker detector (Neurostimulator, Model RNS®-300, Neuropace, Mountain View, CA, USA), in which the biomarker detection could be set up by predefining window size, minimum width, count criterion, minimum amplitude, bandpass hysteresis, and bandpass threshold. A typical biomarker detection setup for the delta oscillations was: 1200 ms window size, count criterion=4, bandpass hysteresis=255, bandpass threshold=3, and 20% increase delta power. In randomly-applied stimulation setting during HF exposure, electrical stimulation was administered according to a predefined randomized protocol.

Statistics. Student's t test was used to determine statistical differences for chow and HF intake, spectral power during chow and HF intake, and real-time place preference. One-way ANOVA was used to determine statistical differences for power consumption, juvenile interaction, locomotor, and spectral power during MID task. Repeated measures ANOVA was used to determine statistical differences for reduction in HF intake induced by different stimulation protocols. Bonferroni post hoc analysis was applied, when necessary, to correct for multiple comparisons. Statistical significance was * $p<0.05$,  $p<0.01$, * $p<0.001$. All data values are presented as means±SEM. We used SPSS 21 (IBM, Armonk, NY, USA) for all statistical analyses.

Human Studies

Participant data. The human subject was a 64-year-old male undergoing implantation of DBS electrodes in the NAc for treatment-resistant obsessive-compulsive disorder. The patient participated voluntarily in this two-part study after informed consent was obtained during preoperative consultation for the surgery, and was free to withdraw from the study at any time, including during imaging and surgery without consequence to clinical care. As per the protocol, the patient's medications were continued before surgery. This investigation was carried out in accordance with a Stanford University IRB approved protocol (IRB-33146). Preoperatively, this patient underwent a routine stereotactic magnetic resonance imaging (MRI) treatment planning protocol complemented by an ultra-high field MRI (7 T) scan for visualizing precise NAc borders, and functional MRI (fMRI) (3 T) scanning during the Monetary Incentive Delay task.

Monetary incentive delay task. Before entering the fMRI scanner, this participant completed a practice version of a previously validated fMRI paradigm that elicits anticipation of monetary reward called the monetary incentive delay (MID) task. This practice task both minimized later learning effects, and produced an estimate of each individual's reaction time for standardizing task difficulty in the scanner. The participant was also shown the money that he could earn by performing the task successfully, and correctly believed that he would receive money at the end of the study period as a function of performance. Once in the scanner, anatomical and functional scans were collected, and the subject participated in one 42-minute session in which the MID task occurred between a preliminary 144 TRs (2.5 s) of rest and a final 144 TRs of rest. The MID task consisted of 96 trials, each lasting 7.5 s (3×2.5 s TRs) presented in a pseudorandom order organized into two separate blocks: first a 50%+/−$0, 50%+/−1 block of 48 trials, then a 50%+/−$0, 50%+/−$5 block trials. Trial types within blocks were presented in pseudorandom order. Each trial began with 2 s of cue presentation: either a circle or square, signifying gain or loss, respectively, with a line positioned within the shape horizontally to correspond to the value of the gain or loss. (i.e. +/−0 trials show a reward in the lower part of the circle/square, and +/−1 showing a line in the middle of the shape, and +/−5 trials showing a line in the upper part of the shape.). Within each trial, each cue period was followed by 1.5-2.5 s of anticipation in which the subject viewed centrally placed fixation cross (+), and a ~0.4 s response period in the subject had to press a button after the appearance of a white target square within a variably short period (~350 ms, calibrated throughout the task to each subject's performance) in order to gain (reward) or avoid losing money (punishment). The subject then received outcome information (2 s) informing him if whether had gained or lost money and the cumulative total. fMRI volume acquisitions were time-locked to the offset of each cue, and so synchronized to the onset of anticipatory delay periods.

Neuroimaging

Functional MRI (3 T). Functional neuroimaging data were analyzed with Analysis of Functional NeuroImages software (Cox, 1996). Data were preprocessed by correcting for non-simultaneous slice acquisition using sinc interpolation, and for three-dimensional motion using sinc interpolation. Any volumes corresponding to acquisitions in which a subject moved >0.25 mm as well as volumes immediately preceding them were excluded from the analysis. Data were spatially smoothed (FWHM=4 mm) and high-pass filtered within blocks to omit frequencies longer than 90 s (6). Voxel-wise activity timecourses were then z-scored within each block.

Analyses included both whole-brain and volume of interest approaches. For whole brain analysis, preprocessed time series data for each block were analyzed with a multiple regression model that included four orthogonal regressors of interest: (1) gain (+$5.00 or +$1.00) versus nongain (+$0.00) anticipation; (2) loss (−$5.00 or −$1.00) versus nonloss (−$0.00) anticipation; (3) "hit" (+$5.00 or +$1.00) versus "miss" (+$0.00) gain outcomes; (4) and "hit" (−$0.00) versus "miss" (−$5.00 or −$1.00) loss outcomes. Other covariates included two orthogonal regressors highlighting the periods of interest (i.e., anticipation and outcome), six regressors describing residual motion, and six regressors modeling baseline, linear, and quadratic trends for each of two task runs. The regressors of interest contrasted activity during predicted periods (2.5 s each), and were convolved with a single gamma-variate function that modeled a prototypical hemodynamic response (Cohen, 1997). Maps of t-statistics representing each of the regressors of interest were transformed into Z-scores, and spatially normalized by warping to Talairach space.

For volume of interest (VOI) analysis, two sets of voxels were chosen for analysis. In the first, an 8 mm sphere centered at the approximate site of implantation in the posterior NAc was created. Secondly, four voxels within the posterior anatomical boundary of the NAc were selected based on their proximity to the expected site of implantation, as well as their significance in whole brain analyses ($Z>2.5$, $p<0.005$, cluster=4; uncorrected). While data from the second VOI is not independent from whole brain analyses, it could be independently compared with distinctly acquired LFP recordings. For percent signal change timecourse plots, signal was extracted from the second VOI, averaged by condition within subject, plotted for visualization, and paired t-test was applied to examine changes in blood oxygen level dependent signal of different anticipations (7).

Structural MRI (7 T). To optimize localization of the dorsal boundaries of the NAc in this patient, a 7 T MRI scan was obtained preoperatively using a magnetization-prepared rapid acquisition gradient echo (MP-RAGE) sequence capable of achieving 1 mm isotropic spatial resolution with whole brain coverage in approximately 5 min. This scan was performed on a GE Discovery MR950 7 T scanner (GE Healthcare, Waukesha, WI) with a 2-channel transmit, 32-channel receive head coil (Nova Medical, Wilmington, MA). We first acquired with a three-plane localizer and a higher-order shimming protocol, and then acquired a grey-matter-nulled (GMn) MP-RAGE volume, consisting of a single 3D coronal slab covering the whole brain. Scan parameters for the GMn MP-RAGE sequence were: 224× 224 matrix, 18 cm field of view, 0.8 mm slice thickness, 280 slices, TR 8.1 ms, TE 3.7 ms, TI 900 ms, TS 3700 ms bandwidth+/−21 kHz, ARC parallel imaging factor 2×1, k-space ordering 2D radial fan beam, scan time 6.66 min. SAR was monitored in all cases using the vendor supplied SAR monitor on the scanner and was below 0.5 W/kg for all scans. Using the GMn MP-RAGE image volume, the signal profile along an oblique line passing through the anterior arm of the internal capsule (where the GM fibers are embedded between the GM of the lenticular nucleus on one side and the caudate nucleus on the other side) was plotted. The scan was registered using Framelink software (Medtronic, Inc., Minneapolis, MN, USA) to a postoperative CT to confirm localization of our electrodes.

Neural Signal Recording and Analyses.

The DBS lead was then implanted in the NAc using frameless stereotactic techniques, and microelectrode recording determined the dorsal and ventral borders of the left NAc (8). A DBS lead (model 3389, Medtronic, Inc., Minneapolis, MN, USA) was placed along the single MER track, and the base of electrode 0 was placed at the ventral border of the NAc. LFPs were recorded differentially from adjacent DBS lead electrode pairs 0-1, 1-2, and 2-3. Limb and head movements were monitored using angular velocity sensors on the limbs (Motus Bioengineering, Inc., Benicia, CA, USA), an accelerometer placed on the forehead, continuous synchronized full-body videography, and intra-operative notes. The participant was instructed to lie still without speaking while keeping his eyes open; the neurologist and psychiatrist (HBS, NW) monitored him continuously. After 60 s of baseline recording without stimulation, the patient performed the MID task on a laptop.

Data acquisition and analysis. Principles for electrophysiological data acquisition and analysis in human have been reported previously (4, 9). LFP signals were pre-amplified with a gain of sixteen by an isolated amplifier (BioAmp 100, Axon Instruments, Inc.) and then passed through an Axon Cyberamp Amplifier/Filters providing a total gain of 50,000 with high-pass filtering at 0.5 Hz and low-pass filtering at 400 Hz (10). The kinematic signals (from the accelerometer and angular velocity sensors, all sampled at 1 kHz), and the video recording (thirty frames/s) were acquired concurrently with the LFP signals (sampled at 4 kHz) using a data acquisition interface (Power1401) and Spike software (version 2.7) (Cambridge Electronic Design, Ltd., Cambridge, England). Signal analysis was performed in MATLAB (version 8.2, The Mathworks, Inc., Natick, MA, USA). Spectrograms of LFP epochs were generated using a short-time Fourier transform of a 1 s sliding window and 90% overlap, averaged across individual trials based on reward or punishment conditions, and normalized to baselines. The power spectral density (PSD) estimate was calculated using Welch's method (1 s sliding window, 50% overlap), averaged across individual trials (2-s epoch starting from cue onset) based on reward or punishment conditions (11).

References

1. Ali R, DiFrancesco M F, Ho A L, Kampman K M, Caplan A, Halpern C H: Attitudes Toward Treating Addiction with Deep Brain Stimulation. Brain, Mar. 15, 2016. pii: S1935-861X(16)30037-7. doi: 10.1016/j.brs.2016.03.009. [Epub ahead of print] PMID: 27066935
2. Ardestani A, Rhoads D, Tavakkoli A: Insulin cessation and diabetes remission after bariatric surgery in adults with insulin-treated type 2 diabetes. Diabetes Care 38:659-664, 2015
3. Beaver J D, Lawrence A D, van Ditzhuijzen J, Davis M H, Woods A, Calder A J: Individual differences in reward drive predict neural responses to images of food. J Neurosci 26:5160-5166, 2006
4. Bello N T, Yeh C Y, Verpeut J L, Walters A L: Binge-like eating attenuates nisoxetine feeding suppression, stress activation, and brain norepinephrine activity. PLoS One 9:e93610, 2014 PMC3973562
5. Benton A L, Hamsher K (eds): Multilingual Aphasia Examination, ed 2nd Edition. Iowa City: AJA Associates, 1989
6. Bergey G K, Morrell M J, Mizrahi E M, Goldman A, King-Stephens D, Nair D, Srinivasan S, Jobst B, Gross R E, Shields D C, Barkley G, Salanova V, Olejniczak P, Cole A, Cash S S, Noe K, Wharen R, Worrell G, Murro A M, Edwards J, Duchowny M, Spencer D, Smith M, Geller E, Gwinn R, Skidmore C, Eisenschenk S, Berg M, Heck C, Van Ness P, Fountain N, Rutecki P, Massey A, O'Donovan C, Labar D, Duckrow R B, Hirsch U, Courtney T, Sun F T, Seale C G: Long-term treatment with responsive brain stimulation in adults with refractory partial seizures. Neurology 84:810-817, 2015 PMC4339127
7. Bewernick B H, Hurlemann R, Matusch A, Kayser S, Grubert C, Hadrysiewicz B, Axmacher N, Lemke M, Cooper-Mahkorn D, Cohen M X, Brockmann H, Lenartz D, Sturm V, Schlaepfer T E: Nucleus accumbens deep brain stimulation decreases ratings of depression and anxiety in treatment-resistant depression. Biol Psychiatry 67:110-116, 2010
8. Bohon C: Greater emotional eating scores associated with reduced frontolimbic activation to palatable taste in adolescents. Obesity (Silver Spring) 22:1814-1820, 2014 PMC4115016
9. Bohon C, Stice E, Spoor S: Female emotional eaters show abnormalities in consummatory and anticipatory food reward: a functional magnetic resonance imaging study. Int J Eat Disord 42:210-221, 2009 PMC2739233
10. Bray G A, Tartaglia L A: Medicinal strategies in the treatment of obesity. Nature 404:672-677, 2000
11. Broft A, Shingleton R, Kaufman J, Liu F, Kumar D, Slifstein M, Abi-Dargham A, Schebendach J, Van Heertum R, Attia E, Martinez D, Walsh B T: Striatal dopamine in bulimia nervosa: a PET imaging study. Int J Eat Disord 45:648-656, 2012 PMC3640453
12. Bronte-Stewart H, Louie S, Batya S, Henderson J M: Clinical motor outcome of bilateral subthalamic nucleus deep-brain stimulation for Parkinson's disease using image-guided frameless stereotaxy. Neurosurgery 67:1088-1093; discussion 1093, 2010
13. Christoffel D J, Golden S A, Walsh J J, Guise K G, Heshmati M, Friedman A K, Dey A, Smith M, Rebusi N, Pfau M, Ables J L, Aleyasin H, Khibnik L A, Hodes G E, Ben-Dor G A, Deisseroth K, Shapiro M L, Malenka R C, Ibanez-Tallon I, Han M H, Russo S J: Excitatory transmission at thalamo-striatal synapses mediates susceptibility to social stress. Nat Neurosci 18:962-964, 2015 PMC4482771
14. Christopher P P, Leykin Y, Appelbaum P S, Holtzheimer P E, 3rd, Mayberg H S, Dunn L B: Enrolling in deep brain stimulation research for depression: influences on potential subjects' decision making. Depress Anxiety 29:139-146, 2012

15. Colles S L, Dixon J B, O'Brien P E: Loss of control is central to psychological disturbance associated with binge eating disorder. Obesity (Silver Spring) 16:608-614, 2008
16. Denys D, Mantione M, Figee M, van den Munckhof P, Koerselman F, Westenberg A, Schuurman R: Deep brain stimulation of the nucleus accumbens for treatment-refractory obsessivecompulsive disorder. Arch Gen Psychiatry 67:1061-1068, 2010
17. Desai S A, Rolston J D, McCracken C E, Potter S M, Gross R E: Asynchronous Distributed Multielectrode Microstimulation Reduces Seizures in the Dorsal Tetanus Toxin Model of Temporal Lobe Epilepsy. Brain Stimul 9:86-100, 2016 PMC4724241
18. Dong Y, Hoover A, Scisco J, Muth E: A new method for measuring meal intake in humans via automated wrist motion tracking. Appl Psychophysiol Biofeedback 37:205-215, 2012 PMC4487660
19. Dougherty D D, Rezai A R, Carpenter L L, Howland R H, Bhati M T, O'Reardon J P, Eskandar E N, Baltuch G H, Machado A D, Kondziolka D, Cusin C, Evans K C, Price L H, Jacobs K, Pandya M, Denko T, Tyrka A R, Brelje T, Deckersbach T, Kubu C, Malone D A, Jr.: A Randomized Sham-Controlled Trial of Deep Brain Stimulation of the Ventral Capsule/Ventral Striatum for Chronic Treatment-Resistant Depression. Biol Psychiatry 78:240-248, 2015
20. Emanuel E J, Wendler D, Grady C: What makes clinical research ethical? JAMA 283:2701-2711, 2000
21. Engel J, Jr., Wiebe S, French J, Sperling M, Williamson P, Spencer D, Gumnit R, Zahn C, Westbrook E, Enos B: Practice parameter: temporal lobe and localized neocortical resections for epilepsy: report of the Quality Standards Subcommittee of the American Academy of Neurology, in association with the American Epilepsy Society and the American Association of Neurological Surgeons. Neurology 60:538-547, 2003
22. Engstrom M, Forsberg A, Sovik T T, Olbers T, Lonroth H, Karlsson J: Perception of control over eating after bariatric surgery for super-obesity—a 2-year follow-up study. Obes Surg 25:1086-1093, 2015
23. Finkelstein E A, Trogdon J G, Cohen J W, Dietz W: Annual medical spending attributable to obesity: payer- and service-specific estimates. Health Aff (Millwood) 28:w822-831, 2009
24. Fisher C E, Dunn L B, Christopher P P, Holtzheimer P E, Leykin Y, Mayberg H S, Lisanby S H, Appelbaum P S: The ethics of research on deep brain stimulation for depression: decisional capacity and therapeutic misconception. Ann N Y Acad Sci 1265:69-79, 2012 3624886
25. Fisher R, Salanova V, Witt T, Worth R, Henry T, Gross R, Oommen K, Osorio I, Nazzaro J, Labar D, Kaplitt M, Sperling M, Sandok E, Neal J, Handforth A, Stern J, DeSalles A, Chung S, Shetter A, Bergen D, Bakay R, Henderson J, French J, Baltuch G, Rosenfeld W, Youkilis A, Marks W, Garcia P, Barbaro N, Fountain N, Bazil C, Goodman R, McKhann G, Babu Krishnamurthy K, Papavassiliou S, Epstein C, Pollard J, Tonder L, Grebin J, Coffey R, Graves N: Electrical stimulation of the anterior nucleus of thalamus for treatment of refractory epilepsy. Epilepsia 51:899-908, 2010
26. Fontaine K R, Barofsky I: Obesity and health-related quality of life. Obes Rev 2:173-182, 2001
27. Fontaine K R, Redden D T, Wang C, Westfall A O, Allison D B: Years of life lost due to obesity. JAMA 289:187-193, 2003
28. Fray P J, Robbins T W: CANTAB battery: proposed utility in neurotoxicology. Neurotoxicol Teratol 18:499-504, 1996
29. Ghazizadeh A, Ambroggi F, Odean N, Fields H L: Prefrontal cortex mediates extinction of responding by two distinct neural mechanisms in accumbens shell. J Neurosci 32:726-737, 2012
30. Giel K E, Zipfel S, Schweizer R, Braun R, Ranke M B, Binder G, Ehehalt S: Eating disorder pathology in adolescents participating in a lifestyle intervention for obesity: associations with weight change, general psychopathology and health-related quality of life. Obes Facts 6:307-316, 2013
31. Goldschmidt A B, Engel S G, Wonderlich S A, Crosby R D, Peterson C B, Le Grange D, Tanofsky-Kraff M, Cao L, Mitchell J E: Momentary affect surrounding loss of control and overeating in obese adults with and without binge eating disorder. Obesity (Silver Spring) 20:1206-1211, 2012 PMC3816927
32. Goodman J H, Berger R E, Tcheng T K: Preemptive low-frequency stimulation decreases the incidence of amygdala-kindled seizures. Epilepsia 46:1-7, 2005
33. Goodman W K, Foote K D, Greenberg B D, Ricciuti N, Bauer R, Ward H, Shapira S S, Hill C L, Rasmussen S A, Okun M S: Deep brain stimulation for intractable obsessive compulsive disorder: pilot study using a blinded, staggered-onset design. Biol Psychiatry 67:535-542, 2010
34. Gorin A A, Niemeier H M, Hogan P, Coday M, Davis C, DiLillo V G, Gluck M E, Wadden T A, West D S, Williamson D, Yanovski S Z: Binge eating and weight loss outcomes in overweight and obese individuals with type 2 diabetes: results from the Look AHEAD trial. Arch Gen Psychiatry 65:1447-1455, 2008 PMC2791958
35. Grilo C M, Masheb R M, Wilson G T: Different methods for assessing the features of eating disorders in patients with binge eating disorder: a replication. Obes Res 9:418-422, 2001
36. Grilo C M, Masheb R M, Wilson G T, Gueorguieva R, White M A: Cognitive-behavioral therapy, behavioral weight loss, and sequential treatment for obese patients with binge-eating disorder: a randomized controlled trial. J Consult Clin Psychol 79:675-685, 2011 PMC3258572
37. Groen W G, Kuijpers W, Oldenburg H S, Wouters M W, Aaronson N K, van Harten W H: Empowerment of Cancer Survivors Through Information Technology: An Integrative Review. J Med Internet Res 17:e270, 2015 PMC4704924
38. Guh D P, Zhang W, Bansback N, Amarsi Z, Birmingham C L, Anis A H: The incidence of co-morbidities related to obesity and overweight: a systematic review and meta-analysis. BMC Public Health 9:88, 2009 PMC2667420
39. Halperin F, Ding S A, Simonson D C, Panosian J, Goebel-Fabbri A, Wewalka M, Hamdy O, Abrahamson M, Clancy K, Foster K, Lautz D, Vernon A, Goldfine A B: Roux-en-Y gastric bypass surgery or lifestyle with intensive medical management in patients with type 2 diabetes: feasibility and 1-year results of a randomized clinical trial. JAMA Surg 149:716-726, 2014 PMC4274782
40. Halpern C, Attiah M, Bale T: Deep brain stimulation for the treatment of binge eating: mechanisms and preclinical models. In: Animal Models of Eating Disorders. Totowa N.J.: Humana Press, 2013
41. Halpern C, Hurtig H, Jaggi J, Grossman M, Won M, Baltuch G: Deep brain stimulation in neurologic disorders. Parkinsonism Relat Disord 13:1-16, 2007 $h4
42. Halpern C H, Tekriwal A, Santollo J, Keating J G, Wolf J A, Daniels D, Bale T L: Amelioration of binge eating by nucleus accumbens shell deep brain stimulation in mice involves D2 receptor modulation. J Neurosci 33:7122-7129, 2013 PMC3703148
43. Halpern C H, Torres N, Hurtig H I, Wolf J A, Stephen J, Oh M Y, Williams N N, Dichter M A, Jaggi J L, Caplan A L, Kampman K M, Wadden T A, Whiting D M, Baltuch G H: Expanding applications of deep brain stimulation: a potential therapeutic role in obesity and addiction management. Acta Neurochir (Wien) 153:2293-2306, 2011
44. Halpern C H, Wolf J A, Bale T L, Stunkard A J, Danish S F, Grossman M, Jaggi J L, Grady M S, Baltuch G H: Deep brain stimulation in the treatment of obesity. J Neurosurg 109:625-634, 2008
45. Hamani C, Diwan M, Isabella S, Lozano A M, Nobrega J N: Effects of different stimulation parameters on the antidepressant-like response of medial prefrontal cortex deep brain stimulation in rats. J Psychiatr Res 44:683-687, 2010
46. Haq I U, Foote K D, Goodman W G, Wu S S, Sudhyadhom A, Ricciuti N, Siddiqui M S, Bowers D, Jacobson C E, Ward H, Okun M S: Smile and laughter induction and intraoperative predictors of response to deep brain stimulation for obsessive-compulsive disorder. Neuroimage 54 Suppl 1:S247-255, 2011 PMC2907450
47. Heck C N, King-Stephens D, Massey A D, Nair D R, Jobst B C, Barkley G L, Salanova V, Cole A J, Smith M C, Gwinn R P, Skidmore C, Van Ness P C, Bergey G K, Park Y D, Miller I, Geller E, Rutecki P A, Zimmerman R, Spencer D C, Goldman A, Edwards J C, Leiphart J W, Wharen R E, Fessler J, Fountain N B, Worrell G A, Gross R E, Eisenschenk S, Duckrow R B, Hirsch U, Bazil C, O'Donovan C A, Sun F T, Courtney T A, Seale C G, Morrell M J: Two-year seizure reduction in adults with medically intractable partial onset epilepsy treated with responsive neurostimulation: final results of the RNS System Pivotal trial. Epilepsia 55:432-441, 2014 PMC4233950
48. Hsu L K, Sullivan S P, Benotti P N: Eating disturbances and outcome of gastric bypass surgery: a pilot study. Int J Eat Disord 21:385-390, 1997
49. Hudson J I, Hiripi E, Pope H G, Jr., Kessler R C: The prevalence and correlates of eating disorders in the National Comorbidity Survey Replication. Biol Psychiatry 61:348-358, 2007 PMC1892232
50. Jarcho J M, Tanofsky-Kraff M, Nelson E E, Engel S G, Vannucci A, Field S E, Romer A L, Hannallah L, Brady S M, Demidowich A P, Shomaker L B, Courville A B, Pine D S, Yanovski J A: Neural activation during anticipated peer evaluation and laboratory meal intake in overweight girls with and without loss of control eating. Neuroimage 108:343-353, 2015 PMC4323624
51. Johnson P M, Kenny P J: Dopamine D2 receptors in addiction-like reward dysfunction and compulsive eating in obese rats. Nat Neurosci 13:635-641, 2010 PMC2947358
52. Kerrigan J F, Litt B, Fisher R S, Cranstoun S, French J A, Blum D E, Dichter M, Shetter A, Baltuch G, Jaggi J, Krone S, Brodie M, Rise M, Graves N: Electrical stimulation of the anterior nucleus of the thalamus for the treatment of intractable epilepsy. Epilepsia 45:346-354, 2004
53. Kiernan M, Moore S D, Schoffman D E, Lee K, King A C, Taylor C B, Kiernan N E, Perri M G: Social support for healthy behaviors: scale psychometrics and prediction of weight loss among women in a behavioral program. Obesity (Silver Spring) 20:756-764, 2012 PMC4718570
54. King-Stephens D, Mirro E, Weber P B, Laxer K D, Van Ness P C, Salanova V, Spencer D C, Heck C N, Goldman A, Jobst B, Shields D C, Bergey G K, Eisenschenk S, Worrell G A, Rossi M A, Gross R E, Cole A J, Sperling M R, Nair D R, Gwinn R P, Park Y D, Rutecki P A, Fountain N B, Wharen R E, Hirsch L J, Miller T O, Barkley G L, Edwards J C, Geller E B, Berg M J, Sadler T L, Sun F T, Morrell M J: Lateralization of mesial temporal lobe epilepsy with chronic ambulatory electrocorticography. Epilepsia 56:959-967, 2015 PMC4676303
55. Knutson B, Westdorp A, Kaiser E, Hommer D: FMRI visualization of brain activity during a monetary incentive delay task. Neuroimage 12:20-27, 2000
56. Kombian S B, Malenka R C: Simultaneous LTP of non-NMDA- and LTD of NMDA-receptor-mediated responses in the nucleus accumbens. Nature 368:242-246, 1994
57. Krause M, German P W, Taha S A, Fields H L: A pause in nucleus accumbens neuron firing is required to initiate and maintain feeding. J Neurosci 30:4746-4756, 2010 PMC2878763
58. Kroemer N B, Sun X, Veldhuizen M G, Babbs A E, de Araujo I E, Small D M: Weighing the evidence: Variance in brain responses to milkshake receipt is predictive of eating behavior. Neuroimage 128:273-283, 2016
59. Kubu C S, Malone D A, Chelune G, Malloy P, Rezai A R, Frazier T, Machado A, Rasmussen S, Friehs G, Greenberg B D: Neuropsychological outcome after deep brain stimulation in the ventral capsule/ventral striatum for highly refractory obsessive-compulsive disorder or major depression. Stereotact Funct Neurosurg 91:374-378, 2013
60. Lee S H, Kim K H, Cheong S M, Kim S, Kooh M, Chin D K: A comparison of the effect of epidural patientcontrolled analgesia with intravenous patient-controlled analgesia on pain control after posterior lumbar instrumented fusion. J Korean Neurosurg Soc 50:205-208, 2011 PMC3218179
61. Liu S Y, Wong S K, Lam C C, Yung M Y, Kong A P, Ng E K: Long-term Results on Weight Loss and Diabetes Remission after Laparoscopic Sleeve Gastrectomy for A Morbidly Obese Chinese Population. Obes Surg, 2015
62. Loring D W, Kapur R, Meador K J, Morrell M J: Differential neuropsychological outcomes following targeted responsive neurostimulation for partial-onset epilepsy. Epilepsia 56:1836-1844, 2015
63. Lucas-Neto L, Reimao S, Oliveira E, Rainha-Campos A, Sousa J, Nunes R G, Goncalves-Ferreira A, Campos J G: Advanced MR Imaging of the Human Nucleus Accumbens—Additional Guiding Tool for Deep Brain Stimulation. Neuromodulation 18:341-348, 2015
64. Maling N, Hashemiyoon R, Foote K D, Okun M S, Sanchez J C: Increased thalamic gamma band activity correlates with symptom relief following deep brain stimulation in humans with Tourette's syndrome. PLoS One 7:e44215, 2012 PMC3435399
65. Mantione M, van de Brink W, Schuurman P R, Denys D: Smoking cessation and weight loss after chronic deep brain stimulation of the nucleus accumbens: therapeutic and research implications: case report. Neurosurgery 66:E218; discussion E218, 2010
66. McCreery D B, Agnew W F, Yuen T G, Bullara L: Charge density and charge per phase as cofactors in neural injury induced by electrical stimulation. IEEE Trans Biomed Eng 37:996-1001, 1990
67. McElroy S L, Hudson J I, Mitchell J E, Wilfley D, Ferreira-Cornwell M C, Gao J, Wang J, Whitaker T, Jonas J, Gasior M: Efficacy and safety of lisdexamfetamine for treatment of adults with moderate to severe binge-eating disorder: a randomized clinical trial. JAMA Psychiatry 72:235-246, 2015
68. Meador K J, Kapur R, Loring D W, Kanner A M, Morrell M J: Quality of life and mood in patients with medically intractable epilepsy treated with targeted responsive neurostimulation. Epilepsy Behav 45:242-247, 2015
69. Moize V, Andreu A, Flores L, Torres F, Ibarzabal A, Delgado S, Lacy A, Rodriguez L, Vidal J: Longterm dietary intake and nutritional deficiencies following sleeve gastrectomy or Roux-En-Y gastric bypass in a mediterranean population. J Acad Nutr Diet 113:400-410, 2013
70. Morrell M J: Responsive cortical stimulation for the treatment of medically intractable partial epilepsy. Neurology 77:1295-1304, 2011
71. O'Connor E C, Kremer Y, Lefort S, Harada M, Pascoli V, Rohner C, Luscher C: Accumbal D1R Neurons Projecting to Lateral Hypothalamus Authorize Feeding. Neuron 88:553-564, 2015
72. Ogden C L, Carroll M D, Kit B K, Flegal K M: Prevalence of childhood and adult obesity in the United States, 2011-2012. JAMA 311:806-814, 2014 PMC4770258
73. Ogden C L, Carroll M D, Kit B K, Flegal K M: Prevalence of obesity in the United States, 2009-2010. NCHS Data Brief: 1-8, 2012
74. Okun M S, Foote K D, Wu S S, Ward H E, Bowers D, Rodriguez R L, Malaty I A, Goodman W K, Gilbert D M, Walker H C, Mink J W, Merritt S, Morishita T, Sanchez J C: A trial of scheduled deep brain stimulation for Tourette syndrome: moving away from continuous deep brain stimulation paradigms. JAMA Neurol 70:85-94, 2013
75. Ooms P, Mantione M, Figee M, Schuurman P R, van den Munckhof P, Denys D: Deep brain stimulation for obsessive-compulsive disorders: long-term analysis of quality of life. J Neurol Neurosurg Psychiatry 85:153-158, 2014
76. Pankevich D E, Teegarden S L, Hedin A D, Jensen C L, Bale T L: Caloric restriction experience reprograms stress and orexigenic pathways and promotes binge eating. J Neurosci 30:16399-16407, 2010 PMC3034235
77. Pisapia J M, Halpern C H, Williams N N, Wadden T A, Baltuch G H, Stein S C: Deep brain stimulation compared with bariatric surgery for the treatment of morbid obesity: a decision analysis study. Neurosurg Focus 29:E15, 2010
78. Puzziferri N, Roshek T B, 3rd, Mayo H G, Gallagher R, Belle S H, Livingston E H: Long-term follow-up after bariatric surgery: a systematic review. JAMA 312:934-942, 2014 PMC4409000
79. Reitan R M, Wolfson D: The Halstead-Reitan neuropsychological test battery:
theory and clinical interpretation. Tucson, Ariz.: Neuropsychology Press, 1985
80. Risinger M W, Gumnit R J: Intracranial electrophysiologic studies. Neuroimaging Clin N Am 5:559-573, 1995
81. Robinson A H, Adler S, Stevens H B, Darcy A M, Morton J M, Safer D L: What variables are associated with successful weight loss outcomes for bariatric surgery after 1 year? Surg Obes Relat Dis 10:697-704, 2014 PMC4125556
82. Safer D L, Robinson A H, Jo B: Outcome from a randomized controlled trial of group therapy for binge eating disorder: comparing dialectical behavior therapy adapted for binge eating to an active comparison group therapy. Behav Ther 41:106-120, 2010 PMC3170852
83. Salanova V, Witt T, Worth R, Henry T R, Gross R E, Nazzaro J M, Labar D, Sperling M R, Sharan A, Sandok E, Handforth A, Stern J M, Chung S, Henderson J M, French J, Baltuch G, Rosenfeld W E, Garcia P, Barbaro N M, Fountain N B, Elias W J, Goodman R R, Pollard J R, Troster A I, Irwin C P, Lambrecht K, Graves N, Fisher R: Long-term efficacy and safety of thalamic stimulation for drugresistant partial epilepsy. Neurology 84:1017-1025, 2015 PMC4352097
84. Schlaepfer T E, Cohen M X, Frick C, Kosel M, Brodesser D, Axmacher N, Joe A Y, Kreft M, Lenartz D, Sturm V: Deep brain stimulation to reward circuitry alleviates anhedonia in refractory major depression. Neuropsychopharmacology 33:368-377, 2008
85. Siebenhofer A, Jeitler K, Horvath K, Berghold A, Posch N, Meschik J, Semlitsch T: Long-term effects of weight-reducing drugs in people with hypertension. Cochrane Database Syst Rev 3:CD007654, 2016
86. Siegel D M, Halpern C H, Bale T: Sex differences in deep brain stimulation amelioration of binge eating, in Biological Psychiatry, 2012, Vol 71, pp 306S-306S
87. Sillay K A, Rutecki P, Cicora K, Worrell G, Drazkowski J, Shih J J, Sharan A D, Morrell M J, Williams J, Wingeier B: Long-term measurement of impedance in chronically implanted depth and subdural electrodes during responsive neurostimulation in humans. Brain Stimul 6:718-726, 2013
88. Stenner M P, Litvak V, Rutledge R B, Zaehle T, Schmitt F C, Voges J, Heinze H J, Dolan R J: Cortical drive of low-frequency oscillations in the human nucleus accumbens during action selection. J Neurophysiol 114:29-39, 2015 PMC4518721
89. Stice E, Spoor S, Bohon C, Small D M: Relation between obesity and blunted striatal response to food is moderated by TaqIA A1 allele. Science 322:449-452, 2008 PMC2681095
90. Strand A D, Aragaki A K, Baguet Z C, Hodges A, Cunningham P, Holmans P, Jones K R, Jones L, Kooperberg C, Olson J M: Conservation of regional gene expression in mouse and human brain. PloS Genet 3:e59, 2007 PMC1853119
91. Stunkard A, Berkowitz R, Tanrikut C, Reiss E, Young L: d-fenfluramine treatment of binge eating disorder. Am J Psychiatry 153:1455-1459, 1996
92. Tabuchi K, Blundell J, Etherton M R, Hammer R E, Liu X, Powell C M, Sudhof T C: A neuroligin-3 mutation implicated in autism increases inhibitory synaptic transmission in mice. Science 318:71-76, 2007 PMC3235367
93. Tanriverdi T, Ajlan A, Poulin N, Olivier A: Morbidity in epilepsy surgery: an experience based on 2449 epilepsy surgery procedures from a single institution. J Neurosurg 110:1111-1123, 2009
94. Teegarden S L, Bale T L: Decreases in dietary preference produce increased emotionality and risk for dietary relapse. Biol Psychiatry 61:1021-1029, 2007
95. Teegarden S L, Bale T L: Effects of stress on dietary preference and intake are dependent on access and stress sensitivity. Physiol Behav 93:713-723, 2008 PMC2483328
96. Telch C F, Agras W S: Do emotional states influence binge eating in the obese? Int J Eat Disord 20:271-279, 1996
97. Tulsky D, Zhu J, Ledbetter M, (eds): WAIS-III WMS-III Technical Manual (Wechsler AdultIntelligence Scale & Wechsler Memory Scale), ed 3rd Edition: Harcourt Brace & Company, 1997

98. Vidal P, Ramon J M, Goday A, Parri A, Crous X, Trillo L, Pera M, Grande L: Lack of adherence to follow-up visits after bariatric surgery: reasons and outcome. Obes Surg 24:179-183, 2014
99. Voges J, Muller U, Bogerts B, Munte T, Heinze H J: Deep brain stimulation surgery for alcohol addiction. World Neurosurg 80:S28 e21-31, 2013
100. Volkow N D, Wise R A: How can drug addiction help us understand obesity? Nat Neurosci 8:555-560,2005
101. Wadden T A, Butryn M L, Byrne K J: Efficacy of lifestyle modification for long-term weight control. Obes Res 12 Suppl:1515-1625, 2004
102. Wagenaar D A, Pine J, Potter S M: Effective parameters for stimulation of dissociated cultures using multi-electrode arrays. J Neurosci Methods 138:27-37, 2004
103. Wang G J, Volkow N D, Logan J, Pappas N R, Wong C T, Zhu W, Netusil N, Fowler J S: Brain dopamine and obesity. Lancet 357:354-357, 2001
104. Weaver F M, Follett K, Stern M, Hur K, Harris C, Marks W J, Jr., Rothlind J, Sagher O, Reda D, Moy C S, Pahwa R, Burchiel K, Hogarth P, Lai E C, Duda J E, Holloway K, Samii A, Horn S, Bronstein J, Stoner G, Heemskerk J, Huang G D: Bilateral deep brain stimulation vs best medical therapy for patients with advanced Parkinson disease: a randomized controlled trial. JAMA 301:63-73, 2009 PMC2814800
105. Weygandt M, Mai K, Dommes E, Leupelt V, Hackmack K, Kahnt T, Rothemund Y, Spranger J, Haynes J D: The role of neural impulse control mechanisms for dietary success in obesity. Neuroimage 83:669-678, 2013
106. White M A, Kalarchian M A, Masheb R M, Marcus M D, Grilo C M: Loss of control over eating predicts outcomes in bariatric surgery patients: a prospective, 24-month follow-up study. J Clin Psychiatry 71:175-184, 2010 PMC2831110
107. Wonderlich J A, Lavender J M, Wonderlich S A, Peterson C B, Crow S J, Engel S G, Le Grange D, Mitchell J E, Crosby R D: Examining convergence of retrospective and ecological momentary assessment measures of negative affect and eating disorder behaviors. Int J Eat Disord 48:305-311, 2015

References for Example 5

1. Kessler R C, et al. (2005) Lifetime prevalence and age-of-onset distributions of DSM-IV disorders in the National Comorbidity Survey Replication. *Archives of general psychiatry* 62(6):593-602.
2. Weintraub D, et al. (2010) Impulse control disorders in Parkinson disease: a cross-sectional study of 3090 patients. *Archives of neurology* 67(5):589-595.
3. Baxter L R, Jr. (2003) Basal ganglia systems in ritualistic social displays: reptiles and humans; function and illness. *Physiology & behavior* 79(3):451-460.
4. Martin L E & Potts G F (2004) Reward sensitivity in impulsivity. *Neuroreport* 15(9):1519-1522.
5. Smith C T, et al. (2016) Modulation of impulsivity and reward sensitivity in intertemporal choice by striatal and midbrain dopamine synthesis in healthy adults. *Journal of neurophysiology* 115(3):1146-1156.
6. Demos K E, Heatherton T F, & Kelley W M (2012) Individual differences in nucleus accumbens activity to food and sexual images predict weight gain and sexual behavior. *J Neurosci* 32(16):5549-5552.
7. Buckholtz J W, et al. (2010) Mesolimbic dopamine reward system hypersensitivity in individuals with psychopathic traits. *Nat Neurosci* 13(4):419-421.
8. Dalley J W, Everitt B J, & Robbins T W (2011) Impulsivity, compulsivity, and top-down cognitive control. *Neuron* 69(4):680-694.
9. Crockett M J, et al. (2013) Restricting temptations: neural mechanisms of precommitment. *Neuron* 79(2):391-401.
10. Knutson B, Westdorp A, Kaiser E, & Hommer D (2000) FMRI visualization of brain activity during a monetary incentive delay task. *Neuroimage* 12(1):20-27.
11. Richard J M, Ambroggi F, Janak P H, & Fields H L (2016) Ventral Pallidum Neurons Encode Incentive Value and Promote Cue-Elicited Instrumental Actions. *Neuron* 90(6): 1165-1173.
12. Roitman M F, Stuber G D, Phillips P E, Wightman R M, & Carelli R M (2004) Dopamine operates as a subsecond modulator of food seeking. *The Journal of neuroscience: the official journal of the Society for Neuroscience* 24(6): 1265-1271.
13. Taha S A & Fields H L (2006) Inhibitions of nucleus accumbens neurons encode a gating signal for reward-directed behavior. *J Neurosci* 26(1):217-222.
14. Morrell M J & Group RNSSiES (2011) Responsive cortical stimulation for the treatment of medically intractable partial epilepsy. *Neurology* 77(13):1295-1304.
15. Halpern C H, et al. (2013) Amelioration of binge eating by nucleus accumbens shell deep brain stimulation in mice involves D2 receptor modulation. *J Neurosci* 33(17): 7122-7129.
16. Schultz W, Apicella P, Scarnati E, & Ljungberg T (1992) Neuronal activity in monkey ventral striatum related to the expectation of reward. *The Journal of neuroscience: the official journal of the Society for Neuroscience* 12(12): 4595-4610.
17. Carelli R M & Deadwyler S A (1994) A comparison of nucleus accumbens neuronal firing patterns during cocaine self-administration and water reinforcement in rats. *The Journal of neuroscience: the official journal of the Society for Neuroscience* 14(12):7735-7746.
18. Knutson B, Wimmer G E, Kuhnen C M, & Winkielman P (2008) Nucleus accumbens activation mediates the influence of reward cues on financial risk taking. *Neuroreport* 19(5):509-513.
19. Magri C, Schridde U, Murayama Y, Panzeri S, & Logothetis N K (2012) The amplitude and timing of the BOLD signal reflects the relationship between local field potential power at different frequencies. *The Journal of neuroscience: the official journal of the Society for Neuroscience* 32(4):1395-1407.
20. Lu H, et al. (2007) Synchronized delta oscillations correlate with the resting-state functional MRI signal. *Proc Natl Acad Sci USA* 104(46):18265-18269.
21. Teegarden S L & Bale T L (2007) Decreases in dietary preference produce increased emotionality and risk for dietary relapse. *Biological psychiatry* 61(9):1021-1029.
22. Knutson B, Katovich K, & Suri G (2014) Inferring affect from fMRI data. *Trends in cognitive sciences* 18(8):422-428.
23. Einevoll G T, Kayser C, Logothetis N K, & Panzeri S (2013) Modelling and analysis of local field potentials for studying the function of cortical circuits. *Nat Rev Neurosci* 14(11):770-785.
24. Bergey G K, et al. (2015) Long-term treatment with responsive brain stimulation in adults with refractory partial seizures. *Neurology* 84(8):810-817.
25. Rosin B, et al. (2011) Closed-loop deep brain stimulation is superior in ameliorating parkinsonism. *Neuron* 72(2): 370-384.

26. Wingeier B, et al. (2006) Intra-operative STN DBS attenuates the prominent beta rhythm in the STN in Parkinson's disease. *Experimental neurology* 197(1):244-251.
27. Little S, et al. (2013) Adaptive deep brain stimulation in advanced Parkinson disease. *Ann Neurol* 74(3):449-457.
28. Avila I, et al. (2010) Beta frequency synchronization in basal ganglia output during rest and walk in a hemiparkinsonian rat. *Exp Neurol* 221(2):307-319.
29. Widge A S & Moritz C T (2014) Pre-frontal control of closed-loop limbic neurostimulation by rodents using a brain-computer interface. *J Neural Eng* 11(2):024001.

References for Example 5 Materials and Methods

1. Halpern C H, Attiah M A, Tekriwal A, & Baltuch G H (2014) A step-wise approach to deep brain stimulation in mice. Acta Neurochir (Wien) 156(8):1515-1521.
2. Gunaydin L A, et al. (2014) Natural neural projection dynamics underlying social behavior. Cell 157(7):1535-1551.
3. Lammel S, et al. (2012) Input-specific control of reward and aversion in the ventral tegmental area. Nature 491 (7423):212-217.
4. Miller K J, et al. (2007) Spectral changes in cortical surface potentials during motor movement. J Neurosci 27(9):2424-2432.
5. Quiroga R Q, Nadasdy Z, & Ben-Shaul Y (2004) Unsupervised spike detection and sorting with wavelets and superparamagnetic clustering. Neural Comput 16(8): 1661-1687.
6. Sacchet M D & Knutson B (2013) Spatial smoothing systematically biases the localization of reward-related brain activity. Neuroimage 66:270-277.
7. Leong J K, Pestilli F, Wu C C, Samanez-Larkin G R, & Knutson B (2016) White-Matter Tract Connecting Anterior Insula to Nucleus Accumbens Correlates with Reduced Preference for Positively Skewed Gambles. Neuron 89(1):63-69.
8. Bronte-Stewart H, Louie S, Batya S, & Henderson J M (2010) Clinical motor outcome of bilateral subthalamic nucleus deep-brain stimulation for Parkinson's disease using image-guided frameless stereotaxy. Neurosurgery 67 (4): 1088-1093; discussion 1093.
9. Blumenfeld Z, et al. (2016) Sixty-hertz stimulation improves bradykinesia and amplifies subthalamic low-frequency oscillations. Mov Disord.
10. Whitmer D, et al. (2012) High frequency deep brain stimulation attenuates subthalamic and cortical rhythms in Parkinson's disease. Front Hum Neurosci 6:155.
11. Welch P D (1967) Use of Fast Fourier Transform for Estimation of Power Spectra —a Method Based on Time Averaging over Short Modified Periodograms. Ieee T Acoust Speech Au15(2):70-&.

P EMBODIMENTS

Embodiment P1. A method of detecting low frequency modulations in the nucleus accumbens of a subject, wherein the subject is diagnosed with, or suspected of having, a loss of control or impulse control disorder, the method comprising: inserting at least one electrode into the nucleus accumbens of the subject; and recording brain wave activity in the nucleus accumbens of the subject.

Embodiment P2. The method of embodiment P1, wherein the loss of control disorder comprises a disorder that is associated with a lack of impulse control, and wherein the loss of control disorder includes one or more of substance abuse, sex addiction or compulsive sexuality, kleptomania, pyromania, trichotillomania, panic disorder, Intermittent Explosive Disorder, compulsive behaviors including gambling, binge eating, night eating, loss of control eating, emotional or stress eating, compulsive eating, purge behaviors, or suicidal ideation/attempt.

Embodiment P3. The method of embodiment P1 or P2, further comprising administering, in response to the low frequency modulation, an electrical stimulation to the nucleus accumbens of the subject.

Embodiment P4. The method of embodiment P3, wherein a dose of the electrical stimulation is less than a dose corresponding to deep brain stimulation.

Embodiment P5. The method of embodiment P3, wherein a frequency of the electrical stimulation is 5 hertz, 10 hertz, 12 hertz, 160 hertz, 212 hertz, or 333 hertz.

Embodiment P6. The method of any of embodiments P3-P5, wherein a burst duration of the electrical stimulation is 100 milliseconds, 1 minute, 15 minutes, or 1 hour.

Embodiment P7. The method of any of embodiments P3-P5, wherein a duty cycle of the electrical stimulation is continuous, bursting, or on for a length of time and off for a different length of time.

Embodiment P8. The method of any of embodiments P1-P7, wherein the low frequency modulation comprises a modulation having a frequency between about 0 hertz-38 hertz.

Embodiment P9. The method of any of embodiments P1-P7, wherein the low frequency modulation comprises a modulation having a frequency between about 0 hertz-12 hertz.

Embodiment P10. The method of any of embodiments P1-P7, wherein the low frequency modulation comprises a modulation having a frequency between about 0 hertz-8 hertz.

Embodiment P11. The method of any of embodiments P1-P7, wherein the low frequency modulation comprises a modulation having a frequency between about 0 hertz-3 hertz.

Embodiment P12. The method of any of embodiments P1-P11, wherein the at least one electrode is a deep brain electrode.

Embodiment P13. An apparatus, comprising: at least one electrode adapted to at least measure brain wave activity in a nucleus accumbens of a subject and to apply an electrical current to the nucleus accumbens of the subject; a controller configured to at least: detect, based at least in part on the measured brain wave activity, at least one low frequency modulation in the nucleus accumbens of the subject, and administer, in response to the detection of the at least one low frequency modulation, electrical stimulation to the nucleus accumbens of the subject, wherein the administering of electrical stimulation includes applying, by the at least one electrode, the electrical current to the nucleus accumbens of the subject.

Embodiment P14. The apparatus of embodiment P13, wherein the loss of control disorder comprises a disorder that is associated with a lack of impulse control, and wherein the loss of control disorder includes one or more of substance abuse, compulsive gambling, binge eating, or suicidal ideation.

Embodiment P15. The apparatus of embodiment P13 or P14, wherein a dose of the electrical stimulation is less than a dose corresponding to deep brain stimulation.

Embodiment P16. The apparatus of embodiments P13-P15, wherein a frequency of the electrical stimulation is 5 hertz, 10 hertz, 12 hertz, 160 hertz, 212 hertz, or 333 hertz.

Embodiment P17. The apparatus of any of embodiments P13-P15, wherein a burst duration of the electrical stimulation is 100 milliseconds, 1 minute, 15 minutes, or 1 hour.

Embodiment P18. The apparatus of any of embodiments P13-P17, wherein a duty cycle of the electrical stimulation is continuous, bursting, or on for a length of time and off for a different length of time.

Embodiment P19. The apparatus of any of embodiments P13-P17, wherein the at least one low frequency modulation comprises a modulation having a frequency between about 0 hertz-38 hertz.

Embodiment P20. The apparatus of any of embodiments P13-P17, wherein the at least one low frequency modulation comprises a modulation having a frequency between about 0 hertz-12 hertz.

Embodiment P21. The apparatus of any of embodiments P13-P17, wherein the at least one low frequency modulation comprises a modulation having a frequency between about 0 hertz-8 hertz.

Embodiment P22. The apparatus of any of embodiments P13-P17, wherein the low frequency modulation comprises a modulation having a frequency between about 0 hertz-3 hertz.

Embodiment P23. A system for the treatment of loss of control disorders of a subject, the system comprising: the apparatus of any of embodiments P13-P22; an optimizer comprising: at least one processor; and at least one memory including program code which when executed by the at least one memory provides operations comprising: receiving treatment data for a first administration of electrical stimulation and a second administration of electrical stimulation, wherein the first administration of electrical stimulation comprises an application of electrical current in accordance to a first set of parameters, and wherein the second administration of electrical stimulation comprises another application of electrical current in accordance to a second set of parameters; obtaining patient data indicative of a result of the first electrical stimulation and the second electrical stimulation; and adjusting, based at least on the treatment data and the patient data, a third set of parameters for applying electrical current during a subsequent administration of electrical stimulation.

Embodiment P24. The system of embodiment P23, wherein the first, second, and third set of parameters include a frequency, a duty cycle, and a burst duration for the application of electrical current.

Embodiment P25. The system of embodiment P23, wherein the patient data includes behavioral data associated with the subject.

Embodiment P26. The system of any of embodiments P23-P25, wherein the at least one of the frequency, duty cycle, and burst duration is adjusted to maximize a reduction or improvement in one or more symptoms associated with the loss of control disorder.

What is claimed is:

1. A method of detecting an anticipatory biomarker in the form of a low frequency modulation in a nucleus accumbens of a subject in need thereof, wherein the subject in need is one diagnosed with, or suspected of having, a loss of control or impulse control disorder and wherein the subject in need has at least one electrode inserted into their nucleus accumbens, the method comprising:

recording brain wave activity in a frequency range of from 0-38 hertz in the nucleus accumbens of the subject and in the absence of electrical stimulation administered to the brain; and detecting a change in power compared to a baseline in a delta band corresponding to a frequency of from 1-4 Hz, wherein detection of an increase in power in the delta band indicates detection of the anticipatory biomarker in the form of a low frequency modulation, wherein said low frequency modulation precedes the onset of a disorder symptom manifestation, wherein the method further comprises preventing the onset by administering, in response to detecting the anticipatory biomarker, an electrical stimulation to the nucleus accumbens of the subject.

2. The method of claim 1, wherein the loss of control disorder comprises a disorder that is associated with a lack of impulse control, and wherein the loss of control disorder includes one or more of substance abuse, sex addiction or compulsive sexuality, kleptomania, pyromania, trichotillomania, panic disorder, Intermittent Explosive Disorder, compulsive behaviors including gambling, binge eating, night eating, loss of control eating, emotional or stress eating, compulsive eating, purge behaviors, or suicidal ideation/attempt.

3. The method of claim 1, wherein the electrical stimulation is administered as a closed-loop neurostimulation.

4. The method of claim 1, wherein the electrical stimulation is administered at a frequency of 5 hertz, 10 hertz, 12 hertz, 160 hertz, 212 hertz, or 333 hertz.

5. The method of claim 1, wherein the electrical stimulation is administered with a burst duration of 100 milliseconds, 1 minute, 15 minutes, or 1 hour.

6. The method of claim 1, wherein the electrical stimulation is administered with a duty cycle that is continuous, bursting, or on for a length of time and off for a different length of time.

7. The method of claim 1, wherein the low frequency modulation is a 10-45% increase in power compared to the baseline.

8. The method of claim 1, wherein the at least one electrode inserted into their nucleus accumbens comprises a deep brain electrode.

9. A method of detecting an anticipatory biomarker in the form of a low frequency modulation in a nucleus accumbens of a subject in need thereof, wherein the subject in need is one diagnosed with, or suspected of having, a loss of control or impulse control disorder and wherein the subject in need has at least one electrode inserted into their nucleus accumbens, the method comprising:

receiving brain wave activity in a frequency range of from 0-38 hertz that was recorded in the nucleus accumbens of the subject and in the absence of electrical stimulation administered to the brain; and detecting a change in power compared to a baseline in a delta band of the received brain wave activity corresponding to a frequency of from 1-4 Hz, wherein detection of an increase in power in the delta band indicates detection of the anticipatory biomarker in the form of a low frequency modulation, wherein said low frequency modulation precedes the onset of a disorder symptom manifestation, wherein the method further comprises preventing the onset by administering, in response to detecting the anticipatory biomarker, an electrical stimulation to the nucleus accumbens of the subject.

* * * * *